United States Patent
Zhu

(10) Patent No.: US 7,205,135 B2
(45) Date of Patent: Apr. 17, 2007

(54) REGULATION OF HUMAN ADENYLATE CYCLASE

(75) Inventor: Zhimin Zhu, Waban, MA (US)

(73) Assignee: Bayer HealthCare AG, Leverkusen (DE)

( * ) Notice: Subject to any disclaimer, the term of this patent is extended or adjusted under 35 U.S.C. 154(b) by 271 days.

(21) Appl. No.: 10/416,577

(22) PCT Filed: Nov. 12, 2001

(86) PCT No.: PCT/EP01/13060

§ 371 (c)(1),
(2), (4) Date: Oct. 14, 2003

(87) PCT Pub. No.: WO02/38747

PCT Pub. Date: May 16, 2002

(65) Prior Publication Data

US 2004/0063174 A1    Apr. 1, 2004

Related U.S. Application Data

(60) Provisional application No. 60/267,181, filed on Feb. 8, 2001, provisional application No. 60/247,005, filed on Nov. 13, 2000.

(51) Int. Cl.
*C12N 9/88* (2006.01)
*C12N 15/60* (2006.01)
*C07K 16/18* (2006.01)
*C12P 21/02* (2006.01)

(52) U.S. Cl. .................. 435/183; 435/194; 435/196; 435/193; 424/94.5

(58) Field of Classification Search ................ 435/183, 435/194, 193, 196; 424/94.5
See application file for complete search history.

(56) References Cited

U.S. PATENT DOCUMENTS 6,107,076 A    8/2000    Tang et al.

FOREIGN PATENT DOCUMENTS

WO    WO 01 44453    6/2001

OTHER PUBLICATIONS

WO200144453-A1 Kapeller-Libermann et al Novel Isolated adenylated cyclase protein, 25678.*
Feinstein et al.: "Molecular cloning and characterization of $Ca^{2+}$/calmodulin-insensitive adenylyl cyclase from rat brain"; Proc.Nat. Acad.Sci.USA; vol. 88, 10173-10177; Nov. 1991.
Kikuno et al.; "Prediction of the Coding Sequences of Unidentified Human Genes. XIV. The Complete Sequences of 100 New cDNA Clones from Brain Which Code for Large Proteins *in vitro*"; DNA Research; vol. 6, 197-205 (1999).
Database EMBL 'Online! ADCY2 or KIAA1060; adenylate cyclase type II, Oct. 1, 1994; Database Accession No. Q08462.
Ohara et al.: "direct submission"; Database EMBL 'Online! Homo sapiens mRNA for KIAA1060 protein, Aug. 4, 1999; Database Accession No. AB028983.
Hellevuo et al.: "A novel adenylyl cyclase sequence cloned from the human erythroleukemia cell line"; Biochem & Biophys Research Communications; vol. 192; 311-318; (1993).
Hellevuo et al.: "The characterization of a Novel Human Adenylyl Cyclase Which is Present in Brain and Other Tissues"; The Jour of Biological Chem; vol. 270; 11581-11589; May 12, 1995.
Simonds et al.: "G protein regulation of adenylate cyclase"; Trends in Pharmacological Sciences; vol. 20;66-73; Feb. 1999.

\* cited by examiner

*Primary Examiner*—Rebecca E. Prouty
*Assistant Examiner*—Kagnew Gebreyesus
(74) *Attorney, Agent, or Firm*—Banner & Witcoff, Ltd.

(57) ABSTRACT

Reagents which regulate human adenylate cyclase and reagents which bind to human adenylate cyclase gene products can play a role in preventing, ameliorating, or correcting dysfunctions or diseases including, but not limited to, peripheral and central nervous system disorders, disorders of the genito-urinary system including but not limited to benign prostatic hyperplasia and urinary incontinence, obesity, COPD and diabetes.

3 Claims, 22 Drawing Sheets

Fig. 1

```
ggagcctaccataagcacctcatggaactcgctcttcagcaaacatatcagga
cacctgtaattgcatcaagtcgcggatcaagttggaatttgaaaaacgtcaac
aggagcggcttctgctctccctgctgccggcccacatcgccatggagatgaaa
gcggagatcatccagaggctgcagggccccaaggcgggccagatggagaacac
aaataacttccacaacctgtatgtgaagcggcatacaaacgtgagcatcttat
acgctgacatcgttggctttacccggctggcaagtgactgctccccgggagaa
ctagtccacatgctgaatgagctctttggaaagtttgatcaaattgcaaagga
gaatgaatgcatgagaattaaaattttaggagactgctactactgtgtatctg
gactccctatatctctccctaaccatgccaagaactgtgtgaaaatggggctg
gacatgtgtgaagccataaagaaagtgagggatgctactggagttgatatcaa
catgcgcgtgggcgtgcattctgggaatgtcctgtgtggcgtgattggtctgc
agaagtggcaatatgatgtgtggtcacatgatgtgaccttggccaaccacatg
gaagctggaggggtccctggacgtgttcacatttcttctgtcaccctggagca
cttgaatggcgcttataaagtggaggagggagatggtgacattagggaccat
atttaaaacagcacctggtgaaaacctactttgtgatcaaccccaagggagaa
cgacggagcccccagcatctcttcagacctcgccacaccttgatggagccaa
aatgagggcctcggtccgcatgacccggtacttggagtcctgggggggcagcca
agcccttttgcacacctacatcacagggacagcatgaccacagagaacggcaag
atcagcaccacggatgtaccatgggtcagcataatttcaaaatcgcacctt
aagaaccaagtcacaaaagaagagatttgaagaagaattgaatgaaaggatga
ttcaagcaattgatgggattaatgcacagaagcaatggctcaagtctgaagac
attcagagaatctcactgcttttctataacaaagtactagaaaagagtaccg
ggccacggcactgccagcgttcaagtattatgtgacttgtgcctgtctcatat
tcttctgcatcttcattgtgcagattctcgtgctgccaaaaacgtctgtcctg
ggcatctcctttggggctgcgtttctcttgctggccttcatcctcttcgtctg
ctttgctggacagcttctgcaatgcagcaaaaaagcctctcccctgctcatgt
ggcttttgaagtcctcgggcatcattgccaaccgccctggccacggatctct
ctcacgatcatcaccacagccatcatattaatgatggccgtgttcaacatgtt
tttcctgagtgactcagaggaaacaatccctccaactgccaacacaacaaaca
caagcttttcagcctcaaataatcaggtggcgattctgcgtgcgcagaattta
ttttcctcccgtacttatctacagctgcattctgggactgatatcctgttc
cgtgttcctgcgggtaaactatgagctgaagatgttgatcatgatggtggcct
tggtgggctacaacaccatcctactccacaccacgcccacgtcctgggcgac
tacagccaggtcttatttgagagaccaggcatttggaaagacctgaagaccat
gggctctgtgtctctctctatattcttcatcacactgcttgttctgggtagac
agaatgaatattactgtaggttagacttcttatggaagaacaaattcaaaaaa
gagcgggaggagatagagaccatggagaacctgaaccgcgtgctgctggagaa
cgtgcttcccgcgcacgtggctgagcacttcctggccaggagcctgaagaatg
aggagctataccaccagtcctatgactgcgtctgtgtcatgtttgcctccatt
ccggatttcaaagaattttatacagaatccgacgtgaacaaggagggcttgga
atgccttcggctcctgaacgagatcatcgctgactttgatgatcttcttttcca
agccaaaattcagtggagttgaaaagattaagaccattggcagcacatacatg
gcagcaacaggtctgagcgctgtgcccagccaggagcactcccaggagcccga
gcggcagtacatgcacattggcaccatggtggagtttgcttttgccctggtag
ggaagctggatgccatcaacaagcactccttcaacgacttcaaattgcgagtg
ggtattaaccatggacctgtgatagctggtgtgattggagctcagaagccaca
atatgatatctggggcaacactgtcaatgtggccagtaggatggacagcaccg
gagtcctggacaaaatacaggttaccgaggagacgagcctcgtcctgcagacc
ctcggatacacgtgcacctgtcgaggaataatcaacgtgaaaggaaagggga
cctgaagacgtactttgtaaacacagaaatgtcaaggtccctttcccagagca
acgtggcatcctga
```

Fig. 2

GAYHKHLMELALQQTYQDTCNCIKSRIKLEFEKRQQERLLLSLLPAHIAMEMK
AEIIQRLQGPKAGQMENTNNFHNLYVKRHTNVSILYADIVGFTRLASDCSPGE
LVHMLNELFGKFDQIAKENECMRIKILGDCYYCVSGLPISLPNHAKNCVKMGL
DMCEAIKKVRDATGVDINMRVGVHSGNVLCGVIGLQKWQYDVWSHDVTLANHM
EAGGVPGRVHISSVTLEHLNGAYKVEEGDGDIRDPYLKQHLVKTYFVINPKGE
RRSPQHLFRPRHTLDGAKMRASVRMTRYLESWGAAKPFAHLHHRDSMTTENGK
ISTTDVPMGQHNFQNRTLRTKSQKKRFEEELNERMIQAIDGINAQKQWLKSED
IQRISLLFYNKVLEKEYRATALPAFKYYVTCACLIFFCIFIVQILVLPKTSVL
GISFGAAFLLLAFILFVCFAGQLLQCSKKASPLLMWLLKSSGIIANRPWPRIS
LTIITTAIILMMAVFNMFFLSDSEETIPPTANTTNTSFSASNNQVAILRAQNL
FFLPYFIYSCILGLISCSVFLRVNYELKMLIMMVALVGYNTILLHTHAHVLGD
YSQVLFERPGIWKDLKTMGSVSLSIFFITLLVLGRQNEYYCRLDFLWKNKFKK
EREEIETMENLNRVLLENVLPAHVAEHFLARSLKNEELYHQSYDCVCVMFASI
PDFKEFYTESDVNKEGLECLRLLNEIIADFDDLLSKPKFSGVEKIKTIGSTYM
AATGLSAVPSQEHSQEPERQYMHIGTMVEFAFALVGKLDAINKHSFNDFKLRV
GINHGPVIAGVIGAQKPQYDIWGNTVNVASRMDSTGVLDKIQVTEETSLVLQT
LGYTCTCRGIINVKGKGDLKTYFVNTEMSRSLSQSNVAS

Fig. 3

```
atgcggcaccgccgctacctgcgggaccgctccgaggaggcggcgggcggcgg
agacgggctgccgcggtcccgggactggctctacgagtcctactactgcatga
gccagcagcacccgctcatcgtcttcctgctgctcatcgtcatgggctcctgc
ctcgccctgctcgccgtcttcttcgcgctcgggctggaagttgaagaccatgt
ggcgtttctaataacagttccaactgccctggcgattttcttttgcgatattta
tcctggtctgcatcgagtctgtgtttaagaagctgctgcgccttctcgttg
gtgatatggatatgccttgttgccatgggatacctgttcatgtgttttggagg
caccgtctctccctgggaccaggtatcgttcttcctcttcatcatcttcgtgg
tgtacaccatgctgcccttcaacatgcgagacgccatcattgccagcgtcctc
acctcctcctccacaccatcgtgcttagcgtctgcctgtctgcaacaccggg
aggcaaggagcacctggtctggcagatcctggccaatgtgatcattttcatct
gtgggaacctggcgggagcctaccataagcacctcatggaactcgctcttcag
caaacatatcaggacacctgtaattgcatcaagtcgcggatcaagttggaatt
tgaaaaacgtcaacaggagcggcttctgctctccctgctgccggcccacatcg
ccatggagatgaaagcggagatcatccagaggctgcagggcccaaggcgggc
cagatggagaacacaaataacttccacaacctgtatgtgaagcggcatacaaa
cgtgagcatcttatacgctgacatcgttggctttacccggctggcaagtgact
gctccccgggagaactagtccacatgctgaatgagctctttggaaagtttgat
caaattgcaaaggagaatgaatgcatgagaattaaaattttaggagactgcta
ctactgtgtatctggactccctatatctctccctaaccatgccaagaactgtg
tgaaaatggggctggacatgtgtgaagccataaagaaagtgagggatgctact
ggagttgatatcaacatgcgcgtgggcgtgcattctgggaatgtcctgtgtgg
cgtgattggtctgcagaagtggcaatatgatgtgtggtcacatgatgtgacct
tggccaaccacatggaagctggaggggtccctggacgttcacatttcttct
gtcaccctggagcacttgaatggcgcttataaagtggaggaggggagatggtga
cattagggacccatatttaaaacagcacctggtgaaaacctactttgtgatca
accccaagggagaacgacggagcccccagcatctcttcagacctcgccacacc
cttgatggagccaaaatgagggcctcggtccgcatgacccggtacttggagtc
ctgggggggcagccaagcccttttgcacacctacatcacagggacagcatgacca
cagagaacggcaagatcagcaccacggatgtacccatgggtcagcataatttt
```

Fig. 3-1

```
caaaatcgcaccttaagaaccaagtcacaaaagaagagatttgaagaagaatt
gaatgaaaggatgattcaagcaattgatgggattaatgcacagaagcaatggc
tcaagtctgaagacattcagagaatctcactgcttttctataacaaagtacta
gaaaaagagtaccgggccacggcactgccagcgttcaagtattatgtgacttg
tgcctgtctcatattcttctgcatcttcattgtgcagattctcgtgctgccaa
aaacgtctgtcctgggcatctcctttggggctgcgtttctcttgctggccttc
atcctcttcgtctgctttgctggacagcttctgcaatgcagcaaaaaagcctc
tcccctgctcatgtggcttttgaagtcctcgggcatcattgccaaccgccct
ggccacggatctctctcacgatcatcaccacagccatcatattaatgatggcc
gtgttcaacatgtttttcctgagtgactcagaggaaacaatccctccaactgc
caacacaacaaacacaagctttcagcctcaaataatcaggtggcgattctgc
gtgcgcagaatttattttcctcccgtactttatctacagctgcattctggga
ctgatatcctgttccgtgttcctgcgggtaaactatgagctgaagatgttgat
catgatggtggccttggtgggctacaacaccatcctactccacacccacgccc
acgtcctgggcgactacagccaggtcttatttgagagaccaggcatttggaaa
gacctgaagaccatgggctctgtctctctctatattcttcatcacactgct
tgttctgggtagacagaatgaatattactgtaggttagacttcttatgaaga
acaaattcaaaaagagcgggaggagatagagaccatggagaacctgaaccgc
gtgctgctggagaacgtgcttcccgcgcacgtggctgagcacttcctggccag
gagcctgaagaatgaggagctataccaccagtcctatgactgcgtctgtgtca
tgtttgcctccattccggatttcaaagaattttatacagaatccgacgtgaac
aaggagggcttggaatgccttcggctcctgaacgagatcatcgctgactttga
tgatcttctttccaagccaaaattcagtggagttgaaaagattaagaccattg
gcagcacatacatggcagcaacaggtctgagcgctgtgcccagccaggagcac
tcccaggagcccgagcggcagtacatgcacattggcaccatggtggagtttgc
ttttgccctggtagggaagctggatgccatcaacaagcactccttcaacgact
tcaaattgcgagtgggtattaaccatggacctgtgatagctggtgtgattgga
gctcagaagccacaatatgatatctggggcaacactgtcaatgtggccagtag
gatggacagcaccggagtcctggacaaaataccaggttaccgaggagacgagcc
tcgtcctgcagaccctcggatacacgtgcacctgtcgaggaataatcaacgtg
aaaggaaaggggggacctgaagacgtactttgtaaacacagaaatgtcaaggtc
cctttcccagagcaacgtggcatcctga
```

Fig. 4

MRHRRYLRDRSEEAAGGGDGLPRSRDWLYESYYCMSQQHPLIVFLLLIVMGSC
LALLAVFFALGLEVEDHVAFLITVPTALAIFFAIFILVCIESVFKKLLRLFSL
VIWICLVAMGYLFMCFGGTVSPWDQVSFFLFIIFVVYTMLPFNMRDAIIASVL
TSSSHTIVLSVCLSATPGGKEHLVWQILANVIIFICGNLAGAYHKHLMELALQ
QTYQDTCNCIKSRIKLEFEKRQQERLLLSLLPAHIAMEMKAEIIQRLQGPKAG
QMENTNNFHNLYVKRHTNVSILYADIVGFTRLASDCSPGELVHMLNELFGKFD
QIAKENECMRIKILGDCYYCVSGLPISLPNHAKNCVKMGLDMCEAIKKVRDAT
GVDINMRVGVHSGNVLCGVIGLQKWQYDVWSHDVTLANHMEAGGVPGRVHISS
VTLEHLNGAYKVEEGDGDIRDPYLKQHLVKTYFVINPKGERRSPQHLFRPRHT
LDGAKMRASVRMTRYLESWGAAKPFAHLHHRDSMTTENGKISTTDVPMGQHNF
QNRTLRTKSQKKRFEEELNERMIQAIDGINAQKQWLKSEDIQRISLLFYNKVL
EKEYRATALPAFKYYVTCACLIFFCIFIVQILVLPKTSVLGISFGAAFLLLAF
ILFVCFAGQLLQCSKKASPLLMWLLKSSGIIANRPWPRISLTIITTAIILMMA
VFNMFFLSDSEETIPPTANTTNTSFSASNNQVAILRAQNLFFLPYFIYSCILG
LISCSVFLRVNYELKMLIMMVALVGYNTILLHTHAHVLGDYSQVLFERPGIWK
DLKTMGSVSLSIFFITLLVLGRQNEYYCRLDFLWKNKFKKEREEIETMENLNR
VLLENVLPAHVAEHFLARSLKNEELYHQSYDCVCVMFASIPDFKEFYTESDVN
KEGLECLRLLNEIIADFDDLLSKPKFSGVEKIKTIGSTYMAATGLSAVPSQEH
SQEPERQYMHIGTMVEFAFALVGKLDAINKHSFNDFKLRVGINHGPVIAGVIG
AQKPQYDIWGNTVNVASRMDSTGVLDKIQVTEETSLVLQTLGYTCTCRGIINV
KGKGDLKTYFVNTEMSRSLSQSNVAS

Fig. 5 ggagcctaccataagcacctcatggaactcgctcttcagcaaacatatcagga
cacctgtaattgcatcaagtcgcggatcaagttggaatttgaaaaacgtcaac
aggagcggcttctgctctccctgctgccggcccacatcgccatggagatgaaa
gcggagatcatccagaggctgcagggccccaaggcgggccagatggagaacac
aaataacttccacaacctgtatgtgaagcggcatacaaacgtgagcatcttat
acgctgacatcgttggctttacccggctggcaagtgactgctccccgggagaa
ctagtccacatgctgaatgagctctttggaaagtttgatcaaattgcaaagga
gaatgaatgcatgagaattaaaattttaggagactgctactactgtgtatctg
gactccctatatctctccctaaccatgccaagaactgtgtgaaatggggctg
gacatgtgtgaagccataagaaagtgagggatgctactggagttgatatcaa
catgcgcgtgggcgtgcattctgggaatgtcctgtgtggcgtgattggtctgc
agaagtggcaatatgatgtgtggtcacatgatgtgaccttggccaaccacatg
gaagctggaggggtccctggacgtgttcacatttcttctgtcaccctggagca
cttgaatggcgcttataaagtggaggagggagatggtgacattagggacccat
atttaaaacagcacctggtgaaaacctactttgtgatcaaccccaagggagaa
cgacggagcccccagcatctcttcagacctcgccacaccttgatggagccaa
aatgagggcctcggtccgcatgacccggtacttggagtcctgggggcagcca
agcccttgcacacctacatcacagggacagcatgaccacagagaacggcaag
atcagcaccacggatgtacccatgggtcagcataatttcaaaatcgcactt
aagaaccaagtcacaaaagaagagatttgaagaagaattgaatgaaaggatga
ttcaagcaattgatgggattaatgcacagaagcaatggctcaagtctgaagac
attcagagaatctcactgcttttctataacaaagtactagaaaagagtaccg
ggccacggcactgccagcgttcaagtattatgtgacttgtgcctgtctcatat
tcttctgcatcttcattgtgcagattctcgtgctgccaaaaacgtctgtcctg
ggcatctcctttggggctgcgtttctcttgctggccttcatcctcttcgtctg
ctttgctggacagcttctgcaatgcagcaaaaaagcctctcccctgctcatgt

Fig. 5-1

```
ggcttttgaagtcctcgggcatcattgccaaccgcccctggccacggatctct
ctcacgatcatcaccacagccatcatattaatgatggccgtgttcaacatgtt
tttcctgagtgactcagaggaaacaatccctccaactgccaacacaacaaaca
caagcttttcagcctcaaataatcaggtggcgattctgcgtgcgcagaattta
ttttcctcccgtactttatctacagctgcattctgggactgatatcctgttc
cgtgttcctgcgggtaaactatgagctgaagatgttgatcatgatggtggcct
tggtgggctacaacaccatcctactccacacccacgcccacgtcctgggcgac
tacagccaggtcttatttgagagaccaggcatttggaaagacctgaagaccat
gggctctgtgtctctctatattcttcatcacactgcttgttctgggtagac
agaatgaatattactgtaggttagacttcttatggaagaacaaattcaaaaaa
gagcgggaggagatagagaccatggagaacctgaaccgcgtgctgctggagaa
cgtgcttcccgcgcacgtggctgagcacttcctggccaggagcctgaagaatg
aggagctataccaccagtcctatgactgcgtctgtgtcatgtttgcctccatt
ccggatttcaaagaattttatacagaatccgacgtgaacaaggagggcttgga
atgccttcggctcctgaacgagatcatcgctgactttgatgatcttctttcca
agccaaaattcagtggagttgaaaagattaagaccattggcagcacatacatg
gcagcaacaggtctgagcgctgtgcccagccaggagcactcccaggagcccga
gcggcagtacatgcacattggcaccatggtggagtttgcttttgccctggtag
ggaagctggatgccatcaacaagcactccttcaacgacttcaaattgcgagtg
ggtattaaccatggacctgtgatagctggtgtgattggagctcagaagccaca
atatgatatctggggcaacactgtcaatgtggccagtaggatggacagcaccg
gagtcctggacaaaatacaggttaccgaggagacgagcctcgtcctgcagacc
ctcggatacacgtgcacctgtcgaggaataatcaacgtgaaaggaaaggggga
cctgaagacgtactttgtaaacacagaaatgtcaaggtcccttcccagagca
acgtggcatcctgaagagtcaccttcattttggcaagaagactgtattttcag
gaaggtatcacacactttctgactgcaacttctgtcccttgttttgatgtgc
gtgctgtctgtcctatggagcctctgcagactcgttctcgtgacccagtggca
taccgtttggtgtctgatgtgtgcccagatcgttctgccacttgcactgtgct
tgctcctaagcaaaagggaaaggagcgcgcgtgatagaagaaaagcactggg
agaactaacagaggagaaaggtgaaacacacacacattcttaaggcaataaaa
ctaggggtgtatattatcttctggtgcatgttcttttctggaaaatatggta
gctcgccaaccgcatctgctcatctgatattcaaacacacagtattcgtgaat
aagttgattctgtccccacgtggactctgtgctcacccattgtctcattgcc
agtggtgtccaagggccccgttgggacccacggctctcgtccctctgctccg
tgtgtctcatgccagcagcacgtcgccatccgtcaccagaattagtcctcaca
gcctaggaccagttttgtatcaaactcgtctgatgttttgatgccatttgtct
tttgtaaagttaattcattaaaagttttatgtactttgatttacagtgcctgt
atcttttatttcctgtcttctttctcctgtggtttgctccagaattaaggtt
tgttttccatccattctcccttttgacacagttgttcagaaagagctctcca
gaagccaatattgagatgtaattcagattaggacacagtgtgtgacgcagata
actggttactcagctccctggaaagcaggcaagcatgttgaatgtatctagtg
gtctgattttaatttgggcatctctagagaacgctttcagggaaaaatacttt
aatagtaaaaagattctctgcgagcaacagtgcccctccgtccactacgctc
ctgtctccaagaatgttttgctagagctaacagacatagactgcaaaagaata
atttggaatcagctatgcaaatcagtctcacaatagcgtgagctaactgagag
aagtactaagacccacaaactgcctgttaagtctgagaaggctaaagaagaca
cacagccaacgttcatgcattttaaagacagaaggccttgaagaatttgttc
ttgtaaatccaacacaagttgtttggtacttttaacataaagaaatcatactt
tgccaaatagtgaaaagtagagcaatcgtgtataagctaatgtttaaaagcaa
aactgcaaattgtagcccagttggtcaaacttgttttctttttataactcatg
gcaggcatctgtaagaagtagagaacccagatgatctcttaggaagccttta
ttcgtgggaactcgaacttgaagcacaagttcctggtttgaatcctggctctg
attttttactggctgtgtgactttgaacacatctcttagtccctcttaggagt
```

Fig. 5-2 actttccttattggcaacttatggaatcgctagtgattaaacgaggcaatgac
tgtgagagagcctggcaggtgcccgtggtacattcacagcacgggcacagct
gctgtgccaggactgtgactcattcccagtaaaaggcacttatcgaagctgat
aaccgtccttcatcaccgaagtgtgagtagagcatgacttatttagtattctg
cctcaatggggaattttttgatcctgtaatcacaactcagcattggccttaat
atacctaaatctccaaaaacagtgattaaagcaagagaattattacaagggct
tttctctttcctctaactcattcttcacggatgccgtagcgtttccgtgagct
caaactggccttggtgtaaaatgtgtaaggatgagcagcaggcgtgcctcgtg
ggttcttcctctgttacatcctgctacactcatctgcaggtcaccttagttca
cctacctgagtgaacaccccagctgggtggtccaccaagttctcataaaca
gagtccctcccattccccacggggtgcaccgaacttgggtttgcgctaaaaa
gaactcaaaaggagaactgtgctctcccaaagccatatcaccagtcttaccaa
acaataggcttttaaaagcactgagtcattgtcagaatccactatgggaagct
ctgtgtgtacctggtcccttctaggtgtggtcccataggagcagccttagcat
cccctgtgaacttatcaaaaatgcaaattctcaggccccaacctgaaggagga
cctgaatttgagatccccggggctggggcccagcacaactgctgtttagtga
acaggttctccaggtgattctgatccctgatcaagcttcagacctccctccct
ccccagtgttttgcaggtgaggaaacaggggcagagtaattcaggcacatgt
gttcagagttccacagttgattagcagttgaggccaggctagaatggaaaact
gcctgttccttgaatctgaagagcattattcctggtcaaagctccttaaagt
tctgggcagctaaaagcatccctgtgagcaaaaatgccaggcagaaaactggc
agtgcacctctcatcagcccaggtcccagtgccattggcttcaagaaaaaaaa
aaatctctcccaatgctctccttaaccttaagtcttacaggaagcctctca
tagaaattgcctccagtccagtttcccaaaaacccagtgttttacatatctg
tttaggagtgtctaagttttgtcatcaatccacgatgttattcttccttccca
actcactgtgctcctaaaggcagcaaccattcatctttcctttgctctggata
caccgaatgaccaggtaacatcatcaggccgggtgcagtggctcctataatcc
cgatatttgggaggccgaggagagaggatcacttaagcccaggagtctgaga
ccagcctgggcaacatagcaagaccccatctctgcaaaaaataagaaaatt
agcttggcatggtggcacgtgcctgtagtcccagctacatgggaggctgaggt
gggaggatcacttgagcccaggaagtccagaacgtagtgagccttgattatac
cactgcactccagcctgggtgacagagcgagactctgtctcag

Fig. 6 atgcggcaccgccgctacctgcgggaccgctccgaggaggcggcgggcggcgg
agacgggctgccgcggtcccgggactggctctacgagtcctactactgcatga
gccagcagcacccgctcatcgtcttcctgctgctcatcgtcatgggctcctgc
ctcgccctgctcgccgtcttcttcgcgctcgggctggaagttgaagaccatgt
ggcgtttctaataacagttccaactgccctggcgattttctttgcgatattta
tcctggtctgcatcgagtctgtgtttaagaagctgctgcgcctcttctcgttg
gtgatatggatatgccttgttgccatgggatacctgttcatgtgttttggagg
caccgtctctccctggaccaggtatcgttcttcctcttcatcatcttcgtgg
tgtacaccatgctgcccttcaacatgcgagacgccatcattgccagcgtcctc
acctcctcctcccacaccatcgtgcttagcgtctgcctgtctgcaacaccggg
aggcaaggagcacctggtctggcagatcctggccaatgtgatcattttcatct
gtgggaacctggcgggagcctaccataagcacctcatggaactcgctcttcag
caaacatatcaggacacctgtaattgcatcaagtcgcggatcaagttggaatt
tgaaaaacgtcaacaggagcggcttctgctctccctgctgccggcccacatcg
ccatggagatgaaagcggagatcatccagaggctgcagggccccaaggcgggc

Fig. 6-1

```
cagatggagaacacaaataacttccacaacctgtatgtgaagcggcatacaaa
cgtgagcatcttatacgctgacatcgttggctttacccggctggcaagtgact
gctccccgggagaactagtccacatgctgaatgagctctttggaaagttTgat
caaattgcaaaggagaatgaatgcatgagaattaaaattttaggagactgcta
ctactgtgtatctggactccctatatctctcctaaccatgccaagaactgtg
tgaaaatggggctggacatgtgtgaagccataaagaaagtgagggatgctact
ggagttgatatcaacatgcgcgtgggcgtgcattctgggaatgtcctgtgtgg
cgtgattggtctgcagaagtggcaatatgatgtgtggtcacatgatgtgacct
tggccaaccacatggaagctggaggggtccctggacgtgttcacatttcttct
gtcacctggagcacttgaatggcgcttataaagtggaggagggagatggtga
cattagggacccatatttaaaacagcacctggtgaaacctactttgtgatca
accccaagggagaacgacggagccccagcatctcttcagacctcgccacacc
cttgatggagccaaaatgagggcctcggtccgcatgacccggtacttggagtc
ctgggggcagccaagccctttgcacacctacatcacagggacagcatgacca
cagagaacggcaagatcagcaccacggatgtacccatgggtcagcataatttt
caaaatcgcaccttaagaaccaagtcacaaaagaagagatttgaagaagaatt
gaatgaaggatgattcaagcaattgatgggattaatgcacagaagcaatggc
tcaagtctgaagacattcagagaatctcactgcttttctataacaaagtacta
gaaaaagagtaccgggccacggcactgccagcgttcaagtattatgtgacttg
tgcctgtctcatattcttctgcatcttcattgtgcagattctcgtgctgccaa
aaacgtctgtcctgggcatctcctttggggctgcgtttctcttgctggccttc
atcctcttcgtctgctttgctggacagcttctgcaatgcagcaaaaaagcctc
tccctgctcatgtggcttttgaagtcctcgggcatcattgccaaccgccct
ggccacggatctctctcacgatcatcaccacagccatcatattaatgatggcc
gtgttcaacatgttttcctgagtgactcagaggaaacaatccctccaactgc
caacacaacaaacacaagcttttcagcctcaaataatcaggtggcgattctgc
gtgcgcagaatttatttttcctcccgtactttatctacagctgcattctggga
ctgatatcctgttccgtgttcctgcgggtaaactatgagctgaagatgttgat
catgatggtggccttggtgggctacaacaccatcctactccacacccacgccc
acgtcctgggcgactacagccaggtcttatttgagagaccaggcatttggaaa
gacctgaagaccatggctctgtgtctctctctatattcttcatcacactgct
tgttctgggtagacagaatgaatattactgtaggttagacttcttatggaaga
acaaattcaaaaagagcgggaggagatagagaccatggagaacctgaaccgc
gtgctgctggagaacgtgcttcccgcgcacgtggctgagcacttcctggccag
gagcctgaagaatgaggagctataccaccagtcctatgactgcgtctgtgtca
tgtttgcctccattccggatttcaaagaattttatacagaatccgacgtgaac
aaggagggcttggaatgccttcggctcctgaacgagatcatcgctgactttga
tgatcttctttccaagccaaaattcagtggagttgaaaagattaagaccattg
gcagcacatacatggcagcaacaggtctgagcgctgtgcccagccaggagcac
tcccaggagcccgagcggcagtacatgcacattggcaccatggtggagtttgc
ttttgccctggtagggaagctggatgccatcaacaagcactccttcaacgact
tcaaattgcgagtgggtattaaccatggacctgtgatagctggtgtgattgga
gctcagaagccacaatatgatatctggggcaacactgtcaatgtggccagtag
gatggacagcaccggagtcctggacaaaatacaggttaccgaggagacgagcc
tcgtcctgcagaccctcggatacacgtgcacctgtcgaggaataatcaacgtg
aaaggaaaggggacctgaagacgtactttgtaaacacagaaatgtcaaggtc
cctttcccagagcaacgtggcatcctgaagagtcaccttcatttggcaagaa
gactgtattttcaggaaggtatcacacactttctgactgcaacttctgtccct
tgttttgatgtgcgtgctgtctgtcctatggagcctctgcagactcgttctc
gtgacccagtggcataccgtttggtgtctgatgtgtgcccagatcgttctgcc
acttgcactgtgcttgctcctaagcaaaagggaaaaggagcgcgcgtgataga
agaaaagcactgggagaactaacagaggagaaaggtgaaacacacacacattc
ttaaggcaataaaactagggggtgtatattatcttctggtgcatgttctttc
```

Fig. 6-2

```
tggaaaatatggtagctcgccaaccgcatctgctcatctgatattcaaacaca
cagtattcgtgaataagttgattctgtcccccacgtggactctgtgctcaccc
attgtctcattgccagtggtgtccaagggcccccgttgggacccacggctctc
gtccctctgctccgtgtgtctcatgccagcagcacgtcgccatccgtcaccag
aattagtcctcacagcctaggaccagttttgtatcaaactcgtctgatgtttt
gatgccatttgtctttgtaaagttaattcattaaaagttttatgtactttga
tttacagtgcctgtatctttttattttcctgtcttctttctcctgtggtttgct
ccagaattaaggtttgttttccatccattctcccttttgacacagttgtttca
gaaagagctctccagaagccaatattgagatgtaattcagattaggacacagt
gtgtgacgcagataactggttactcagctccctggaaagcaggcaagcatgtt
gaatgtatctagtggtctgatttaatttgggcatctctagagaacgctttca
gggaaaaatactttaatagtaaaaagattctctgcgagcaacagtgcccctc
cgtccactacgctcctgtctccaagaatgtttgctagagctaacagacatag
actgcaaagaataatttggaatcagctatgcaaatcagtctcacaatagcgt
gagctaactgagagaagtactaagacccacaaactgcctgttaagtctgagaa
ggctaaagaagacacacagccaacgttcatgcatttttaaagacagaaggcct
tgaagaatttgttcttgtaaatccaacacaagttgtttggtacttttaacata
aagaaatcatactttgccaaatagtgaaaagtagagcaatcgtgtataagcta
atgtttaaaagcaaaactgcaaattgtagcccagttggtcaaacttgttttct
ttttataactcatggcaggcatctgtaagaagtagagaacccagatgatctct
taggaagcctttattcgtgggaactcgaacttgaagcacaagttcctggttt
gaatcctggctctgattttttactggctgtgtgactttgaacacatctcttag
tccctcttaggagtactttccttattggcaacttatggaatcgctagtgatta
aacgaggcaatgactgtgagagagcctggcaggtgcccgtggtacattcaca
gcacgggcacagctgctgtgccaggactgtgactcattcccagtaaaaggcac
ttatcgaagctgataaccgtccttcatcaccgaagtgtgagtagagcatgact
tatttagtattctgcctcaatggggaattttttgatcctgtaatcacaactca
gcattggccttaatatacctaaatctccaaaaacagtgattaaagcaagagaa
ttattacaagggcttttctctttcctctaactcattcttcacggatgccgtag
cgtttccgtgagctcaaactggccttggtgtaaaatgtgtaaggatgagcagc
aggcgtgcctcgtgggttcttcctctgttacatcctgctacactcatctgcag
gtcaccttagttcacctaccctgagtgaacaccccagctgggtggtccacca
agttctcataaacagagtccctcccattccccacggggtgcaccgaacttgg
gtttgcgctaaaaagaactcaaaggagaactgtgctctcccaaagccatatc
accagtcttaccaaacaataggctttaaaagcactgagtcattgtcagaatc
cactatgggaagctctgtgtgtacctggtcccttctaggtgtggtcccatagg
agcagccttagcatcccctgtgaacttatcaaaaatgcaaattctcaggcccc
aacctgaaggaggaccctgaatttgagatccccggggctggggcccagcacaa
ctgctgtttagtgaacaggttctccaggtgattctgatccctgatcaagcttc
agacctccctccctcccagtgttttgcaggtgaggaaacaggggcagagta
attcaggcacatgtgttcagagttccacagttgattagcagttgaggccaggc
tagaatggaaaactgcctgttccttgaatctgaaagagcattattcctggtca
aagctccttaaagttctgggcagctaaagcatccctgtgagcaaaaatgcca
ggcagaaaactggcagtgcacctctcatcagcccaggtcccagtgccattggc
ttcaagaaaaaaaaaatctctccccaatgctctccttaacctttaagtctta
caggaagcctctcatagaaattgcctccagtccagtttcccaaaaacccagt
gttttacatatctgtttaggagtgtctaagttttgtcatcaatccacgatgtt
attcttccttcccaactcactgtgctcctaaaggcagcaaccattcatctttc
ctttgctctggatacaccgaatgaccaggtaacatcatcaggccgggtgcagt
ggctcctataatcccgatattttgggaggccgaggagagaggatcacttaagc
ccaggagtctgagaccagcctgggcaacatagcaagacccccatctctgcaaa
aaaataagaaaattagcttggcatggtggcacgtgcctgtagtcccagctaca
tgggaggctgaggtgggaggatcacttgagcccaggaagtccagaacgtagtg
```

Fig. 6-3 agccttgattataccactgcactccagcctgggtgacagagcgagactctgtc
tcag

Fig. 7

MRRRRYLRDRAEAAAAAAAGGGEGLQRSRDWLYESYYCMSQQHPLIVFLLLIV
MGACLALLAVFFALGLEVEDHVAFLITVPTALAIFFAIFILVCIESVFKKLLR
VFSLVIWICLVAMGYLFMCFGGTVSAWDQVSFFLFIIFVVYTMLPFNMRDAII
ASILTSSSHTIVLSVYLSATPGAKEHLFWQILANVIIFICGNLAGAYHKHLME
LALQQTYRDTCNCIKSRIKLEFEKRQQERLLLSLLPAHIAMEMKAEIIQRLQG
PKAGQMENTNNFHNLYVKRHTNVSILYADIVGFTRLASDCSPGELVHMLNELF
GKFDQIAKENECMRIKILGDCYYCVSGLPISLPNHAKNCVKMGLDMCEAIKKV
RDATGVDINMRVGVHSGNVLCGVIGLQKWQYDVWSHDVTLANHMEAGGVPGRV
HISSVTLEHLNGAYKVEEGDGEIRDPYLKQHLVKTYFVINPKGERRSPQHLFR
PRHTLDGAKMRASVRMTRYLESWGAAKPFAHLHHRDSMTTENGKISTTDVPMG
QHNFQNRTLRTKSQKKRFEEELNERMIQAIDGINAQKQWLKSEDIQRISLLFY
NKNIEKEYRATALPAFKYYVTCACLIFLCIFIVQILVLPKTSILGFSFGAAFL
SLIFILFVCFAGQLLQCSKKASTSLMWLLKSSGIIANRPWPRISLTIVTTAII
LTMAVFNMFFLSNSEETTLPTANTSNANVSVPDNQASILHARNLFFLPYFIYS
CILGLISCSVFLRVNYELKMLIMMVALVGYNTILLHTHAHVLDAYSQVLFQRP
GIWKDLKTMGSVSLSIFFITLLVLGRQSEYYCRLDFLWKNKFKKEREEIETME
NLNRVLLENVLPAHVAEHFLARSLKNEELYHQSYDCVCVMFASIPDFKEFYTE
SDVNKEGLECLRLLNEIIADFDDLLSKPKFSGVEKIKTIGSTYMAATGLSAIP
SQEHAQEPERQYMHIGTMVEFAYALVGKLDAINKHSFNDFKLRVGINHGPVIA
GVIGAQKPQYDIWGNTVNVASRMDSTGVLDKIQVTEETSLILQTLGYTCTCRG
IINVKGKGDLKTYFVNTEMSRSLSQSNLAS

Fig. 8

BLASTP - alignment of 129_protein against swiss|P26769|CYA2_RAT

ADENYLATE CYCLASE, TYPE II (EC 4.6.1.1) (ATP PYROPHOSPHATE-LYASE) (ADENYLYL
CYCLASE).//:trembl|M80550|RNADNCYII 1 product: "adenylyl cyclase type II";
Rat adenylyl cyclase mRNA, complete cds. //:gp|M80550|202752 product:
"adenylyl cyclase type II"; Rat adenylyl cyclase mRNA, complete cds.

This hit is scoring at : 0.0 (expectation value)
Alignment length (overlap) : 1090
Identities : 95 %
Scoring matrix : BLOSUM62 (used to infer consensus pattern)
Database searched : nrdb

```
Q:   1 MRHRRYLRDRSEEAA----GGGDGLPRSRDWLYESYYCMSQQHPLIVFLLLIVMGSCLAL
         MR.RRYLRDR:E.AA     GGG:GL.RSRDWLYESYYCMSQQHPLIVFLLLIVMG:CLAL
H:   1 MRRRRYLRDRAEAAAAAAAAGGGEGLQRSRDWLYESYYCMSQQHPLIVFLLLIVMGACLAL

LAVFFALGLEVEDHVAFLITVPTALAIFFAIFILVCIESVFKKLLRLFSLVIWICLVAMG
       LAVFFALGLEVEDHVAFLITVPTALAIFFAIFILVCIESVFKKLL.:FSLVIWICLVAMG
       LAVFFALGLEVEDHVAFLITVPTALAIFFAIFILVCIESVFKKLLRVFSLVIWICLVAMG

YLFMCFGGTVSPWDQVSFFLFIIFVVYTMLPFNMRDAIIASVLTSSSHTIVLSVCLSATP
       YLFMCFGGTVS.WDQVSFFLFIIFVVYTMLPFNMRDAIIAS:LTSSSHTIVLSV LSATP
       YLFMCFGGTVSAWDQVSFFLFIIFVVYTMLPFNMRDAIIASILTSSSHTIVLSVYLSATP

GGKEHLVWQILANVIIFICGNLAGAYHKHLMELALQQTYQDTCNCIKSRIKLEFEKRQQE
       G.KEHL.WQILANVIIFICGNLAGAYHKHLMELALQQTY:DTCNCIKSRIKLEFEKRQQE
       GAKEHLFWQILANVIIFICGNLAGAYHKHLMELALQQTYRDTCNCIKSRIKLEFEKRQQE

RLLLSLLPAHIAMEMKAEIIQRLQGPKAGQMENTNNFHNLYVKRHTNVSILYADIVGFTR
       RLLLSLLPAHIAMEMKAEIIQRLQGPKAGQMENTNNFHNLYVKRHTNVSILYADIVGFTR
       RLLLSLLPAHIAMEMKAEIIQRLQGPKAGQMENTNNFHNLYVKRHTNVSILYADIVGFTR
```

Fig. 8-1

```
LASDCSPGELVHMLNELFGKFDQIAKENECMRIKILGDCYYCVCVSGLPISLPNHAKNCVKM
LASDCSPGELVHMLNELFGKFDQIAKENECMRIKILGDCYYCVCVSGLPISLPNHAKNCVKM
LASDCSPGELVHMLNELFGKFDQIAKENECMRIKILGDCYYCVCVSGLPISLPNHAKNCVKM

GLDMCEAIKKVRDATGVDINMRVGVHSGNVLCGVIGLQKWQYDVWSHDVTLANHMEAGGV
GLDMCEAIKKVRDATGVDINMRVGVHSGNVLCGVIGLQKWQYDVWSHDVTLANHMEAGGV
GLDMCEAIKKVRDATGVDINMRVGVHSGNVLCGVIGLQKWQYDVWSHDVTLANHMEAGGV

PGRVHISSVTLEHLNGAYKVEEGDGDIRDPYLKQHLVKTYFVINPKGERRSPQHLFRPRH
PGRVHISSVTLEHLNGAYKVEEGDG:IRDPYLKQHLVKTYFVINPKGERRSPQHLFRPRH
PGRVHISSVTLEHLNGAYKVEEGDGEIRDPYLKQHLVKTYFVINPKGERRSPQHLFRPRH

TLDGAKMRASVRMTRYLESWGAAKPFAHLHHRDSMTTENGKISTTDVPMGQHNFQNRTLR
TLDGAKMRASVRMTRYLESWGAAKPFAHLHHRDSMTTENGKISTTDVPMGQHNFQNRTLR
TLDGAKMRASVRMTRYLESWGAAKPFAHLHHRDSMTTENGKISTTDVPMGQHNFQNRTLR

TKSQKKRFEEELNERMIQAIDGINAQKQWLKSEDIQRISLLFYNKVLEKEYRATALPAFK
TKSQKKRFEEELNERMIQAIDGINAQKQWLKSEDIQRISLLFYNK :EKEYRATALPAFK
TKSQKKRFEEELNERMIQAIDGINAQKQWLKSEDIQRISLLFYNKNIEKEYRATALPAFK

YYVTCACLIFFCIFFCIFIVQILVLPKTSVLGISFGAAFLLLAFILFVCFAGQLLQCSKKASPL
YYVTCACLIF.CIFIVQILVLPKTS:LG.SFGAAFL L.FILFVCFAGQLLQCSKKAS.
YYVTCACLIFLCIFIVQILVLPKTSILGFSFGAAFLSLIFILFVCFAGQLLQCSKKASTS

LMWLLKSSGIIANRPWPRISLTITTAIILMMAVFNMFFLSDSEETIPPTANTTNTSFSA
LMWLLKSSGIIANRPWPRISLTI:TTAIIL.MAVFNMFFLS:SEET. PTANT:N.:.S.
LMWLLKSSGIIANRPWPRISLTIVTTAIILTMAVFNMFFLSNSEETTLPTANTSNANVSV

SNNQVAILRAQNLFFLPYFIYSCILGLISCSSVFLRVNYELKMLIMMVALVGYNTILLHTH
:NQ.:IL.A:NLFFLPYFIYSCILGLISCSSVFLRVNYELKMLIMMVALVGYNTILLHTH
PDNQASILHARNLFFLPYFIYSCILGLISCSSVFLRVNYELKMLIMMVALVGYNTILLHTH
```

Fig. 8-2

```
AHVLGDYSQVLFERPGIWKDLKTMGSVSLSIFFITLLVLGRQNEYYCRLDFLWKNKFKKE
AHVL.YSQVLF:RPGIWKDLKTMGSVSLSIFFITLLVLGRQ:EYYCRLDFLWKNKFKKE
AHVLDAYSQVLFQRPGIWKDLKTMGSVSLSIFFITLLVLGRQSEYYCRLDFLWKNKFKKE

REEIETMENLNRVLLENVLPAHVAEHFLARSLKNEELYHQSYDCVCVMFASIPDFKEFYT
REEIETMENLNRVLLENVLPAHVAEHFLARSLKNEELYHQSYDCVCVMFASIPDFKEFYT
REEIETMENLNRVLLENVLPAHVAEHFLARSLKNEELYHQSYDCVCVMFASIPDFKEFYT

ESDVNKEGLECLRLLNEIIADFDDLLSKPKFSGVEKIKTIGSTYMAATGLSAVPSQEHSQ
ESDVNKEGLECLRLLNEIIADFDDLLSKPKFSGVEKIKTIGSTYMAATGLSA:PSQEH:Q
ESDVNKEGLECLRLLNEIIADFDDLLSKPKFSGVEKIKTIGSTYMAATGLSAIPSQEHAQ

EPERQYMHIGTMVEFAFALVGKLDAINKHSFNDFKLRVGINHGPVIAGVIGAQKPQYDIW
EPERQYMHIGTMVEFA:ALVGKLDAINKHSFNDFKLRVGINHGPVIAGVIGAQKPQYDIW
EPERQYMHIGTMVEFAYALVGKLDAINKHSFNDFKLRVGINHGPVIAGVIGAQKPQYDIW

GNTVNVASRMDSTGVLDKIQVTEETSLVLQTLGYTCTCRGIINVKGKGDLKTYFVNTEMS
GNTVNVASRMDSTGVLDKIQVTEETSL:LQTLGYTCTCRGIINVKGKGDLKTYFVNTEMS
GNTVNVASRMDSTGVLDKIQVTEETSLILQTLGYTCTCRGIINVKGKGDLKTYFVNTEMS

RSLSQSNVAS    1086
RSLSQSN:AS
RSLSQSNLAS    1090
```

Prosite guanylate cyclases signature
Guanylate cyclases proteins BLOCKS

Fig. 9

Prosite search results

| Access# | From->To | Name | Doc# |
|---|---|---|---|
| PS00452 | 389->413 | GUANYLATE_CYCLASES | PDOC00425 |
| PS00452 | 1004->1028 | GUANYLATE_CYCLASES | PDOC00425 |

Fig. 10

Transmembrane Helix

| | | |
|---|---|---|
| inside | 1 | 39 |
| TMhelix | 40 | 62 |
| outside | 63 | 70 |
| TMhelix | 71 | 93 |
| inside | 94 | 99 |
| TMhelix | 100 | 122 |
| outside | 123 | 130 |
| TMhelix | 131 | 149 |
| inside | 150 | 155 |
| TMhelix | 156 | 178 |
| outside | 179 | 181 |
| TMhelix | 182 | 200 |
| inside | 201 | 594 |
| TMhelix | 595 | 617 |
| outside | 618 | 620 |
| TMhelix | 621 | 643 |
| inside | 644 | 674 |
| TMhelix | 675 | 697 |
| outside | 698 | 728 |
| TMhelix | 729 | 751 |
| inside | 752 | 757 |
| TMhelix | 758 | 780 |
| outside | 781 | 798 |
| TMhelix | 799 | 817 |
| inside | 818 | 1086 |

Fig. 11

BLOCKS search results

| AC# | Description | | Strength | Score |
|---|---|---|---|---|
| BL00452C | Guanylate cyclases proteins. | | 1280 | 1417 |
| AA# | 929 | VEKIKTIGSTYMAATGL | | |
| BL00452D | Guanylate cyclases proteins. | | 1208 | 1385 |
| AA# | 1002 | AGVIGAQKPQYDIWGNTVNVASRMDSTGVLDKIQVTEETSLVL | | |
| BL00452B | Guanylate cyclases proteins. | | 1226 | 1381 |
| AA# | 275 | LYVKRHTNVSILYADIVGFTRLASDCSPGELVHMLNELFGKFD | | |
| BL00452A | Guanylate cyclases proteins. | | 1132 | 1297 |
| AA# | 230 | EKRQQERLLLSLLPAHIAMEMK | | |

Fig. 12

HMMPFAM - alignment of 129L_protein against pfam|hmm|guanylate_cyc

Adenylate and Guanylate cyclase catalyt

This hit is scoring at : 240.3; Expect = 2.7e-68
Scoring matrix : BLOSUM62 (used to infer consensus pattern)

```
Q: 276 LYVKRHTNVSILYADIVGFTRLASDCS----PGELVHMLNELFGKFDQIAKEN--ECMRI
       :Y:.:R:..V::IL:ADIVGFT.L:S  S    P E:V.:LNELF :FD:..E:   .::I
H:   1 vyaerydeVtilFaDIvgFTalssrhssNngPeevvrlLNelftrFDelvdehkfgvyKi KILGDCYYCVSGLPIS---------------------LPNHAKNCVKMGLDMCEAIKKVRDATG
       K.:GD.Y...SGLP :                     HA.....:L M.EA::V.
       KTiGDaYMaasGlppaakakqtssKlaeeldedsaaHaakiadfALamvealqevnvght V--D---------INMRVGVHSGNVLCGVIG--LQKWQYDVWSHDVTLANHMEAGGVPG-RV
        ::R:G:H:G V:.GVIG     ::R:G:H:G V:.GVIG  :: :YDVW...V.:A:.ME: GVPG ::
       eggpPtvLyrglqlRigIHtGpVvaGviGgaskrprYdvwGdTVNvASRmEStGvpgekI HISSVTLEHLNGAYKVEEG-----DGDIRDPYLKQH-LVKTYFVIN     460
       H:S. T..L. .:                G:::.      .:::TYF:.
       hVsestyrlLkelesfqefaleprgevsvkGkgkpGaietYfLkg       226
```

Fig. 12-1

This hit is scoring at :: 333.7; Expect = 2.1e-96
Scoring matrix : BLOSUM62 (used to infer consensus pattern)

```
Q:  873 LYHQSYDCVCVMFASIPDFKEFYTESDVNKEGLECLRLLNEIIADFDDLLSKPKFsGVEK
        :Y ::YD V.::FA.I .F::::: N. E.:RLLNE::. FD:L::. KF GV K
H:    1 vyaerydeVtilFaDIvgFTalssrhssNngPeevvrlLNelftrFDelvdehkf.gvyK IKTIGSTYMAATGLSAVP------SQE-HSQEPERQYMHIGTMVEFAFALVGKLDAINKHS
        IKTIG..YMAA:GL..... S: . :E .:H..:.:FA.A:V .L..:N
        iKTiGDaYMaasGlppaakakgtssKlaeeldedsaaHaakiadfALamvealqevnvgh FN--D-------FKLRVGINHGPVIAGVIG--AQKPQYDIWGNTVNVASRMDSTGVLD-K
        . :LR:GI: GPV:AGVIG :::P:YD:WG:TVNVASRM:STGV . K
        teggpPtvLyrglqlRiglHtGPVvaGviGgaskrpryDvwGdTVNvASRmEStGvpgek IQVTEETSLVLQTLG-YTCTC----RGIINVKGK---GDLKTYFVNT          1073
        I.V:E.T :L::L :. RG ::VKGK G ::TYF::
        IhVsestyrlLkelesfqefalepprgevsvkGkgkpGaietYfLkg           226
```

Fig. 13

BLASTP - alignment of 129L_protein against pdb|1CJK-B adenylate cyclase, type vfragment: c1a domain of adenylyl cyclase; (protein vc1)Mutantadenylate cyclase, type iifragment: c2a domain of adenylyl cyclase; (protein iic2, atp pyrophosphate-lyase, adenylyl cyclase)guanine nucleotide-binding protein g(s)fragment: trypsinized fragment; (alpha subunit of adenylate cyclase-stimulating g alpha protein, gs-alpha, protein gsa)Mutant This hit is scoring at : 5e-104 (expectation value)
Alignment length (overlap) : 201
Identities : 93 %
Scoring matrix : BLOSUM62 (used to infer consensus pattern)
Database searched : nrdb

```
Q:  873 LYHQSYDCVCVMFASIPDFKEFYTESDVNKEGLECLRLLNEIIADFDDLLSKPKFSGVEK
        LYHQSYDCVCVMFASIPDFKEFYTESDVNKEGLECLRLLNEIIADFDDLLSKPKFSGVEK
H:    1 LYHQSYDCVCVMFASIPDFKEFYTESDVNKEGLECLRLLNEIIADFDDLLSKPKFSGVEK

IKTIGSTYMAATGLSAVPSQEHSQEPERQYMHIGTMVEFAFALVGKLDAINKHSFNDFKL
        IKTIGSTYMAATGLSA            RQYMHIGTMVEFA:ALVGKLDAINKHSFNDFKL
        IKTIGSTYMAATGLSA------------RQYMHIGTMVEFAYALVGKLDAINKHSFNDFKL

RVGINHGPVIAGVIGAQKPQYDIWGNTVNVASRMDSTGVLDKIQVTEETSLVLQTLGYTC
        RVGINHGPVIAGVIGAQKPQYDIWGNTVNVASRMDSTGVLDKIQVTEETSL:LQTLGYTC
        RVGINHGPVIAGVIGAQKPQYDIWGNTVNVASRMDSTGVLDKIQVTEETSLILQTLGYTC

TCRGIINVKGKGDLKTYFVNT 1073
        TCRGIINVKGKGDLKTYFVNT
        TCRGIINVKGKGDLKTYFVNT  190
```

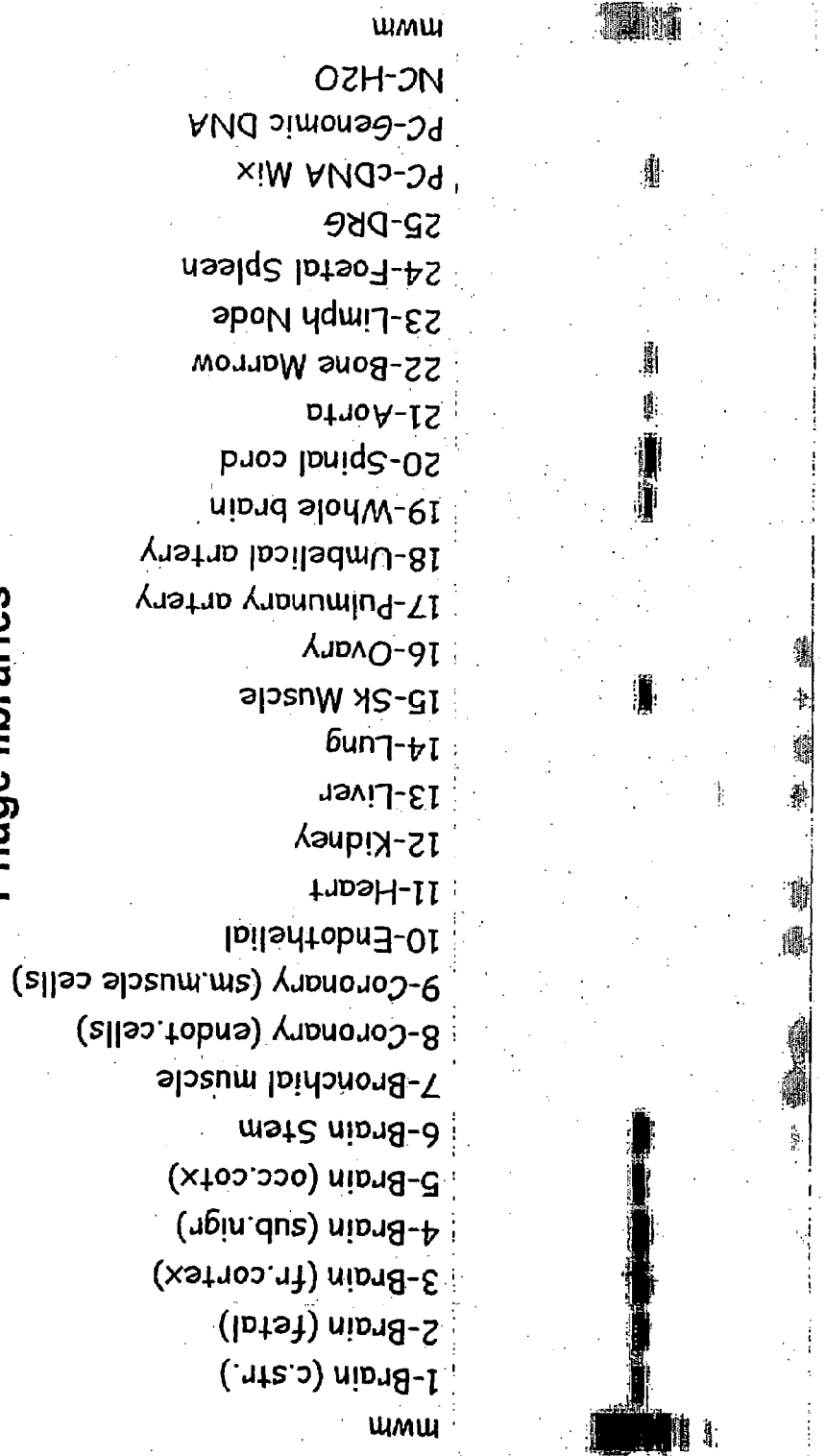
Fig. 14. Relative expression of adenylate cyclase in various human tissues

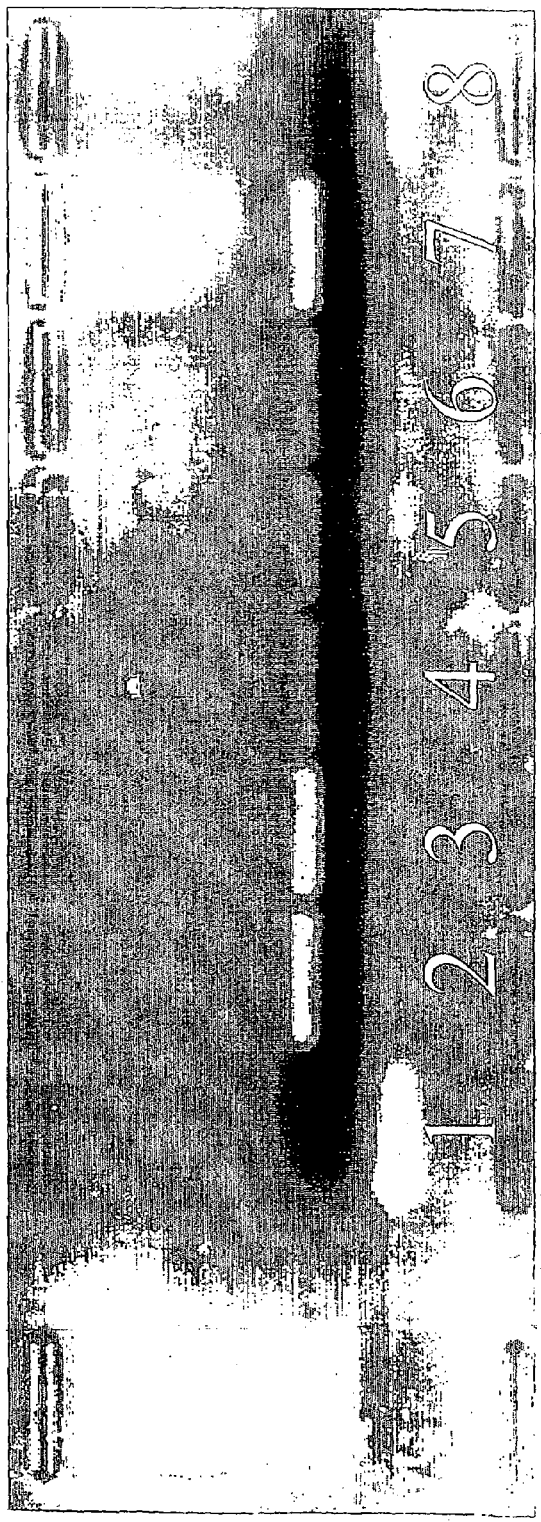
Fig. 15: Relative expression of adenylate cyclase in various human tissues (RT-PCR)

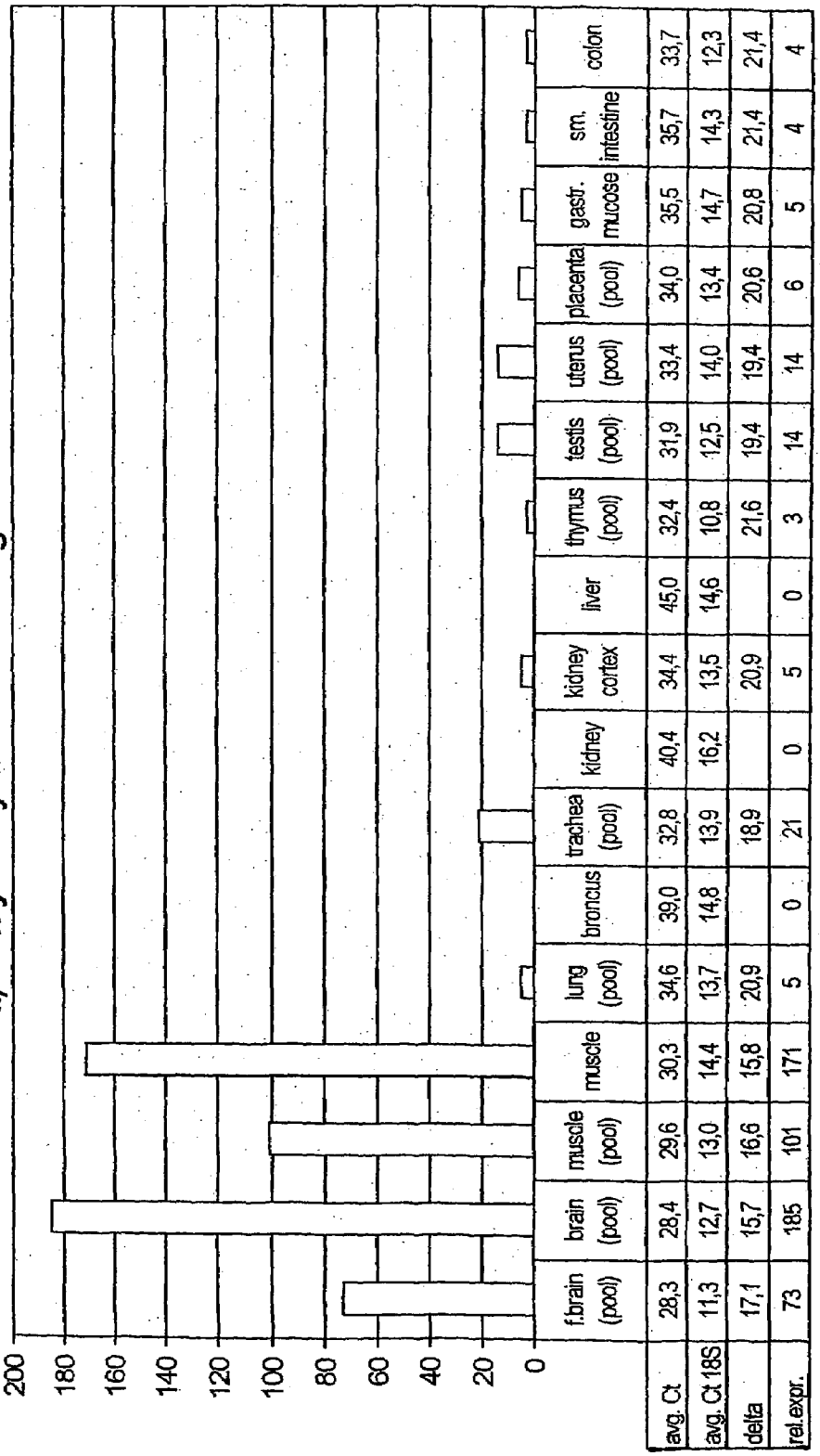
Fig. 16: Relative expression of adenylate cyclase in various human tissues (Taqman)

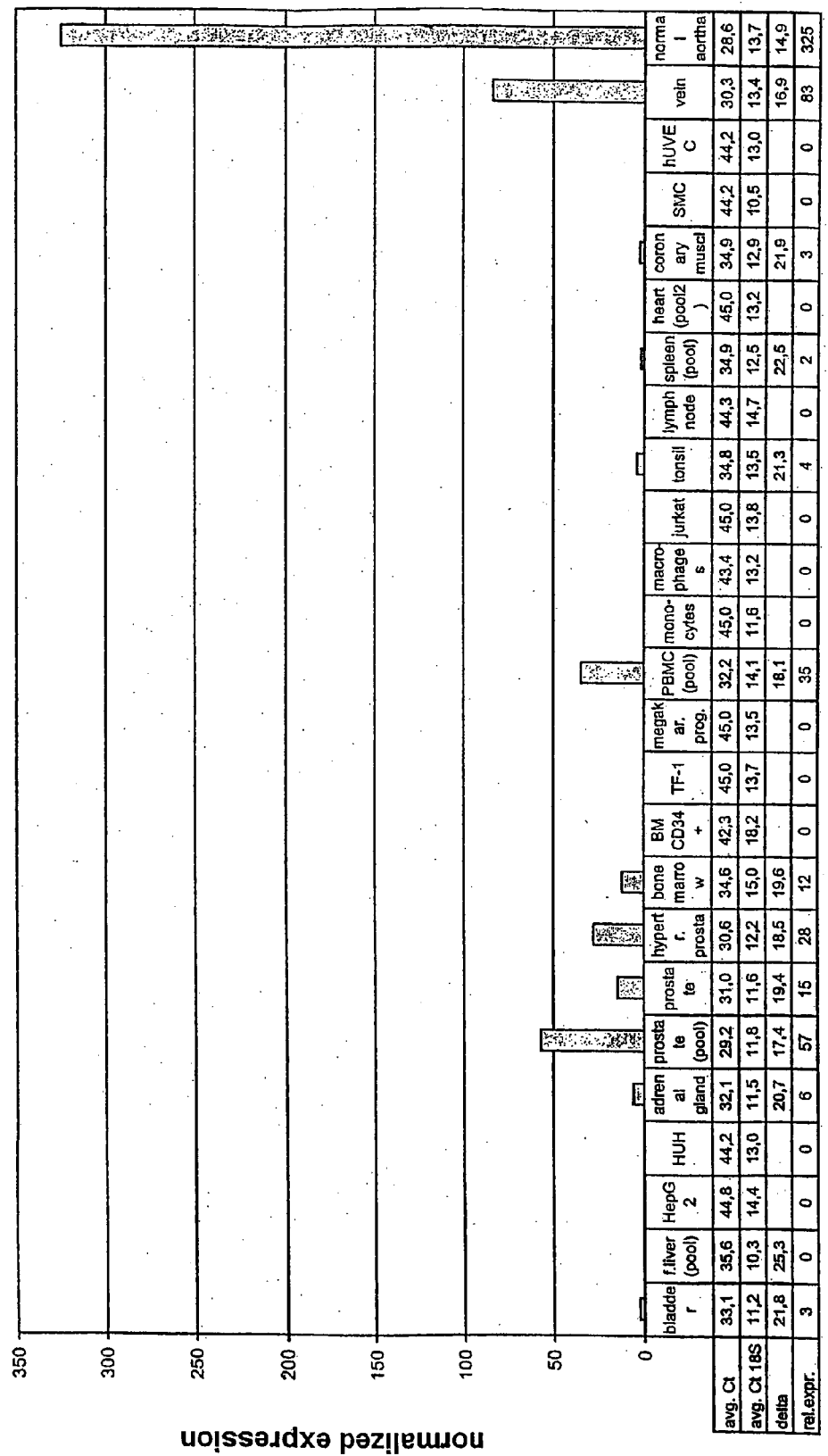
Fig. 16-1 b) Adenylate Cyclase - Human CV Panel

```
                              SEQUENCE LISTING

<160> NUMBER OF SEQ ID NOS: 7

<210> SEQ ID NO 1
<211> LENGTH: 2664
<212> TYPE: DNA
<213> ORGANISM: Homo sapiens

<400> SEQUENCE: 1
ggagcctacc ataagcacct catggaactc gctcttcagc aaacatatca ggacacctgt      60
aattgcatca agtcgcggat caagttggaa tttgaaaaac gtcaacagga gcggcttctg     120
ctctccctgc tgccggccca catcgccatg gagatgaaag cggagatcat ccagaggctg     180
cagggcccca aggcgggcca gatggagaac acaaataact ccacaaccct gtatgtgaag     240
cggcatacaa acgtgagcat cttatacgct gacatcgttg gctttacccg gctggcaagt     300
gactgctccc cgggagaact agtccacatg ctgaatgagc tctttggaaa gtttgatcaa     360
attgcaaagg agaatgaatg catgagaatt aaaattttag gagactgcta ctactgtgta     420
tctggactcc ctatatctct ccctaaccat gccaagaact gtgtgaaaat ggggctggac     480
atgtgtgaag ccataaagaa agtgagggat gctactggag ttgatatcaa catgcgcgtg     540
ggcgtgcatt ctgggaatgt cctgtgtggc gtgattggtc tgcagaagtg gcaatatgat     600
gtgtggtcac atgatgtgac cttggccaac cacatggaag ctggagggt ccctggacgt     660 gttcacattt cttctgtcac cctggagcac ttgaatggcg cttataaagt ggaggaggga     720
gatggtgaca ttagggaccc atatttaaaa cagcacctgg tgaaaaccta ctttgtgatc     780 aacccccaagg gagaacgacg gagcccccag catctcttca gacctcgcca caccttgat    840 ggagccaaaa tgagggcctc ggtccgcatg acccggtact tggagtcctg ggggcagcc     900 aagccctttg cacacctaca tcacagggac agcatgacca cagagaacgg caagatcagc     960
accacggatg tacccatggg tcagcataat tttcaaaatc gcaccttaag aaccaagtca    1020
caaaagaaga gatttgaaga agaattgaat gaaaggatga ttcaagcaat tgatgggatt    1080
aatgcacaga agcaatggct caagtctgaa gacattcaga gaatctcact gcttttctat    1140
aacaaagtac tagaaaaaga gtaccgggcc acggcactgc cagcgttcaa gtattatgtg    1200
```

-continued

```
acttgtgcct gtctcatatt cttctgcatc ttcattgtgc agattctcgt gctgccaaaa    1260
acgtctgtcc tgggcatctc ctttggggct gcgtttctct tgctggcctt catcctcttc    1320
gtctgctttg ctggacagct tctgcaatgc agcaaaaaag cctctcccct gctcatgtgg    1380
cttttgaagt cctcgggcat cattgccaac cgcccctggc cacggatctc tctcacgatc    1440
atcaccacag ccatcatatt aatgatggcc gtgttcaaca tgttttttcct gagtgactca    1500 gaggaaacaa tccctccaac tgccaacaca acaaacacaa gcttttcagc ctcaaataat    1560
caggtggcga ttctgcgtgc gcagaattta ttttcctcc cgtactttat ctacagctgc      1620
attctgggac tgatatcctg ttccgtgttc ctgcgggtaa actatgagct aagatgttg      1680 atcatgatgg tggccttggt gggctacaac accatcctac tccacaccca cgcccacgtc    1740
ctgggcgact acagccaggt cttatttgag agaccaggca tttggaaaga cctgaagacc    1800
atgggctctg tgtctctctc tatattcttc atcacactgc ttgttctggg tagacagaat    1860
gaatattact gtaggttaga cttcttatgg aagaacaaat tcaaaaaaga gcgggaggag    1920
atagagacca tggagaacct gaaccgcgtg ctgctggaga acgtgcttcc cgcgcacgtg    1980
gctgagcact tcctggccag gagcctgaag aatgaggagc tataccacca gtcctatgac    2040
tgcgtctgtg tcatgtttgc ctccattccg gatttcaaag aatttttatac agaatccgac    2100 gtgaacaagg agggcttgga atgccttcgg ctcctgaacg agatcatcgc tgactttgat    2160
gatcttcttt ccaagccaaa attcagtgga gttgaaaaga ttaagaccat tggcagcaca    2220
tacatggcag caacaggtct gagcgctgtg cccagccagg agcactccca ggagcccgag    2280
cggcagtaca tgcacattgg caccatggtg gagtttgctt ttgccctggt agggaagctg    2340
gatgccatca caagcactc cttcaacgac ttcaaattgc gagtgggtat taaccatgga    2400
cctgtgatag ctggtgtgat tggagctcag aagccacaat atgatatctg gggcaacact    2460
gtcaatgtgg ccagtaggat ggacagcacc ggagtcctgg acaaaataca ggttaccgag    2520
gagacgagcc tcgtcctgca gaccctcgga tacacgtgca cctgtcgagg aataatcaac    2580
gtgaaaggaa aggggaccct gaagacgtac tttgtaaaca cagaaatgtc aaggtcccttt   2640 tcccagagca acgtggcatc ctga                                            2664
```

```
<210> SEQ ID NO 2
<211> LENGTH: 5873
<212> TYPE: DNA
<213> ORGANISM: Homo sapiens
<220> FEATURE:
<221> NAME/KEY: CDS
<222> LOCATION: (1)..(2664)
<223> OTHER INFORMATION:

<400> SEQUENCE: 2
```

```
gga gcc tac cat aag cac ctc atg gaa ctc gct ctt cag caa aca tat        48
Gly Ala Tyr His Lys His Leu Met Glu Leu Ala Leu Gln Gln Thr Tyr
1               5                   10                  15 cag gac acc tgt aat tgc atc aag tcg cgg atc aag ttg gaa ttt gaa        96
Gln Asp Thr Cys Asn Cys Ile Lys Ser Arg Ile Lys Leu Glu Phe Glu
            20                  25                  30 aaa cgt caa cag gag cgg ctt ctg ctc tcc ctg ctg ccg gcc cac atc      144
Lys Arg Gln Gln Glu Arg Leu Leu Leu Ser Leu Leu Pro Ala His Ile
        35                  40                  45 gcc atg gag atg aaa gcg gag atc atc cag agg ctg cag ggc ccc aag      192
Ala Met Glu Met Lys Ala Glu Ile Ile Gln Arg Leu Gln Gly Pro Lys
    50                  55                  60
```

|  |  |
|---|---:|
| gcg ggc cag atg gag aac aca aat aac ttc cac aac ctg tat gtg aag<br>Ala Gly Gln Met Glu Asn Thr Asn Asn Phe His Asn Leu Tyr Val Lys<br>65                       70                       75                     80 | 240 |
| cgg cat aca aac gtg agc atc tta tac gct gac atc gtt ggc ttt acc<br>Arg His Thr Asn Val Ser Ile Leu Tyr Ala Asp Ile Val Gly Phe Thr<br>                     85                     90                     95 | 288 |
| cgg ctg gca agt gac tgc tcc ccg gga gaa cta gtc cac atg ctg aat<br>Arg Leu Ala Ser Asp Cys Ser Pro Gly Glu Leu Val His Met Leu Asn<br>            100                     105                   110 | 336 |
| gag ctc ttt gga aag ttt gat caa att gca aag gag aat gaa tgc atg<br>Glu Leu Phe Gly Lys Phe Asp Gln Ile Ala Lys Glu Asn Glu Cys Met<br>            115                     120                   125 | 384 |
| aga att aaa att tta gga gac tgc tac tac tgt gta tct gga ctc cct<br>Arg Ile Lys Ile Leu Gly Asp Cys Tyr Tyr Cys Val Ser Gly Leu Pro<br>130                       135                     140 | 432 |
| ata tct ctc cct aac cat gcc aag aac tgt gtg aaa atg ggg ctg gac<br>Ile Ser Leu Pro Asn His Ala Lys Asn Cys Val Lys Met Gly Leu Asp<br>145                       150                     155                   160 | 480 |
| atg tgt gaa gcc ata aag aaa gtg agg gat gct act gga gtt gat atc<br>Met Cys Glu Ala Ile Lys Lys Val Arg Asp Ala Thr Gly Val Asp Ile<br>                     165                     170                     175 | 528 |
| aac atg cgc gtg ggc gtg cat tct ggg aat gtc ctg tgt ggc gtg att<br>Asn Met Arg Val Gly Val His Ser Gly Asn Val Leu Cys Gly Val Ile<br>            180                     185                   190 | 576 |
| ggt ctg cag aag tgg caa tat gat gtg tgg tca cat gat gtg acc ttg<br>Gly Leu Gln Lys Trp Gln Tyr Asp Val Trp Ser His Asp Val Thr Leu<br>            195                     200                   205 | 624 |
| gcc aac cac atg gaa gct gga ggg gtc cct gga cgt gtt cac att tct<br>Ala Asn His Met Glu Ala Gly Gly Val Pro Gly Arg Val His Ile Ser<br>210                       215                     220 | 672 |
| tct gtc acc ctg gag cac ttg aat ggc gct tat aaa gtg gag gag gga<br>Ser Val Thr Leu Glu His Leu Asn Gly Ala Tyr Lys Val Glu Glu Gly<br>225                       230                     235                   240 | 720 |
| gat ggt gac att agg gac cca tat tta aaa cag cac ctg gtg aaa acc<br>Asp Gly Asp Ile Arg Asp Pro Tyr Leu Lys Gln His Leu Val Lys Thr<br>                     245                     250                     255 | 768 |
| tac ttt gtg atc aac ccc aag gga gaa cga cgg agc ccc cag cat ctc<br>Tyr Phe Val Ile Asn Pro Lys Gly Glu Arg Arg Ser Pro Gln His Leu<br>            260                     265                   270 | 816 |
| ttc aga cct cgc cac acc ctt gat gga gcc aaa atg agg gcc tcg gtc<br>Phe Arg Pro Arg His Thr Leu Asp Gly Ala Lys Met Arg Ala Ser Val<br>            275                     280                   285 | 864 |
| cgc atg acc cgg tac ttg gag tcc tgg ggg gca gcc aag ccc ttt gca<br>Arg Met Thr Arg Tyr Leu Glu Ser Trp Gly Ala Ala Lys Pro Phe Ala<br>290                       295                     300 | 912 |
| cac cta cat cac agg gac agc atg acc aca gag aac ggc aag atc agc<br>His Leu His His Arg Asp Ser Met Thr Thr Glu Asn Gly Lys Ile Ser<br>305                       310                     315                   320 | 960 |
| acc acg gat gta ccc atg ggt cag cat aat ttt caa aat cgc acc tta<br>Thr Thr Asp Val Pro Met Gly Gln His Asn Phe Gln Asn Arg Thr Leu<br>                     325                     330                     335 | 1008 |
| aga acc aag tca caa aag aag aga ttt gaa gaa gaa ttg aat gaa agg<br>Arg Thr Lys Ser Gln Lys Lys Arg Phe Glu Glu Glu Leu Asn Glu Arg<br>            340                     345                   350 | 1056 |
| atg att caa gca att gat ggg att aat gca cag aag caa tgg ctc aag<br>Met Ile Gln Ala Ile Asp Gly Ile Asn Ala Gln Lys Gln Trp Leu Lys<br>            355                     360                   365 | 1104 |
| tct gaa gac att cag aga atc tca ctg ctt ttc tat aac aaa gta cta<br>Ser Glu Asp Ile Gln Arg Ile Ser Leu Leu Phe Tyr Asn Lys Val Leu<br>370                       375                     380 | 1152 |

-continued

```
gaa aaa gag tac cgg gcc acg gca ctg cca gcg ttc aag tat tat gtg      1200
Glu Lys Glu Tyr Arg Ala Thr Ala Leu Pro Ala Phe Lys Tyr Tyr Val
385                 390                 395                 400 act tgt gcc tgt ctc ata ttc ttc tgc atc ttc att gtg cag att ctc      1248
Thr Cys Ala Cys Leu Ile Phe Phe Cys Ile Phe Ile Val Gln Ile Leu
            405                 410                 415 gtg ctg cca aaa acg tct gtc ctg ggc atc tcc ttt ggg gct gcg ttt      1296
Val Leu Pro Lys Thr Ser Val Leu Gly Ile Ser Phe Gly Ala Ala Phe
420                 425                 430 ctc ttg ctg gcc ttc atc ctc ttc gtc tgc ttt gct gga cag ctt ctg      1344
Leu Leu Leu Ala Phe Ile Leu Phe Val Cys Phe Ala Gly Gln Leu Leu
        435                 440                 445 caa tgc agc aaa aaa gcc tct ccc ctg ctc atg tgg ctt ttg aag tcc      1392
Gln Cys Ser Lys Lys Ala Ser Pro Leu Leu Met Trp Leu Leu Lys Ser
450                 455                 460 tcg ggc atc att gcc aac cgc ccc tgg cca cgg atc tct ctc acg atc      1440
Ser Gly Ile Ile Ala Asn Arg Pro Trp Pro Arg Ile Ser Leu Thr Ile
465                 470                 475                 480 atc acc aca gcc atc ata tta atg atg gcc gtg ttc aac atg ttt ttc      1488
Ile Thr Thr Ala Ile Ile Leu Met Met Ala Val Phe Asn Met Phe Phe
            485                 490                 495 ctg agt gac tca gag gaa aca atc cct cca act gcc aac aca aca aac      1536
Leu Ser Asp Ser Glu Glu Thr Ile Pro Pro Thr Ala Asn Thr Thr Asn
        500                 505                 510 aca agc ttt tca gcc tca aat aat cag gtg gcg att ctg cgt gcg cag      1584
Thr Ser Phe Ser Ala Ser Asn Asn Gln Val Ala Ile Leu Arg Ala Gln
515                 520                 525 aat tta ttt ttc ctc ccg tac ttt atc tac agc tgc att ctg gga ctg      1632
Asn Leu Phe Phe Leu Pro Tyr Phe Ile Tyr Ser Cys Ile Leu Gly Leu
530                 535                 540 ata tcc tgt tcc gtg ttc ctg cgg gta aac tat gag ctg aag atg ttg      1680
Ile Ser Cys Ser Val Phe Leu Arg Val Asn Tyr Glu Leu Lys Met Leu
545                 550                 555                 560 atc atg atg gtg gcc ttg gtg ggc tac aac acc atc cta ctc cac acc      1728
Ile Met Met Val Ala Leu Val Gly Tyr Asn Thr Ile Leu Leu His Thr
            565                 570                 575 cac gcc cac gtc ctg ggc gac tac agc cag gtc tta ttt gag aga cca      1776
His Ala His Val Leu Gly Asp Tyr Ser Gln Val Leu Phe Glu Arg Pro
        580                 585                 590 ggc att tgg aaa gac ctg aag acc atg ggc tct gtg tct ctc tct ata      1824
Gly Ile Trp Lys Asp Leu Lys Thr Met Gly Ser Val Ser Leu Ser Ile
595                 600                 605 ttc ttc atc aca ctg ctt gtt ctg ggt aga cag aat gaa tat tac tgt      1872
Phe Phe Ile Thr Leu Leu Val Leu Gly Arg Gln Asn Glu Tyr Tyr Cys
610                 615                 620 agg tta gac ttc tta tgg aag aac aaa ttc aaa aaa gag cgg gag gag      1920
Arg Leu Asp Phe Leu Trp Lys Asn Lys Phe Lys Lys Glu Arg Glu Glu
625                 630                 635                 640 ata gag acc atg gag aac ctg aac cgc gtg ctg ctg gag aac gtg ctt      1968
Ile Glu Thr Met Glu Asn Leu Asn Arg Val Leu Leu Glu Asn Val Leu
            645                 650                 655 ccc gcg cac gtg gct gag cac ttc ctg gcc agg agc ctg aag aat gag      2016
Pro Ala His Val Ala Glu His Phe Leu Ala Arg Ser Leu Lys Asn Glu
        660                 665                 670 gag cta tac cac cag tcc tat gac tgc gtc tgt gtc atg ttt gcc tcc      2064
Glu Leu Tyr His Gln Ser Tyr Asp Cys Val Cys Val Met Phe Ala Ser
675                 680                 685 att ccg gat ttc aaa gaa ttt tat aca gaa tcc gac gtg aac aag gag      2112
Ile Pro Asp Phe Lys Glu Phe Tyr Thr Glu Ser Asp Val Asn Lys Glu
```

|   |   |
|---|---|
| ggc ttg gaa tgc ctt cgg ctc ctg aac gag atc atc gct gac ttt gat<br>Gly Leu Glu Cys Leu Arg Leu Leu Asn Glu Ile Ile Ala Asp Phe Asp<br>705                    710                715               720 | 2160 |
| gat ctt ctt tcc aag cca aaa ttc agt gga gtt gaa aag att aag acc<br>Asp Leu Leu Ser Lys Pro Lys Phe Ser Gly Val Glu Lys Ile Lys Thr<br>                     725                730               735 | 2208 |
| att ggc agc aca tac atg gca gca aca ggt ctg agc gct gtg ccc agc<br>Ile Gly Ser Thr Tyr Met Ala Ala Thr Gly Leu Ser Ala Val Pro Ser<br>               740                745               750 | 2256 |
| cag gag cac tcc cag gag ccc gag cgg cag tac atg cac att ggc acc<br>Gln Glu His Ser Gln Glu Pro Glu Arg Gln Tyr Met His Ile Gly Thr<br>755                    760                765 | 2304 |
| atg gtg gag ttt gct ttt gcc ctg gta ggg aag ctg gat gcc atc aac<br>Met Val Glu Phe Ala Phe Ala Leu Val Gly Lys Leu Asp Ala Ile Asn<br>           770                775               780 | 2352 |
| aag cac tcc ttc aac gac ttc aaa ttg cga gtg ggt att aac cat gga<br>Lys His Ser Phe Asn Asp Phe Lys Leu Arg Val Gly Ile Asn His Gly<br>785                    790                795             800 | 2400 |
| cct gtg ata gct ggt gtg att gga gct cag aag cca caa tat gat atc<br>Pro Val Ile Ala Gly Val Ile Gly Ala Gln Lys Pro Gln Tyr Asp Ile<br>                    805                810               815 | 2448 |
| tgg ggc aac act gtc aat gtg gcc agt agg atg gac agc acc gga gtc<br>Trp Gly Asn Thr Val Asn Val Ala Ser Arg Met Asp Ser Thr Gly Val<br>           820                825               830 | 2496 |
| ctg gac aaa ata cag gtt acc gag gag acg agc ctc gtc ctg cag acc<br>Leu Asp Lys Ile Gln Val Thr Glu Glu Thr Ser Leu Val Leu Gln Thr<br>835                    840                845 | 2544 |
| ctc gga tac acg tgc acc tgt cga gga ata atc aac gtg aaa gga aag<br>Leu Gly Tyr Thr Cys Thr Cys Arg Gly Ile Ile Asn Val Lys Gly Lys<br>          850                855               860 | 2592 |
| ggg gac ctg aag acg tac ttt gta aac aca gaa atg tca agg tcc ctt<br>Gly Asp Leu Lys Thr Tyr Phe Val Asn Thr Glu Met Ser Arg Ser Leu<br>865                    870                875             880 | 2640 |
| tcc cag agc aac gtg gca tcc tga agagtcacct tcattttggc aagaagactg<br>Ser Gln Ser Asn Val Ala Ser<br>                    885 | 2694 |
| tattttcagg aaggtatcac acactttctg actgcaactt ctgtcccttg tttttgatgt | 2754 |
| gcgtgctgtc tgtcctatgg agcctctgca gactcgttct cgtgacccag tggcataccg | 2814 |
| tttggtgtct gatgtgtgcc cagatcgttc tgccacttgc actgtgcttg ctcctaagca | 2874 |
| aaagggaaaa ggagcgcgcg tgatagaaga aaagcactgg gagaactaac agaggagaaa | 2934 |
| ggtgaaacac acacacattc ttaaggcaat aaaactaggg ggtgtatatt atcttctggt | 2994 |
| gcatgttctt ttctggaaaa tatggtagct cgccaaccgc atctgctcat ctgatattca | 3054 |
| aacacacagt attcgtgaat aagttgattc tgtcccccac gtggactctg tgctcaccca | 3114 |
| ttgtctcatt gccagtggtg tccaagggcc cccgttggga cccacggctc tcgtccctct | 3174 |
| gctccgtgtg tctcatgcca gcagcacgtc gccatccgtc accagaatta gtcctcacag | 3234 |
| cctaggacca gttttgtatc aaactcgtct gatgttttga tgccatttgt cttttgtaaa | 3294 |
| gttaattcat taaagtttt atgtactttg atttacagtg cctgtatctt ttattttcct | 3354 |
| gtcttctttc tcctgtggtt tgctccagaa ttaaggtttg ttttccatcc attctccctt | 3414 |
| ttgacacagt tgtttcagaa agagctctcc agaagccaat attgagatgt aattcagatt | 3474 |
| aggacacagt gtgtgacgca gataactggt tactcagctc cctggaaagc aggcaagcat | 3534 |
| gttgaatgta tctagtggtc tgattttaat ttgggcatct ctagagaacg ctttcaggga | 3594 |

-continued

```
aaaatacttt aatagtaaaa agattctctg cgagcaacag tgccccctcc gtccactacg    3654
ctcctgtctc caagaatgtt ttgctagagc taacagacat agactgcaaa agaataattt    3714
ggaatcagct atgcaaatca gtctcacaat agcgtgagct aactgagaga agtactaaga    3774
cccacaaact gcctgttaag tctgagaagg ctaaagaaga cacacagcca acgttcatgc    3834 attttttaaag acagaaggcc ttgaagaatt tgttcttgta aatccaacac aagttgtttg    3894
gtacttttaa cataaagaaa tcatactttg ccaaatagtg aaaagtagag caatcgtgta    3954
taagctaatg tttaaaagca aaactgcaaa ttgtagccca gttggtcaaa cttgttttct    4014
ttttataact catggcaggc atctgtaaga agtagagaac ccagatgatc tcttaggaag    4074
ccttttattc gtgggaactc gaacttgaag cacaagttcc tggtttgaat cctggctctg    4134 atttttttact ggctgtgtga ctttgaacac atctcttagt ccctcttagg agtactttcc    4194
ttattggcaa cttatggaat cgctagtgat taaacgaggc aatgactgtg agagagcctg    4254
gcaggtgccc cgtggtacat tcacagcacg ggcacagctg ctgtgccagg actgtgactc    4314
attcccagta aaaggcactt atcgaagctg ataaccgtcc ttcatcaccg aagtgtgagt    4374
agagcatgac ttatttagta ttctgcctca atggggaatt ttttgatcct gtaatcacaa    4434
ctcagcattg gccttaatat acctaaatct ccaaaaacag tgattaaagc aagagaatta    4494
ttacaagggc ttttctcttt cctctaactc attcttcacg gatgccgtag cgtttccgtg    4554
agctcaaact ggccttggtg taaaatgtgt aaggatgagc agcaggcgtg cctcgtgggt    4614
tcttcctctg ttacatcctg ctacactcat ctgcaggtca ccttagttca cctaccctga    4674
gtgaacaccc ccagctgggt ggtccaccaa gttctcataa acagagtccc tcccattccc    4734
ccacggggtg caccgaactt gggtttgcgc taaaagaac tcaaaaggag aactgtgctc    4794
tcccaaagcc atatcaccag tcttaccaaa caataggctt ttaaaagcac tgagtcattg    4854
tcagaatcca ctatgggaag ctctgtgtgt acctggtccc ttctaggtgt ggtcccatag    4914
gagcagcctt agcatcccct gtgaacttat caaaaatgca aattctcagg ccccaacctg    4974
aaggaggacc ctgaatttga gatccccggg gctggggccc agcacaactg ctgtttagtg    5034
aacaggttct ccaggtgatt ctgatccctg atcaagcttc agacctccct ccctccccag    5094 tgttttttgca ggtgaggaaa caggggcaga gtaattcagg cacatgtgtt cagagttcca    5154
cagttgatta gcagttgagg ccaggctaga atggaaaact gcctgttcct tgaatctgaa    5214
agagcattat tcctggtcaa agctccttaa agttctgggc agctaaaagc atccctgtga    5274
gcaaaaatgc caggcagaaa actggcagtg cacctctcat cagcccaggt cccagtgcca    5334
ttggcttcaa gaaaaaaaaa aatctctccc caatgctctc cttaacctttt aagtcttaca    5394 ggaagcctct catagaaatt gcctccagtc cagtttccca aaacccccag tgttttacat    5454
atctgtttag gagtgtctaa gttttgtcat caatccacga tgttattctt ccttcccaac    5514
tcactgtgct cctaaaggca gcaaccattc atctttcctt tgctctggat acaccgaatg    5574
accaggtaac atcatcaggc cgggtgcagt ggctcctata atcccgatat tttgggaggc    5634
cgaggagaga ggatcactta agcccaggag tctgagacca gcctgggcaa catagcaaga    5694
cccccatctc tgcaaaaaaa taagaaaatt agcttggcat ggtggcacgt gcctgtagtc    5754
ccagctacat gggaggctga ggtgggagga tcacttgagc ccaggaagtc cagaacgtag    5814
tgagccttga ttataccact gcactccagc ctgggtgaca gagcgagact ctgtctcag    5873
```

<210> SEQ ID NO 3

```
<211> LENGTH: 887
<212> TYPE: PRT
<213> ORGANISM: Homo sapiens

<400> SEQUENCE: 3

Gly Ala Tyr His Lys His Leu Met Glu Leu Ala Leu Gln Gln Thr Tyr
1               5                   10                  15

Gln Asp Thr Cys Asn Cys Ile Lys Ser Arg Ile Lys Leu Glu Phe Glu
            20                  25                  30

Lys Arg Gln Gln Glu Arg Leu Leu Ser Leu Leu Pro Ala His Ile
        35                  40                  45

Ala Met Glu Met Lys Ala Glu Ile Ile Gln Arg Leu Gln Gly Pro Lys
    50                  55                  60

Ala Gly Gln Met Glu Asn Thr Asn Asn Phe His Asn Leu Tyr Val Lys
65                  70                  75                  80

Arg His Thr Asn Val Ser Ile Leu Tyr Ala Asp Ile Val Gly Phe Thr
                85                  90                  95

Arg Leu Ala Ser Asp Cys Ser Pro Gly Glu Leu Val His Met Leu Asn
            100                 105                 110

Glu Leu Phe Gly Lys Phe Asp Gln Ile Ala Lys Glu Asn Glu Cys Met
        115                 120                 125

Arg Ile Lys Ile Leu Gly Asp Cys Tyr Tyr Cys Val Ser Gly Leu Pro
    130                 135                 140

Ile Ser Leu Pro Asn His Ala Lys Asn Cys Val Lys Met Gly Leu Asp
145                 150                 155                 160

Met Cys Glu Ala Ile Lys Lys Val Arg Asp Ala Thr Gly Val Asp Ile
                165                 170                 175

Asn Met Arg Val Gly Val His Ser Gly Asn Val Leu Cys Gly Val Ile
            180                 185                 190

Gly Leu Gln Lys Trp Gln Tyr Asp Val Trp Ser His Asp Val Thr Leu
        195                 200                 205

Ala Asn His Met Glu Ala Gly Gly Val Pro Gly Arg Val His Ile Ser
    210                 215                 220

Ser Val Thr Leu Glu His Leu Asn Gly Ala Tyr Lys Val Glu Glu Gly
225                 230                 235                 240

Asp Gly Asp Ile Arg Asp Pro Tyr Leu Lys Gln His Leu Val Lys Thr
                245                 250                 255

Tyr Phe Val Ile Asn Pro Lys Gly Glu Arg Arg Ser Pro Gln His Leu
            260                 265                 270

Phe Arg Pro Arg His Thr Leu Asp Gly Ala Lys Met Arg Ala Ser Val
        275                 280                 285

Arg Met Thr Arg Tyr Leu Glu Ser Trp Gly Ala Ala Lys Pro Phe Ala
    290                 295                 300

His Leu His His Arg Asp Ser Met Thr Thr Glu Asn Gly Lys Ile Ser
305                 310                 315                 320

Thr Thr Asp Val Pro Met Gly Gln His Asn Phe Gln Asn Arg Thr Leu
                325                 330                 335

Arg Thr Lys Ser Gln Lys Lys Arg Phe Glu Glu Glu Leu Asn Glu Arg
            340                 345                 350

Met Ile Gln Ala Ile Asp Gly Ile Asn Ala Gln Lys Gln Trp Leu Lys
        355                 360                 365

Ser Glu Asp Ile Gln Arg Ile Ser Leu Leu Phe Tyr Asn Lys Val Leu
370                 375                 380

Glu Lys Glu Tyr Arg Ala Thr Ala Leu Pro Ala Phe Lys Tyr Tyr Val
```

-continued

```
              385                 390                 395                 400
        Thr Cys Ala Cys Leu Ile Phe Phe Cys Ile Phe Ile Val Gln Ile Leu
                        405                 410                 415
        Val Leu Pro Lys Thr Ser Val Leu Gly Ile Ser Phe Gly Ala Ala Phe
                        420                 425                 430
        Leu Leu Leu Ala Phe Ile Leu Phe Val Cys Phe Ala Gly Gln Leu Leu
                        435                 440                 445
        Gln Cys Ser Lys Lys Ala Ser Pro Leu Leu Met Trp Leu Leu Lys Ser
                        450                 455                 460
        Ser Gly Ile Ile Ala Asn Arg Pro Trp Pro Arg Ile Ser Leu Thr Ile
        465                 470                 475                 480
        Ile Thr Thr Ala Ile Ile Leu Met Met Ala Val Phe Asn Met Phe Phe
                        485                 490                 495
        Leu Ser Asp Ser Glu Glu Thr Ile Pro Pro Thr Ala Asn Thr Thr Asn
                        500                 505                 510
        Thr Ser Phe Ser Ala Ser Asn Asn Gln Val Ala Ile Leu Arg Ala Gln
                        515                 520                 525
        Asn Leu Phe Phe Leu Pro Tyr Phe Ile Tyr Ser Cys Ile Leu Gly Leu
                        530                 535                 540
        Ile Ser Cys Ser Val Phe Leu Arg Val Asn Tyr Glu Leu Lys Met Leu
        545                 550                 555                 560
        Ile Met Met Val Ala Leu Val Gly Tyr Asn Thr Ile Leu Leu His Thr
                        565                 570                 575
        His Ala His Val Leu Gly Asp Tyr Ser Gln Val Leu Phe Glu Arg Pro
                        580                 585                 590
        Gly Ile Trp Lys Asp Leu Lys Thr Met Gly Ser Val Ser Leu Ser Ile
                        595                 600                 605
        Phe Phe Ile Thr Leu Leu Val Leu Gly Arg Gln Asn Glu Tyr Tyr Cys
                        610                 615                 620
        Arg Leu Asp Phe Leu Trp Lys Asn Lys Phe Lys Glu Arg Glu Glu
        625                 630                 635                 640
        Ile Glu Thr Met Glu Asn Leu Asn Arg Val Leu Leu Glu Asn Val Leu
                        645                 650                 655
        Pro Ala His Val Ala Glu His Phe Leu Ala Arg Ser Leu Lys Asn Glu
                        660                 665                 670
        Glu Leu Tyr His Gln Ser Tyr Asp Cys Val Cys Val Met Phe Ala Ser
                        675                 680                 685
        Ile Pro Asp Phe Lys Glu Phe Tyr Thr Glu Ser Asp Val Asn Lys Glu
                        690                 695                 700
        Gly Leu Glu Cys Leu Arg Leu Leu Asn Glu Ile Ile Ala Asp Phe Asp
        705                 710                 715                 720
        Asp Leu Leu Ser Lys Pro Lys Phe Ser Gly Val Glu Lys Ile Lys Thr
                        725                 730                 735
        Ile Gly Ser Thr Tyr Met Ala Ala Thr Gly Leu Ser Ala Val Pro Ser
                        740                 745                 750
        Gln Glu His Ser Gln Glu Pro Glu Arg Gln Tyr Met His Ile Gly Thr
                        755                 760                 765
        Met Val Glu Phe Ala Phe Ala Leu Val Gly Lys Leu Asp Ala Ile Asn
                        770                 775                 780
        Lys His Ser Phe Asn Asp Phe Lys Leu Arg Val Gly Ile Asn His Gly
        785                 790                 795                 800
        Pro Val Ile Ala Gly Val Ile Gly Ala Gln Lys Pro Gln Tyr Asp Ile
                        805                 810                 815
```

```
Trp Gly Asn Thr Val Asn Val Ala Ser Arg Met Asp Ser Thr Gly Val
        820                 825                 830

Leu Asp Lys Ile Gln Val Thr Glu Glu Thr Ser Leu Val Leu Gln Thr
        835                 840                 845

Leu Gly Tyr Thr Cys Thr Cys Arg Gly Ile Ile Asn Val Lys Gly Lys
        850                 855                 860

Gly Asp Leu Lys Thr Tyr Phe Val Asn Thr Glu Met Ser Arg Ser Leu
865                 870                 875                 880

Ser Gln Ser Asn Val Ala Ser
                885

<210> SEQ ID NO 4
<211> LENGTH: 3261
<212> TYPE: DNA
<213> ORGANISM: Homo sapiens

<400> SEQUENCE: 4
```

| | | |
|---|---|---:|
| atgcggcacc gccgctacct gcgggaccgc tccgaggagg cggcgggcgg cggagacggg | | 60 |
| ctgccgcggt cccgggactg gctctacgag tcctactact gcatgagcca gcagcacccg | | 120 |
| ctcatcgtct tcctgctgct catcgtcatg ggctcctgcc tcgccctgct cgccgtcttc | | 180 |
| ttcgcgctcg gctggaagt tgaagaccat gtggcgtttc taataacagt tccaactgcc | | 240 |
| ctggcgattt tctttgcgat atttatcctg gtctgcatcg agtctgtgtt taagaagctg | | 300 |
| ctgccgcctct tctcgttggt gatatggata tgccttgttg ccatgggata cctgttcatg | | 360 |
| tgttttggag gcaccgtctc tccctgggac caggtatcgt tcttcctctt catcatcttc | | 420 |
| gtggtgtaca ccatgctgcc cttcaacatg cgagacgcca tcattgccag cgtcctcacc | | 480 |
| tcctcctccc acaccatcgt gcttagcgtc tgcctgtctg caacaccggg aggcaaggag | | 540 |
| cacctggtct ggcagatcct ggccaatgtg atcattttca tctgtgggaa cctggcggga | | 600 |
| gcctaccata agcacctcat ggaactcgct cttcagcaaa catatcagga cacctgtaat | | 660 |
| tgcatcaagt cgcggatcaa gttggaattt gaaaaacgtc aacaggagcg gcttctgctc | | 720 |
| tccctgctgc cggcccacat cgccatggag atgaaagcgg agatcatcca gaggctgcag | | 780 |
| ggcccccaagg cgggccagat ggagaacaca aataacttcc acaacctgta tgtgaagcgg | | 840 |
| catacaaacg tgagcatctt atacgctgac atcgttggct ttacccggct ggcaagtgac | | 900 |
| tgctcccccgg gagaactagt ccacatgctg aatgagctct ttggaaagtt tgatcaaatt | | 960 |
| gcaaaggaga atgaatgcat gagaattaaa atttaggag actgctacta ctgtgtatct | | 1020 |
| ggactcccta tatctctccc taaccatgcc aagaactgtg tgaaaatggg gctggacatg | | 1080 |
| tgtgaagcca taagaaagt gagggatgct actggagttg atatcaacat cgcgcgtggc | | 1140 |
| gtgcattctg ggaatgtcct gtgtggcgtg attggtctgc agaagtggca atatgatgtg | | 1200 |
| tggtcacatg atgtgacctt ggccaaccac atggaagctg gagggtccc tggacgtgtt | | 1260 |
| cacatttctt ctgtcaccct ggagcacttg aatggcgctt ataaagtgga ggagggagat | | 1320 |
| ggtgacatta gggacccata tttaaaacag cacctggtga aaacctactt tgtgatcaac | | 1380 |
| cccaagggag aacgacggag cccccagcat ctcttcagac ctcgccacac ccttgatgga | | 1440 |
| gccaaaatga gggcctcggt ccgcatgacc cggtacttgg agtcctgggg ggcagccaag | | 1500 |
| cccctttgcac acctacatca cagggacagc atgaccacag agaacggcaa gatcagcacc | | 1560 |
| acggatgtac ccatgggtca gcataatttt caaaatcgca ccttaagaac caagtcacaa | | 1620 |
| aagaagagat ttgaagaaga attgaatgaa aggatgattc aagcaattga tgggattaat | | 1680 |

```
gcacagaagc aatggctcaa gtctgaagac attcagagaa tctcactgct tttctataac    1740
aaagtactag aaaaagagta ccgggccacg gcactgccag cgttcaagta ttatgtgact    1800
tgtgcctgtc tcatattctt ctgcatcttc attgtgcaga ttctcgtgct gccaaaaacg    1860
tctgtcctgg gcatctcctt tggggctgcg tttctcttgc tggccttcat cctcttcgtc    1920
tgctttgctg acagcttct gcaatgcagc aaaaaagcct ctcccctgct catgtggctt     1980
ttgaagtcct cgggcatcat tgccaaccgc ccctggccac ggatctctct cacgatcatc    2040
accacagcca tcatattaat gatggccgtg ttcaacatgt ttttcctgag tgactcagag    2100
gaaacaatcc ctccaactgc caacacaaca aacacaagct tttcagcctc aaataatcag    2160
gtggcgattc tgcgtgcgca gaatttattt ttcctcccgt actttatcta cagctgcatt    2220
ctgggactga tatcctgttc cgtgttcctg cgggtaaact atgagctgaa gatgttgatc    2280
atgatggtgg ccttggtggg ctacaacacc atcctactcc acacccacgc ccacgtcctg    2340
ggcgactaca gccaggtctt atttgagaga ccaggcattt ggaaagacct gaagaccatg    2400
ggctctgtgt ctctctctat attcttcatc acactgcttg ttctgggtag acagaatgaa    2460
tattactgta ggttagactt cttatggaag aacaaattca aaaagagcg ggaggagata     2520
gagaccatgg agaacctgaa ccgcgtgctg ctggagaacg tgcttcccgc gcacgtggct    2580
gagcacttcc tggccaggag cctgaagaat gaggagctat accaccagtc ctatgactgc    2640
gtctgtgtca tgtttgcctc cattccggat ttcaaagaat tttatacaga atccgacgtg    2700
aacaaggagg gcttggaatg ccttcggctc ctgaacgaga tcatcgctga ctttgatgat    2760
cttctttcca gccaaaatt cagtggagtt gaaaagatta agaccattgg cagcacatac     2820
atggcagcaa caggtctgag cgctgtgccc agccaggagc actcccagga gcccgagcgg    2880
cagtacatgc acattggcac catggtggag tttgcttttg ccctggtagg gaagctggat    2940
gccatcaaca agcactcctt caacgacttc aaattgcgag tgggtattaa ccatggacct    3000
gtgatagctg gtgtgattgg agctcagaag ccacaatatg atatctgggg caacactgtc    3060
aatgtggcca gtaggatgga cagcaccgga gtcctgacc aaaatacaggt taccgaggag      3120
acgagcctcg tcctgcagac cctcggatac acgtgcacct gtcgaggaat aatcaacgtg    3180
aaaggaaagg gggacctgaa gacgtacttt gtaaacacag aaatgtcaag gtcccttttcc   3240
cagagcaacg tggcatcctg a                                              3261
```

```
<210> SEQ ID NO 5
<211> LENGTH: 6470
<212> TYPE: DNA
<213> ORGANISM: Homo sapiens
<220> FEATURE:
<221> NAME/KEY: CDS
<222> LOCATION: (1)..(3261)
<223> OTHER INFORMATION:

<400> SEQUENCE: 5 atg cgg cac cgc cgc tac ctg cgg gac cgc tcc gag gag gcg gcg ggc      48
Met Arg His Arg Arg Tyr Leu Arg Asp Arg Ser Glu Glu Ala Ala Gly
1               5                   10                  15 ggc gga gac ggg ctg ccg cgg tcc cgg gac tgg ctc tac gag tcc tac      96
Gly Gly Asp Gly Leu Pro Arg Ser Arg Asp Trp Leu Tyr Glu Ser Tyr
            20                  25                  30 tac tgc atg agc cag cag cac ccg ctc atc gtc ttc ctg ctg ctc atc     144
Tyr Cys Met Ser Gln Gln His Pro Leu Ile Val Phe Leu Leu Leu Ile
        35                  40                  45
```

-continued

| | |
|---|---|
| gtc atg ggc tcc tgc ctc gcc ctg ctc gcc gtc ttc ttc gcg ctc ggg<br>Val Met Gly Ser Cys Leu Ala Leu Leu Ala Val Phe Phe Ala Leu Gly<br>50                     55                     60 | 192 |
| ctg gaa gtt gaa gac cat gtg gcg ttt cta ata aca gtt cca act gcc<br>Leu Glu Val Glu Asp His Val Ala Phe Leu Ile Thr Val Pro Thr Ala<br>65                     70                     75                     80 | 240 |
| ctg gcg att ttc ttt gcg ata ttt atc ctg gtc tgc atc gag tct gtg<br>Leu Ala Ile Phe Phe Ala Ile Phe Ile Leu Val Cys Ile Glu Ser Val<br>                     85                     90                     95 | 288 |
| ttt aag aag ctg ctg cgc ctc ttc tcg ttg gtg ata tgg ata tgc ctt<br>Phe Lys Lys Leu Leu Arg Leu Phe Ser Leu Val Ile Trp Ile Cys Leu<br>                   100                   105                110 | 336 |
| gtt gcc atg gga tac ctg ttc atg tgt ttt gga ggc acc gtc tct ccc<br>Val Ala Met Gly Tyr Leu Phe Met Cys Phe Gly Gly Thr Val Ser Pro<br>               115                   120                  125 | 384 |
| tgg gac cag gta tcg ttc ttc ctc ttc atc atc ttc gtg gtg tac acc<br>Trp Asp Gln Val Ser Phe Phe Leu Phe Ile Ile Phe Val Val Tyr Thr<br>130                    135                   140 | 432 |
| atg ctg ccc ttc aac atg cga gac gcc atc att gcc agc gtc ctc acc<br>Met Leu Pro Phe Asn Met Arg Asp Ala Ile Ile Ala Ser Val Leu Thr<br>145                    150                   155                160 | 480 |
| tcc tcc tcc cac acc atc gtg ctt agc gtc tgc ctg tct gca aca ccg<br>Ser Ser Ser His Thr Ile Val Leu Ser Val Cys Leu Ser Ala Thr Pro<br>                   165                   170                175 | 528 |
| gga ggc aag gag cac ctg gtc tgg cag atc ctg gcc aat gtg atc att<br>Gly Gly Lys Glu His Leu Val Trp Gln Ile Leu Ala Asn Val Ile Ile<br>                   180                   185                190 | 576 |
| ttc atc tgt ggg aac ctg gcg gga gcc tac cat aag cac ctc atg gaa<br>Phe Ile Cys Gly Asn Leu Ala Gly Ala Tyr His Lys His Leu Met Glu<br>                   195                   200                205 | 624 |
| ctc gct ctt cag caa aca tat cag gac acc tgt aat tgc atc aag tcg<br>Leu Ala Leu Gln Gln Thr Tyr Gln Asp Thr Cys Asn Cys Ile Lys Ser<br>210                    215                   220 | 672 |
| cgg atc aag ttg gaa ttt gaa aaa cgt caa cag gag cgg ctt ctg ctc<br>Arg Ile Lys Leu Glu Phe Glu Lys Arg Gln Gln Glu Arg Leu Leu Leu<br>225                    230                   235                240 | 720 |
| tcc ctg ctg ccg gcc cac atc gcc atg gag atg aaa gcg gag atc atc<br>Ser Leu Leu Pro Ala His Ile Ala Met Glu Met Lys Ala Glu Ile Ile<br>                   245                   250                255 | 768 |
| cag agg ctg cag ggc ccc aag gcg ggc cag atg gag aac aca aat aac<br>Gln Arg Leu Gln Gly Pro Lys Ala Gly Gln Met Glu Asn Thr Asn Asn<br>                   260                   265                270 | 816 |
| ttc cac aac ctg tat gtg aag cgg cat aca aac gtg agc atc tta tac<br>Phe His Asn Leu Tyr Val Lys Arg His Thr Asn Val Ser Ile Leu Tyr<br>                   275                   280                285 | 864 |
| gct gac atc gtt ggc ttt acc cgg ctg gca agt gac tgc tcc ccg gga<br>Ala Asp Ile Val Gly Phe Thr Arg Leu Ala Ser Asp Cys Ser Pro Gly<br>290                    295                   300 | 912 |
| gaa cta gtc cac atg ctg aat gag ctc ttt gga aag ttt gat caa att<br>Glu Leu Val His Met Leu Asn Glu Leu Phe Gly Lys Phe Asp Gln Ile<br>305                    310                   315                320 | 960 |
| gca aag gag aat gaa tgc atg aga att aaa att tta gga gac tgc tac<br>Ala Lys Glu Asn Glu Cys Met Arg Ile Lys Ile Leu Gly Asp Cys Tyr<br>                   325                   330                335 | 1008 |
| tac tgt gta tct gga ctc cct ata tct ctc cct aac cat gcc aag aac<br>Tyr Cys Val Ser Gly Leu Pro Ile Ser Leu Pro Asn His Ala Lys Asn<br>                   340                   345                350 | 1056 |
| tgt gtg aaa atg ggg ctg gac atg tgt gaa gcc ata aag aaa gtg agg<br>Cys Val Lys Met Gly Leu Asp Met Cys Glu Ala Ile Lys Lys Val Arg<br>                   355                   360                365 | 1104 |

-continued

```
gat gct act gga gtt gat atc aac atg cgc gtg ggc gtg cat tct ggg      1152
Asp Ala Thr Gly Val Asp Ile Asn Met Arg Val Gly Val His Ser Gly
    370                 375                 380 aat gtc ctg tgt ggc gtg att ggt ctg cag aag tgg caa tat gat gtg      1200
Asn Val Leu Cys Gly Val Ile Gly Leu Gln Lys Trp Gln Tyr Asp Val
385                 390                 395                 400 tgg tca cat gat gtg acc ttg gcc aac cac atg gaa gct gga ggg gtc      1248
Trp Ser His Asp Val Thr Leu Ala Asn His Met Glu Ala Gly Gly Val
                405                 410                 415 cct gga cgt gtt cac att tct tct gtc acc ctg gag cac ttg aat ggc      1296
Pro Gly Arg Val His Ile Ser Ser Val Thr Leu Glu His Leu Asn Gly
            420                 425                 430 gct tat aaa gtg gag gag gga gat ggt gac att agg gac cca tat tta      1344
Ala Tyr Lys Val Glu Glu Gly Asp Gly Asp Ile Arg Asp Pro Tyr Leu
        435                 440                 445 aaa cag cac ctg gtg aaa acc tac ttt gtg atc aac ccc aag gga gaa      1392
Lys Gln His Leu Val Lys Thr Tyr Phe Val Ile Asn Pro Lys Gly Glu
    450                 455                 460 cga cgg agc ccc cag cat ctc ttc aga cct cgc cac acc ctt gat gga      1440
Arg Arg Ser Pro Gln His Leu Phe Arg Pro Arg His Thr Leu Asp Gly
465                 470                 475                 480 gcc aaa atg agg gcc tcg gtc cgc atg acc cgg tac ttg gag tcc tgg      1488
Ala Lys Met Arg Ala Ser Val Arg Met Thr Arg Tyr Leu Glu Ser Trp
                485                 490                 495 ggg gca gcc aag ccc ttt gca cac cta cat cac agg gac agc atg acc      1536
Gly Ala Ala Lys Pro Phe Ala His Leu His His Arg Asp Ser Met Thr
            500                 505                 510 aca gag aac ggc aag atc agc acc acg gat gta ccc atg ggt cag cat      1584
Thr Glu Asn Gly Lys Ile Ser Thr Thr Asp Val Pro Met Gly Gln His
        515                 520                 525 aat ttt caa aat cgc acc tta aga acc aag tca caa aag aag aga ttt      1632
Asn Phe Gln Asn Arg Thr Leu Arg Thr Lys Ser Gln Lys Lys Arg Phe
    530                 535                 540 gaa gaa gaa ttg aat gaa agg atg att caa gca att gat ggg att aat      1680
Glu Glu Glu Leu Asn Glu Arg Met Ile Gln Ala Ile Asp Gly Ile Asn
545                 550                 555                 560 gca cag aag caa tgg ctc aag tct gaa gac att cag aga atc tca ctg      1728
Ala Gln Lys Gln Trp Leu Lys Ser Glu Asp Ile Gln Arg Ile Ser Leu
                565                 570                 575 ctt ttc tat aac aaa gta cta gaa aaa gag tac cgg gcc acg gca ctg      1776
Leu Phe Tyr Asn Lys Val Leu Glu Lys Glu Tyr Arg Ala Thr Ala Leu
            580                 585                 590 cca gcg ttc aag tat tat gtg act tgt gcc tgt ctc ata ttc ttc tgc      1824
Pro Ala Phe Lys Tyr Tyr Val Thr Cys Ala Cys Leu Ile Phe Phe Cys
        595                 600                 605 atc ttc att gtg cag att ctc gtg ctg cca aaa acg tct gtc ctg ggc      1872
Ile Phe Ile Val Gln Ile Leu Val Leu Pro Lys Thr Ser Val Leu Gly
    610                 615                 620 atc tcc ttt ggg gct gcg ttt ctc ttg ctg gcc ttc atc ctc ttc gtc      1920
Ile Ser Phe Gly Ala Ala Phe Leu Leu Leu Ala Phe Ile Leu Phe Val
625                 630                 635                 640 tgc ttt gct gga cag ctt ctg caa tgc agc aaa aaa gcc tct ccc ctg      1968
Cys Phe Ala Gly Gln Leu Leu Gln Cys Ser Lys Lys Ala Ser Pro Leu
                645                 650                 655 ctc atg tgg ctt ttg aag tcc tcg ggc atc att gcc aac cgc ccc tgg      2016
Leu Met Trp Leu Leu Lys Ser Ser Gly Ile Ile Ala Asn Arg Pro Trp
            660                 665                 670 cca cgg atc tct ctc acg atc atc acc aca gcc atc ata tta atg atg      2064
Pro Arg Ile Ser Leu Thr Ile Ile Thr Thr Ala Ile Ile Leu Met Met
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 675 |     |     |     |     | 680 |     |     |     |     | 685 |     |     |     |      |
| gcc | gtg | ttc | aac | atg | ttt | ttc | ctg | agt | gac | tca | gag | gaa | aca | atc | cct | 2112 |
| Ala | Val | Phe | Asn | Met | Phe | Phe | Leu | Ser | Asp | Ser | Glu | Glu | Thr | Ile | Pro |      |
|     |     | 690 |     |     |     |     | 695 |     |     |     |     | 700 |     |     |     |      |
| cca | act | gcc | aac | aca | aca | aac | aca | agc | ttt | tca | gcc | tca | aat | aat | cag | 2160 |
| Pro | Thr | Ala | Asn | Thr | Thr | Asn | Thr | Ser | Phe | Ser | Ala | Ser | Asn | Asn | Gln |      |
| 705 |     |     |     |     | 710 |     |     |     |     | 715 |     |     |     |     | 720 |      |
| gtg | gcg | att | ctg | cgt | gcg | cag | aat | tta | ttt | ttc | ctc | ccg | tac | ttt | atc | 2208 |
| Val | Ala | Ile | Leu | Arg | Ala | Gln | Asn | Leu | Phe | Phe | Leu | Pro | Tyr | Phe | Ile |      |
|     |     |     |     | 725 |     |     |     |     | 730 |     |     |     |     | 735 |     |      |
| tac | agc | tgc | att | ctg | gga | ctg | ata | tcc | tgt | tcc | gtg | ttc | ctg | cgg | gta | 2256 |
| Tyr | Ser | Cys | Ile | Leu | Gly | Leu | Ile | Ser | Cys | Ser | Val | Phe | Leu | Arg | Val |      |
|     |     |     | 740 |     |     |     |     | 745 |     |     |     |     | 750 |     |     |      |
| aac | tat | gag | ctg | aag | atg | ttg | atc | atg | atg | gtg | gcc | ttg | gtg | ggc | tac | 2304 |
| Asn | Tyr | Glu | Leu | Lys | Met | Leu | Ile | Met | Met | Val | Ala | Leu | Val | Gly | Tyr |      |
|     |     | 755 |     |     |     |     | 760 |     |     |     |     | 765 |     |     |     |      |
| aac | acc | atc | cta | ctc | cac | acc | cac | gcc | cac | gtc | ctg | ggc | gac | tac | agc | 2352 |
| Asn | Thr | Ile | Leu | Leu | His | Thr | His | Ala | His | Val | Leu | Gly | Asp | Tyr | Ser |      |
| 770 |     |     |     |     | 775 |     |     |     |     | 780 |     |     |     |     |     |      |
| cag | gtc | tta | ttt | gag | aga | cca | ggc | att | tgg | aaa | gac | ctg | aag | acc | atg | 2400 |
| Gln | Val | Leu | Phe | Glu | Arg | Pro | Gly | Ile | Trp | Lys | Asp | Leu | Lys | Thr | Met |      |
| 785 |     |     |     |     | 790 |     |     |     |     | 795 |     |     |     |     | 800 |      |
| ggc | tct | gtg | tct | ctc | tct | ata | ttc | ttc | atc | aca | ctg | ctt | gtt | ctg | ggt | 2448 |
| Gly | Ser | Val | Ser | Leu | Ser | Ile | Phe | Phe | Ile | Thr | Leu | Leu | Val | Leu | Gly |      |
|     |     |     | 805 |     |     |     |     | 810 |     |     |     |     | 815 |     |     |      |
| aga | cag | aat | gaa | tat | tac | tgt | agg | tta | gac | ttc | tta | tgg | aag | aac | aaa | 2496 |
| Arg | Gln | Asn | Glu | Tyr | Tyr | Cys | Arg | Leu | Asp | Phe | Leu | Trp | Lys | Asn | Lys |      |
|     |     | 820 |     |     |     |     | 825 |     |     |     |     | 830 |     |     |     |      |
| ttc | aaa | aaa | gag | cgg | gag | gag | ata | gag | acc | atg | gag | aac | ctg | aac | cgc | 2544 |
| Phe | Lys | Lys | Glu | Arg | Glu | Glu | Ile | Glu | Thr | Met | Glu | Asn | Leu | Asn | Arg |      |
|     |     |     | 835 |     |     |     |     | 840 |     |     |     |     | 845 |     |     |      |
| gtg | ctg | ctg | gag | aac | gtg | ctt | ccc | gcg | cac | gtg | gct | gag | cac | ttc | ctg | 2592 |
| Val | Leu | Leu | Glu | Asn | Val | Leu | Pro | Ala | His | Val | Ala | Glu | His | Phe | Leu |      |
| 850 |     |     |     |     | 855 |     |     |     |     | 860 |     |     |     |     |     |      |
| gcc | agg | agc | ctg | aag | aat | gag | gag | cta | tac | cac | cag | tcc | tat | gac | tgc | 2640 |
| Ala | Arg | Ser | Leu | Lys | Asn | Glu | Glu | Leu | Tyr | His | Gln | Ser | Tyr | Asp | Cys |      |
| 865 |     |     |     |     | 870 |     |     |     |     | 875 |     |     |     |     | 880 |      |
| gtc | tgt | gtc | atg | ttt | gcc | tcc | att | ccg | gat | ttc | aaa | gaa | ttt | tat | aca | 2688 |
| Val | Cys | Val | Met | Phe | Ala | Ser | Ile | Pro | Asp | Phe | Lys | Glu | Phe | Tyr | Thr |      |
|     |     |     |     | 885 |     |     |     |     | 890 |     |     |     |     | 895 |     |      |
| gaa | tcc | gac | gtg | aac | aag | gag | ggc | ttg | gaa | tgc | ctt | cgg | ctc | ctg | aac | 2736 |
| Glu | Ser | Asp | Val | Asn | Lys | Glu | Gly | Leu | Glu | Cys | Leu | Arg | Leu | Leu | Asn |      |
|     |     |     | 900 |     |     |     |     | 905 |     |     |     |     | 910 |     |     |      |
| gag | atc | atc | gct | gac | ttt | gat | gat | ctt | ctt | tcc | aag | cca | aaa | ttc | agt | 2784 |
| Glu | Ile | Ile | Ala | Asp | Phe | Asp | Asp | Leu | Leu | Ser | Lys | Pro | Lys | Phe | Ser |      |
|     |     | 915 |     |     |     |     | 920 |     |     |     |     | 925 |     |     |     |      |
| gga | gtt | gaa | aag | att | aag | acc | att | ggc | agc | aca | tac | atg | gca | gca | aca | 2832 |
| Gly | Val | Glu | Lys | Ile | Lys | Thr | Ile | Gly | Ser | Thr | Tyr | Met | Ala | Ala | Thr |      |
| 930 |     |     |     |     | 935 |     |     |     |     | 940 |     |     |     |     |     |      |
| ggt | ctg | agc | gct | gtg | ccc | agc | cag | gag | cac | tcc | cag | gag | ccc | gag | cgg | 2880 |
| Gly | Leu | Ser | Ala | Val | Pro | Ser | Gln | Glu | His | Ser | Gln | Glu | Pro | Glu | Arg |      |
| 945 |     |     |     |     | 950 |     |     |     |     | 955 |     |     |     |     | 960 |      |
| cag | tac | atg | cac | att | ggc | acc | atg | gtg | gag | ttt | gct | ttt | gcc | ctg | gta | 2928 |
| Gln | Tyr | Met | His | Ile | Gly | Thr | Met | Val | Glu | Phe | Ala | Phe | Ala | Leu | Val |      |
|     |     |     |     | 965 |     |     |     |     | 970 |     |     |     |     | 975 |     |      |
| ggg | aag | ctg | gat | gcc | atc | aac | aag | cac | tcc | ttc | aac | gac | ttc | aaa | ttg | 2976 |
| Gly | Lys | Leu | Asp | Ala | Ile | Asn | Lys | His | Ser | Phe | Asn | Asp | Phe | Lys | Leu |      |
|     |     |     | 980 |     |     |     |     | 985 |     |     |     |     | 990 |     |     |      |
| cga | gtg | ggt | att | aac | cat | gga | cct | gtg | ata | gct | ggt | gtg | att | gga | gct | 3024 |

-continued

```
                Arg Val Gly Ile Asn His Gly Pro  Val Ile Ala Gly Val  Ile Gly Ala
                    995                 1000                1005 cag aag  cca caa tat gat atc  tgg ggc aac act gtc  aat gtg gcc                    3069
Gln Lys  Pro Gln Tyr Asp Ile  Trp Gly Asn Thr Val  Asn Val Ala
    1010                 1015                 1020 agt agg  atg gac agc acc gga  gtc ctg gac aaa ata  cag gtt acc                    3114
Ser Arg  Met Asp Ser Thr Gly  Val Leu Asp Lys Ile  Gln Val Thr
    1025                 1030                 1035 gag gag  acg agc ctc gtc ctg  cag acc ctc gga tac  acg tgc acc                    3159
Glu Glu  Thr Ser Leu Val Leu  Gln Thr Leu Gly Tyr  Thr Cys Thr
    1040                 1045                 1050 tgt cga  gga ata atc aac gtg  aaa gga aag ggg gac  ctg aag acg                    3204
Cys Arg  Gly Ile Ile Asn Val  Lys Gly Lys Gly Asp  Leu Lys Thr
    1055                 1060                 1065 tac ttt  gta aac aca gaa atg  tca agg tcc ctt tcc  cag agc aac                    3249
Tyr Phe  Val Asn Thr Glu Met  Ser Arg Ser Leu Ser  Gln Ser Asn
    1070                 1075                 1080 gtg gca  tcc tga agagtcacct tcattttggc aagaagactg tattttcagg                      3301
Val Ala  Ser
    1085 aaggtatcac acactttctg actgcaactt ctgtcccttg tttttgatgt gcgtgctgtc                 3361 tgtcctatgg agcctctgca gactcgttct cgtgacccag tggcataccg tttggtgtct                 3421 gatgtgtgcc cagatcgttc tgccacttgc actgtgcttg ctcctaagca aaagggaaaa                 3481 ggagcgcgcg tgatagaaga aaagcactgg gagaactaac agaggagaaa ggtgaaacac                 3541 acacacattc ttaaggcaat aaaactaggg ggtgtatatt atcttctggt gcatgttctt                 3601 ttctggaaaa tatggtagct cgccaaccgc atctgctcat ctgatattca aacacacagt                 3661 attcgtgaat aagttgattc tgtccccac gtggactctg tgctcaccca ttgtctcatt                  3721 gccagtggtg tccaagggcc cccgttggga cccacggctc tcgtccctct gctccgtgtg                 3781 tctcatgcca gcagcacgtc gccatccgtc accagaatta gtcctcacag cctaggacca                 3841 gttttgtatc aaactcgtct gatgttttga tgccatttgt cttttgtaaa gttaattcat                 3901 taaaagtttt atgtactttg atttacagtg cctgtatctt ttattttcct gtcttctttc                 3961 tcctgtggtt tgctccagaa ttaaggtttg ttttccatcc attctcccctt ttgacacagt                4021 tgtttcagaa agagctctcc agaagccaat attgagatgt aattcagatt aggacacagt                4081 gtgtgacgca gataactggt tactcagctc cctggaaagc aggcaagcat gttgaatgta                 4141 tctagtggtc tgatttttaat ttgggcatct ctagagaacg ctttcaggga aaaatacttt               4201 aatagtaaaa agattctctg cgagcaacag tgccccctcc gtccactacg ctcctgtctc                 4261 caagaatgtt ttgctagagc taacagacat agactgcaaa agaataaattt ggaatcagct               4321 atgcaaatca gtctcacaat agcgtgagct aactgagaga agtactaaga cccacaaact                 4381 gcctgttaag tctgagaagg ctaaagaaga cacacagcca acgttcatgc atttttaaag                 4441 acagaaggcc ttgaagaatt tgttcttgta aatccaacac aagttgtttg gtacttttaa                 4501 cataaagaaa tcatactttg ccaaatagtg aaaagtagag caatcgtgta taagctaatg                 4561 tttaaaagca aaactgcaaa ttgtagccca gttggtcaaa cttgttttct ttttataact                 4621 catggcaggc atctgtaaga agtagagaac ccagatgatc tcttaggaag cctttttattc              4681 gtgggaactc gaacttgaag cacaagttcc tggtttgaat cctggctctg attttttact                4741 ggctgtgtga ctttgaacac atctcttagt ccctcttagg agtactttcc ttattggcaa                 4801 cttatggaat cgctagtgat taaacgaggc aatgactgtg agagagcctg gcaggtgccc                 4861
```

-continued

```
cgtggtacat tcacagcacg ggcacagctg ctgtgccagg actgtgactc attcccagta    4921
aaaggcactt atcgaagctg ataaccgtcc ttcatcaccg aagtgtgagt agagcatgac    4981
ttatttagta ttctgcctca atggggaatt ttttgatcct gtaatcacaa ctcagcattg    5041
gccttaatat acctaaatct ccaaaaacag tgattaaagc aagagaatta ttacaagggc    5101
tttctctttt cctctaactc attcttcacg gatgccgtag cgtttccgtg agctcaaact    5161
ggccttggtg taaaatgtgt aaggatgagc agcaggcgtg cctcgtgggt tcttcctctg    5221
ttacatcctg ctacactcat ctgcaggtca ccttagttca cctaccctga gtgaacaccc    5281
ccagctgggt ggtccaccaa gttctcataa acagagtccc tcccattccc ccacggggtg    5341
caccgaactt gggtttgcgc taaaagaac tcaaaggag aactgtgctc tcccaaagcc    5401
atatcaccag tcttaccaaa cataggctt taaaagcac tgagtcattg tcagaatcca    5461
ctatgggaag ctctgtgtgt acctggtccc ttctaggtgt ggtcccatag agcagcctt    5521 agcatcccct gtgaacttat caaaaatgca aattctcagg ccccaacctg aaggaggacc    5581
ctgaatttga gatccccggg gctggggccc agcacaactg ctgtttagtg aacaggttct    5641
ccaggtgatt ctgatccctg atcaagcttc agacctccct ccctcccag tgttttttgca    5701 ggtgaggaaa caggggcaga gtaattcagg cacatgtgtt cagagttcca cagttgatta    5761
gcagttgagg ccaggctaga atggaaaact gcctgttcct tgaatctgaa agagcattat    5821
tcctggtcaa agctccttaa agttctgggc agctaaaagc atccctgtga gcaaaaatgc    5881
caggcagaaa actggcagtg cacctctcat cagcccaggt cccagtgcca ttggcttcaa    5941
gaaaaaaaaa aatctctccc caatgctctc cttaacctt aagtcttaca ggaagcctct    6001
catagaaatt gcctccagtc cagtttccca aaaccccag tgttttacat atctgtttag    6061
gagtgtctaa gttttgtcat caatccacga tgttattctt ccttcccaac tcactgtgct    6121
cctaaaggca gcaaccattc atctttcctt tgctctggat acaccgaatg accaggtaac    6181
atcatcaggc cgggtgcagt ggctcctata atcccgatat tttgggaggc cgaggagaga    6241
ggatcactta agcccaggag tctgagacca gcctgggcaa catagcaaga cccccatctc    6301
tgcaaaaaaa taagaaaatt agcttggcat ggtggcacgt gcctgtagtc ccagctacat    6361
gggaggctga ggtgggagga tcacttgagc ccaggaagtc cagaacgtag tgagccttga    6421
ttataccact gcactccagc ctgggtgaca gagcgagact ctgtctcag              6470
```

<210> SEQ ID NO 6
<211> LENGTH: 1086
<212> TYPE: PRT
<213> ORGANISM: Homo sapiens

<400> SEQUENCE: 6

```
Met Arg His Arg Arg Tyr Leu Arg Asp Arg Ser Glu Glu Ala Ala Gly
1               5                   10                  15

Gly Gly Asp Gly Leu Pro Arg Ser Arg Asp Trp Leu Tyr Glu Ser Tyr
                20                  25                  30

Tyr Cys Met Ser Gln Gln His Pro Leu Ile Val Phe Leu Leu Ile
            35                  40                  45

Val Met Gly Ser Cys Leu Ala Leu Leu Ala Val Phe Ala Leu Gly
        50                  55                  60

Leu Glu Val Glu Asp His Val Ala Phe Leu Ile Thr Val Pro Thr Ala
65                  70                  75                  80

Leu Ala Ile Phe Phe Ala Ile Phe Ile Leu Val Cys Ile Glu Ser Val
                85                  90                  95
```

-continued

```
Phe Lys Lys Leu Leu Arg Leu Phe Ser Leu Val Ile Trp Ile Cys Leu
                100                 105                 110
Val Ala Met Gly Tyr Leu Phe Met Cys Phe Gly Gly Thr Val Ser Pro
            115                 120                 125
Trp Asp Gln Val Ser Phe Phe Leu Phe Ile Ile Phe Val Tyr Thr
        130                 135                 140
Met Leu Pro Phe Asn Met Arg Asp Ala Ile Ile Ala Ser Val Leu Thr
145                 150                 155                 160
Ser Ser Ser His Thr Ile Val Leu Ser Val Cys Leu Ser Ala Thr Pro
                165                 170                 175
Gly Gly Lys Glu His Leu Val Trp Gln Ile Leu Ala Asn Val Ile Ile
            180                 185                 190
Phe Ile Cys Gly Asn Leu Ala Gly Ala Tyr His Lys His Leu Met Glu
        195                 200                 205
Leu Ala Leu Gln Gln Thr Tyr Gln Asp Thr Cys Asn Cys Ile Lys Ser
    210                 215                 220
Arg Ile Lys Leu Glu Phe Glu Lys Arg Gln Gln Glu Arg Leu Leu Leu
225                 230                 235                 240
Ser Leu Leu Pro Ala His Ile Ala Met Glu Met Lys Ala Glu Ile Ile
                245                 250                 255
Gln Arg Leu Gln Gly Pro Lys Ala Gly Gln Met Glu Asn Thr Asn Asn
            260                 265                 270
Phe His Asn Leu Tyr Val Lys Arg His Thr Asn Val Ser Ile Leu Tyr
        275                 280                 285
Ala Asp Ile Val Gly Phe Thr Arg Leu Ala Ser Asp Cys Ser Pro Gly
    290                 295                 300
Glu Leu Val His Met Leu Asn Glu Leu Phe Gly Lys Phe Asp Gln Ile
305                 310                 315                 320
Ala Lys Glu Asn Glu Cys Met Arg Ile Lys Ile Leu Gly Asp Cys Tyr
                325                 330                 335
Tyr Cys Val Ser Gly Leu Pro Ile Ser Leu Pro Asn His Ala Lys Asn
            340                 345                 350
Cys Val Lys Met Gly Leu Asp Met Cys Glu Ala Ile Lys Lys Val Arg
        355                 360                 365
Asp Ala Thr Gly Val Asp Ile Asn Met Arg Val Gly Val His Ser Gly
    370                 375                 380
Asn Val Leu Cys Gly Val Ile Gly Leu Gln Lys Trp Gln Tyr Asp Val
385                 390                 395                 400
Trp Ser His Asp Val Thr Leu Ala Asn His Met Glu Ala Gly Gly Val
                405                 410                 415
Pro Gly Arg Val His Ile Ser Ser Val Thr Leu Glu His Leu Asn Gly
            420                 425                 430
Ala Tyr Lys Val Glu Glu Gly Asp Gly Asp Ile Arg Asp Pro Tyr Leu
        435                 440                 445
Lys Gln His Leu Val Lys Thr Tyr Phe Val Ile Asn Pro Lys Gly Glu
    450                 455                 460
Arg Arg Ser Pro Gln His Leu Phe Arg Pro Arg His Thr Leu Asp Gly
465                 470                 475                 480
Ala Lys Met Arg Ala Ser Val Arg Met Thr Arg Tyr Leu Glu Ser Trp
                485                 490                 495
Gly Ala Ala Lys Pro Phe Ala His Leu His His Arg Asp Ser Met Thr
            500                 505                 510
```

-continued

```
Thr Glu Asn Gly Lys Ile Ser Thr Thr Asp Val Pro Met Gly Gln His
        515                 520                 525

Asn Phe Gln Asn Arg Thr Leu Arg Thr Lys Ser Gln Lys Lys Arg Phe
        530                 535                 540

Glu Glu Glu Leu Asn Glu Arg Met Ile Gln Ala Ile Asp Gly Ile Asn
545                 550                 555                 560

Ala Gln Lys Gln Trp Leu Lys Ser Glu Asp Ile Gln Arg Ile Ser Leu
                565                 570                 575

Leu Phe Tyr Asn Lys Val Leu Glu Lys Glu Tyr Arg Ala Thr Ala Leu
            580                 585                 590

Pro Ala Phe Lys Tyr Tyr Val Thr Cys Ala Cys Leu Ile Phe Phe Cys
        595                 600                 605

Ile Phe Ile Val Gln Ile Leu Val Leu Pro Lys Thr Ser Val Leu Gly
        610                 615                 620

Ile Ser Phe Gly Ala Ala Phe Leu Leu Ala Phe Ile Leu Phe Val
625                 630                 635                 640

Cys Phe Ala Gly Gln Leu Leu Gln Cys Ser Lys Lys Ala Ser Pro Leu
                645                 650                 655

Leu Met Trp Leu Leu Lys Ser Ser Gly Ile Ile Ala Asn Arg Pro Trp
            660                 665                 670

Pro Arg Ile Ser Leu Thr Ile Ile Thr Thr Ala Ile Ile Leu Met Met
        675                 680                 685

Ala Val Phe Asn Met Phe Phe Leu Ser Asp Ser Glu Glu Thr Ile Pro
        690                 695                 700

Pro Thr Ala Asn Thr Thr Asn Thr Ser Phe Ser Ala Ser Asn Asn Gln
705                 710                 715                 720

Val Ala Ile Leu Arg Ala Gln Asn Leu Phe Phe Leu Pro Tyr Phe Ile
                725                 730                 735

Tyr Ser Cys Ile Leu Gly Leu Ile Ser Cys Ser Val Phe Leu Arg Val
            740                 745                 750

Asn Tyr Glu Leu Lys Met Leu Ile Met Met Val Ala Leu Val Gly Tyr
        755                 760                 765

Asn Thr Ile Leu Leu His Thr His Ala His Val Leu Gly Asp Tyr Ser
        770                 775                 780

Gln Val Leu Phe Glu Arg Pro Gly Ile Trp Lys Asp Leu Lys Thr Met
785                 790                 795                 800

Gly Ser Val Ser Leu Ser Ile Phe Phe Ile Thr Leu Leu Val Leu Gly
                805                 810                 815

Arg Gln Asn Glu Tyr Tyr Cys Arg Leu Asp Phe Leu Trp Lys Asn Lys
            820                 825                 830

Phe Lys Lys Glu Arg Glu Glu Ile Glu Thr Met Glu Asn Leu Asn Arg
        835                 840                 845

Val Leu Leu Glu Asn Val Leu Pro Ala His Val Ala Glu His Phe Leu
        850                 855                 860

Ala Arg Ser Leu Lys Asn Glu Glu Leu Tyr His Gln Ser Tyr Asp Cys
865                 870                 875                 880

Val Cys Val Met Phe Ala Ser Ile Pro Asp Phe Lys Glu Phe Tyr Thr
                885                 890                 895

Glu Ser Asp Val Asn Lys Glu Gly Leu Glu Cys Leu Arg Leu Leu Asn
            900                 905                 910

Glu Ile Ile Ala Asp Phe Asp Asp Leu Leu Ser Lys Pro Lys Phe Ser
        915                 920                 925

Gly Val Glu Lys Ile Lys Thr Ile Gly Ser Thr Tyr Met Ala Ala Thr
```

-continued

```
              930                 935                 940
Gly Leu Ser Ala Val Pro Ser Gln Glu His Ser Gln Glu Pro Glu Arg
945                 950                 955                 960

Gln Tyr Met His Ile Gly Thr Met Val Glu Phe Ala Phe Ala Leu Val
                965                 970                 975

Gly Lys Leu Asp Ala Ile Asn Lys His Ser Phe Asn Asp Phe Lys Leu
                980                 985                 990

Arg Val Gly Ile Asn His Gly Pro Val Ile Ala Gly Val Ile Gly Ala
                995                1000                1005

Gln Lys Pro Gln Tyr Asp Ile Trp Gly Asn Thr Val Asn Val Ala
    1010                1015                1020

Ser Arg Met Asp Ser Thr Gly Val Leu Asp Lys Ile Gln Val Thr
    1025                1030                1035

Glu Glu Thr Ser Leu Val Leu Gln Thr Leu Gly Tyr Thr Cys Thr
    1040                1045                1050

Cys Arg Gly Ile Ile Asn Val Lys Gly Lys Gly Asp Leu Lys Thr
    1055                1060                1065

Tyr Phe Val Asn Thr Glu Met Ser Arg Ser Leu Ser Gln Ser Asn
    1070                1075                1080

Val Ala Ser
    1085

<210> SEQ ID NO 7
<211> LENGTH: 1090
<212> TYPE: PRT
<213> ORGANISM: Rattus norvegicus

<400> SEQUENCE: 7

Met Arg Arg Arg Arg Tyr Leu Arg Asp Arg Ala Glu Ala Ala Ala Ala
1               5                  10                  15

Ala Ala Ala Gly Gly Gly Glu Gly Leu Gln Arg Ser Arg Asp Trp Leu
                20                  25                  30

Tyr Glu Ser Tyr Tyr Cys Met Ser Gln Gln His Pro Leu Ile Val Phe
            35                  40                  45

Leu Leu Leu Ile Val Met Gly Ala Cys Leu Ala Leu Ala Val Phe
        50                  55                  60

Phe Ala Leu Gly Leu Glu Val Glu Asp His Val Ala Phe Leu Ile Thr
65                  70                  75                  80

Val Pro Thr Ala Leu Ala Ile Phe Phe Ala Ile Phe Ile Leu Val Cys
                85                  90                  95

Ile Glu Ser Val Phe Lys Lys Leu Leu Arg Val Phe Ser Leu Val Ile
                100                 105                 110

Trp Ile Cys Leu Val Ala Met Gly Tyr Leu Phe Met Cys Phe Gly Gly
            115                 120                 125

Thr Val Ser Ala Trp Asp Gln Val Ser Phe Phe Leu Phe Ile Ile Phe
        130                 135                 140

Val Val Tyr Thr Met Leu Pro Phe Asn Met Arg Asp Ala Ile Ile Ala
145                 150                 155                 160

Ser Ile Leu Thr Ser Ser Ser His Thr Ile Val Leu Ser Val Tyr Leu
                165                 170                 175

Ser Ala Thr Pro Gly Ala Lys Glu His Leu Phe Trp Gln Ile Leu Ala
            180                 185                 190

Asn Val Ile Ile Phe Ile Cys Gly Asn Leu Ala Gly Ala Tyr His Lys
        195                 200                 205
```

His Leu Met Glu Leu Ala Leu Gln Gln Thr Tyr Arg Asp Thr Cys Asn
210                 215                 220

Cys Ile Lys Ser Arg Ile Lys Leu Glu Phe Glu Lys Arg Gln Gln Glu
225                 230                 235                 240

Arg Leu Leu Leu Ser Leu Leu Pro Ala His Ile Ala Met Glu Met Lys
                245                 250                 255

Ala Glu Ile Ile Gln Arg Leu Gln Gly Pro Lys Ala Gly Gln Met Glu
            260                 265                 270

Asn Thr Asn Asn Phe His Asn Leu Tyr Val Lys Arg His Thr Asn Val
        275                 280                 285

Ser Ile Leu Tyr Ala Asp Ile Val Gly Phe Thr Arg Leu Ala Ser Asp
    290                 295                 300

Cys Ser Pro Gly Glu Leu Val His Met Leu Asn Glu Leu Phe Gly Lys
305                 310                 315                 320

Phe Asp Gln Ile Ala Lys Glu Asn Glu Cys Met Arg Ile Lys Ile Leu
                325                 330                 335

Gly Asp Cys Tyr Tyr Cys Val Ser Gly Leu Pro Ile Ser Leu Pro Asn
            340                 345                 350

His Ala Lys Asn Cys Val Lys Met Gly Leu Asp Met Cys Glu Ala Ile
        355                 360                 365

Lys Lys Val Arg Asp Ala Thr Gly Val Asp Ile Asn Met Arg Val Gly
    370                 375                 380

Val His Ser Gly Asn Val Leu Cys Gly Val Ile Gly Leu Gln Lys Trp
385                 390                 395                 400

Gln Tyr Asp Val Trp Ser His Asp Val Thr Leu Ala Asn His Met Glu
                405                 410                 415

Ala Gly Gly Val Pro Gly Arg Val His Ile Ser Ser Val Thr Leu Glu
            420                 425                 430

His Leu Asn Gly Ala Tyr Lys Val Glu Glu Gly Asp Gly Glu Ile Arg
        435                 440                 445

Asp Pro Tyr Leu Lys Gln His Leu Val Lys Thr Tyr Phe Val Ile Asn
    450                 455                 460

Pro Lys Gly Glu Arg Arg Ser Pro Gln His Leu Phe Arg Pro Arg His
465                 470                 475                 480

Thr Leu Asp Gly Ala Lys Met Arg Ala Ser Val Arg Met Thr Arg Tyr
                485                 490                 495

Leu Glu Ser Trp Gly Ala Ala Lys Pro Phe Ala His Leu His His Arg
            500                 505                 510

Asp Ser Met Thr Thr Glu Asn Gly Lys Ile Ser Thr Thr Asp Val Pro
    515                 520                 525

Met Gly Gln His Asn Phe Gln Asn Arg Thr Leu Arg Thr Lys Ser Gln
530                 535                 540

Lys Lys Arg Phe Glu Glu Glu Leu Asn Glu Arg Met Ile Gln Ala Ile
545                 550                 555                 560

Asp Gly Ile Asn Ala Gln Lys Gln Trp Leu Lys Ser Glu Asp Ile Gln
                565                 570                 575

Arg Ile Ser Leu Leu Phe Tyr Asn Lys Asn Ile Glu Lys Glu Tyr Arg
            580                 585                 590

Ala Thr Ala Leu Pro Ala Phe Lys Tyr Tyr Val Thr Cys Ala Cys Leu
        595                 600                 605

Ile Phe Leu Cys Ile Phe Ile Val Gln Ile Leu Val Leu Pro Lys Thr
    610                 615                 620

Ser Ile Leu Gly Phe Ser Phe Gly Ala Ala Phe Leu Ser Leu Ile Phe

```
              625                 630                 635                 640
Ile Leu Phe Val Cys Phe Ala Gly Gln Leu Leu Gln Cys Ser Lys Lys
                    645                 650                 655
Ala Ser Thr Ser Leu Met Trp Leu Leu Lys Ser Ser Gly Ile Ile Ala
                    660                 665                 670
Asn Arg Pro Trp Pro Arg Ile Ser Leu Thr Ile Val Thr Thr Ala Ile
                    675                 680                 685
Ile Leu Thr Met Ala Val Phe Asn Met Phe Phe Leu Ser Asn Ser Glu
                    690                 695                 700
Glu Thr Thr Leu Pro Thr Ala Asn Thr Ser Asn Ala Asn Val Ser Val
705                 710                 715                 720
Pro Asp Asn Gln Ala Ser Ile Leu His Ala Arg Asn Leu Phe Phe Leu
                    725                 730                 735
Pro Tyr Phe Ile Tyr Ser Cys Ile Leu Gly Leu Ile Ser Cys Ser Val
                    740                 745                 750
Phe Leu Arg Val Asn Tyr Glu Leu Lys Met Leu Ile Met Met Val Ala
                    755                 760                 765
Leu Val Gly Tyr Asn Thr Ile Leu Leu His Thr His Ala His Val Leu
                    770                 775                 780
Asp Ala Tyr Ser Gln Val Leu Phe Gln Arg Pro Gly Ile Trp Lys Asp
785                 790                 795                 800
Leu Lys Thr Met Gly Ser Val Ser Leu Ser Ile Phe Phe Ile Thr Leu
                    805                 810                 815
Leu Val Leu Gly Arg Gln Ser Glu Tyr Tyr Cys Arg Leu Asp Phe Leu
                    820                 825                 830
Trp Lys Asn Lys Phe Lys Lys Glu Arg Glu Glu Ile Glu Thr Met Glu
                    835                 840                 845
Asn Leu Asn Arg Val Leu Leu Glu Asn Val Leu Pro Ala His Val Ala
850                 855                 860
Glu His Phe Leu Ala Arg Ser Leu Lys Asn Glu Glu Leu Tyr His Gln
865                 870                 875                 880
Ser Tyr Asp Cys Val Cys Val Met Phe Ala Ser Ile Pro Asp Phe Lys
                    885                 890                 895
Glu Phe Tyr Thr Glu Ser Asp Val Asn Lys Glu Gly Leu Glu Cys Leu
                    900                 905                 910
Arg Leu Leu Asn Glu Ile Ile Ala Asp Phe Asp Asp Leu Leu Ser Lys
                    915                 920                 925
Pro Lys Phe Ser Gly Val Glu Lys Ile Lys Thr Ile Gly Ser Thr Tyr
                    930                 935                 940
Met Ala Ala Thr Gly Leu Ser Ala Ile Pro Ser Gln Glu His Ala Gln
945                 950                 955                 960
Glu Pro Glu Arg Gln Tyr Met His Ile Gly Thr Met Val Glu Phe Ala
                    965                 970                 975
Tyr Ala Leu Val Gly Lys Leu Asp Ala Ile Asn Lys His Ser Phe Asn
                    980                 985                 990
Asp Phe Lys Leu Arg Val Gly Ile Asn His Gly Pro Val Ile Ala Gly
                    995                 1000                1005
Val Ile Gly Ala Gln Lys Pro Gln Tyr Asp Ile Trp Gly Asn Thr
                    1010                1015                1020
Val Asn Val Ala Ser Arg Met Asp Ser Thr Gly Val Leu Asp Lys
                    1025                1030                1035
Ile Gln Val Thr Glu Glu Thr Ser Leu Ile Leu Gln Thr Leu Gly
                    1040                1045                1050
```

-continued

```
Tyr Thr Cys Thr Cys Arg Gly Ile Ile Asn Val Lys Gly Lys Gly
    1055            1060                1065

Asp Leu Lys Thr Tyr Phe Val Asn Thr Glu Met Ser Arg Ser Leu
    1070            1075                1080

Ser Gln Ser Asn Leu Ala Ser
    1085            1090
```

REGULATION OF HUMAN ADENYLATE CYCLASE

This application is a National Stage application of co-pending PCT application PCT/EP01/13060 filed Nov. 12, 2001, which was published in English under PCT Article 21(2) on May 16, 2002, which claims the benefit of U.S. provisional application Ser. No. 60/247,005 filed Nov. 13, 2000 and Ser. No. 60/267,181 filed Feb. 8, 2001. These applications are incorporated herein by reference in their entireties.

TECHNICAL FIELD OF THE INVENTION

The invention relates to a novel human adenylate cyclase and its regulation for therapeutic uses.

BACKGROUND OF THE INVENTION

Cyclases play important roles in the transduction of extracellular signals via their synthesis of "secondary messengers" such as adenosine 3', 5'-cyclic phosphate (cyclic adenosine monophosphate, cAMP) and guanosine 3', 5'-cyclic phosphate (cyclic guanosine monophosphate, cGMP). Cell surface receptors mediate the transduction of an extracellular signal, such as the binding of a ligand to a receptor, into a signal that is transmitted internally within the cell. The internal signal is carried by secondary messengers, which typically are produced in response to the binding of an external signal. The secondary messengers in turn activate particular proteins and other regulators within the cell which have the potential to regulate expression of specific genes or to alter a metabolic process.

Cyclic AMP and cGMP play important roles in the regulation of a multitude of cellular activities. For example, cAM responds to cellular signals through a specific protein kinase (cAMP-dependent protein kinase or protein kinase A) to phosphorylate target molecules, e.g., other protein kinases or proteins involved in transport or cellular morphology. Through stimulation of the kinase, intracellular cAMP mediates many of the effects of hormones in the regulation of cellular metabolism and cell growth. Cyclic GMP also acts as an intracellular messenger, for example, by activating cGMP-dependent kinases and regulating cGMP sensitive ion channels. The role of cGMP as a secondary messenger has been well established in vascular smooth muscle relaxation and retinal phototransduction.

Adenylate Cyclase

The synthesis of cAMP from adenosine triphosphate (ATP) is catalyzed by adenylate cyclase (also referred to as adenylyl cyclase and adenyl cyclase). In mammalian cells, adenylate cyclase is usually an integral membrane protein. Adenylate cyclase activity may be affected by a factor/receptor binding event transmitted through an associated G protein. Interaction of several different external factors with their distinct receptors causes alterations in cAMP intracellular concentration (Broach et al., U.S. Pat. No. 6,001,553). Different receptors are associated with their own particular G-protein intermediary, which itself is associated with adenylate cyclase.

At least nine distinct isoenzymes of mammalian adenylate cyclase have been identified and are designated as adenylate cyclases types 1–9 (Antoni et al., U.S. Pat. No. 6,090,612). These adenylate cyclases have a general structure consisting of 12 transmembrane helices and two cytoplasmic, catalytic domains (Hurley, 1998, Curr. Opin. Struct. Biol. 8:770–77). Some of these enzymes have been analyzed functionally and appear to confer unique signal processing capacities to cells (Taussig et al., 1995, J. Biol. Chem. 270:1–4).

In addition to functional diversity, adenylate cyclase isozymes have distinct tissue distribution profiles (Iyengar, U.S. Pat. No. 6,034,071). Localization studies using mRNA probes have been used to determine tissue distribution of the various adenylate cyclases (Pieroni et al., 1993, Curr. Opin. Neurobiol. 3: 345–351). Adenylate cyclase type 1 (AC 1) appears to be present only in neuronal tissue, whereas AC 2 has been found in brain and lung. AC 3 has been localized in olfactory neurons as well as other neuronal and non-neuronal tissues (Glatt and Snyder, 1993, Nature 361: 536–538; Xia et al., 1992, Neurosci. Lett. 144: 169–173). AC 4 appears to be present at very low levels in brain, and throughout most tissues. AC 5 and AC 6 have also been found to be widely distributed (Premont et al., 1992, Proc. Natl. Acad. Sci. U.S.A. 89: 9809–9813; Krupinski et al., 1992, J. Biol. Chem. 267: 24858–24862) although AC 6 seems to be of very low abundance in the brain. AC 5 is particularly abundant in the heart and in some regions of the brain. AC 7 appears to be widely distributed, but may be scarce in the brain. AC 8, like AC 1, seems to be abundant in the brain. Within the brain, the distributions of AC 1, AC 2, AC 3, AC 5 and AC 8 show distinct regional patterns. Collectively, these observations indicate that the particular adenylate cyclase isotype profile of a cell is fundamentally important with respect to cellular function.

Association with Disease

The wide variety of cyclases that have been identified thus far, together with their differing tissue distributions, demonstrate the importance of particular cellular cyclase profiles and their roles in signal transduction with respect to cellular function. Alterations in the levels of cyclic nucleotide intracellular (or secondary) messenger levels that result from alterations in particular cyclase activities have been implicated in a wide range of conditions and diseases, including cardiovascular disease, diseases of the central nervous system, intestinal conditions, retinal diseases, and shock. For instance, the high distribution of adenylate cyclases in brain has been correlated with a likely role for adenylate cyclases in neurological disorders such as Alzheimer's disease and Parkinson's disease. The high distribution of adenylate cyclase in the heart is likely to contribute to cardiovascular diseases, such as angina and hypertension.

Regulation of cyclases, therefore, has important implications for treatment of many conditions and diseases. Particular beneficial cellular responses may be elicited by blocking or stimulating the activity of particular cyclases. The many cyclases known to date and their wide distribution, coupled with their specific responses to a large number of extracellular signaling molecules, indicates that there are likely to be many more cyclases to be identified. Thus, there is a need in the art for identifying new cyclases and methods of regulating cyclase activity to provide therapeutic effects.

SUMMARY OF THE INVENTION

It is an object of the invention to provide reagents and methods of regulating a human adenylate cyclase. This and other objects of the invention are provided by one or more of the embodiments described below.

One embodiment of the invention is a adenylate cyclase polypeptide comprising an amino acid sequence selected from the group consisting of:
amino acid sequences which are at least about 95% identical to the amino acid sequence shown in SEQ ID NO: 6; and
the amino acid sequence shown in SEQ ID NO:6.

Yet another embodiment of the invention is a method of screening for agents which decrease extracellular matrix degradation. A test compound is contacted with a adenylate cyclase polypeptide comprising an amino acid sequence selected from the group consisting of:
amino acid sequences which are at least about 95% identical to the amino acid sequence shown in SEQ ID NO: 6; and
the amino acid sequence shown in SEQ ID NO:6.

Binding between the test compound and the adenylate cyclase polypeptide is detected. A test compound which binds to the adenylate cyclase polypeptide is thereby identified as a potential agent for decreasing extracellular matrix degradation. The agent can work by decreasing the activity of the adenylate cyclase.

Another embodiment of the invention is a method of screening for agents which decrease extracellular matrix degradation. A test compound is contacted with a polynucleotide encoding a adenylate cyclase polypeptide, wherein the polynucleotide comprises a nucleotide sequence selected from the group consisting of:
nucleotide sequences which are at least about 50% identical to the nucleotide sequence shown in SEQ ID NO: 4;
the nucleotide sequence shown in SEQ ID NO:4;
nucleotide sequences which are at least about 50% identical to the nucleotide sequence shown in SEQ ID NO: 5; and
the nucleotide sequence shown in SEQ ID NO:5.

Binding of the test compound to the polynucleotide is detected. A test compound which binds to the polynucleotide is identified as a potential agent for decreasing extracellular matrix degradation. The agent can work by decreasing the amount of the adenylate cyclase through interacting with the adenylate cyclase mRNA.

Another embodiment of the invention is a method of screening for agents which regulate extracellular matrix degradation. A test compound is contacted with a adenylate cyclase polypeptide comprising an amino acid sequence selected from the group consisting of:
amino acid sequences which are at least about 95% identical to the amino acid sequence shown in SEQ ID NO: 6; and
the amino acid sequence shown in SEQ ID NO:6.

A adenylate cyclase activity of the polypeptide is detected. A test compound which increases adenylate cyclase activity of the polypeptide relative to adenylate cyclase activity in the absence of the test compound is thereby identified as a potential agent for increasing extracellular matrix degradation. A test compound which decreases adenylate cyclase activity of the polypeptide relative to adenylate cyclase activity in the absence of the test compound is thereby identified as a potential agent for decreasing extracellular matrix degradation.

Even another embodiment of the invention is a method of screening for agents which decrease extracellular matrix degradation. A test compound is contacted with a adenylate cyclase product of a polynucleotide which comprises a nucleotide sequence selected from the group consisting of:
nucleotide sequences which are at least about 50% identical to the nucleotide sequence shown in SEQ ID NO: 4;
the nucleotide sequence shown in SEQ ID NO:4;
nucleotide sequences which are at least about 50% identical to the nucleotide sequence shown in SEQ ID NO: 5; and
the nucleotide sequence shown in SEQ ID NO:5.

Binding of the test compound to the adenylate cyclase product is detected. A test compound which binds to the adenylate cyclase product is thereby identified as a potential agent for decreasing extracellular matrix degradation.

Still another embodiment of the invention is a method of reducing extracellular matrix degradation. A cell is contacted with a reagent which specifically binds to a polynucleotide encoding a adenylate cyclase polypeptide or the product encoded by the polynucleotide, wherein the polynucleotide comprises a nucleotide sequence selected from the group consisting of:
nucleotide sequences which are at least about 50% identical to the nucleotide sequence shown in SEQ ID NO: 4;
the nucleotide sequence shown in SEQ ID NO:4;
nucleotide sequences which are at least about 50% identical to the nucleotide sequence shown in SEQ ID NO: 5; and
the nucleotide sequence shown in SEQ ID NO:5.

Adenylate cyclase activity in the cell is thereby decreased.

Still another embodiment of the invention is a method for treating disease. An effective amount of a pharmaceutical composition comprising a reagent that modulates the activity of a human adenylate cyclase or an expression vector comprising a polynucleotide encoding a human adenylate cyclase and a pharmaceutically acceptable carrier is administered to a subject in need of such treatment.

BRIEF DESCRIPTION OF THE DRAWINGS

FIG. 1 shows the DNA-sequence (bp 1-2664 from KIAA1060) encoding the C-terminal part of an adenylate cyclase polypeptide (SEQ ID NO:1).

FIG. 2 shows the amino acid sequence deduced from the DNA-sequence of FIG. 1 (SEQ ID NO:3).

FIG. 3 shows a DNA-sequence encoding a novel full-length adenylate cyclase polypeptide (SEQ ID NO:4).

FIG. 4 shows the amino acid sequence deduced from the DNA-sequence of FIG. 3 (SEQ ID NO:6).

FIG. 5 shows the genomic DNA-sequence (KIAA1060) habouring a partial CDS for the C-terminal part of an adenylate cyclase polypeptide (SEQ ID NO:2).

FIG. 6 shows the genomic DNA-sequence habouring the full CDS for the novel adenylate cyclase polypeptide (SEQ ID NO:5).

FIG. 7 shows the amino acid sequence of the protein identified by SwissProt Accession No. P26769 (SEQ ID NO:7).

FIG. 8 shows the BLASTP alignment of human adenylate cyclase (SEQ ID NO:2 or 4) with the protein identified with SwissProt Accession No. P26769 (SEQ ID NO:7).

FIG. 9 shows the Prosite search results.

FIG. 10 shows the Transmembrane helices.

FIG. 11 shows the BLOCKS search results.

FIG. 12 shows the HMMPFAM—alignment of 129L_protein (SEQ ID NO:2 or 4) against pfam|hmm|guanylate_cyc.

FIG. 13 shows the BLASTP—alignment of 129L_protein (SEQ ID NO:2 or 4) against pdb|1CJK|1CJK-B.

FIG. 14 shows the relative expression of the novel adenylate cyclase in various tissues as determined by RT-PCR with gene specific primers and human cDNA derived from tissue as template in a standard procedure as known to those of skill in the art (described e.g. in EXAMPLE 6). The cDNA of the adenylate cyclase is detected in many phage libraries reflecting the expression in a variety of different human tissues. Especially interesting is the expression in different regions of the nervous system like brain frontal cortex and spinal cord which emphasize the importance of adenylate cyclase in nervous system disorders such as primary and secondary disorders after brain injury, disorders of mood, anxiety disorders, disorders of thought and volition, disorders of sleep and wakefulness, diseases of the motor unit, such as neurogenic and myopathic disorders, neurodegenerative disorders such as Alzheimer's and Parkinson's disease, and processes of peripheral and chronic pain.

FIG. 15 shows the relative expression of the novel adenylate cyclase in various tissues as determined by RT-PCR with gene specific primers and human phage libraries as template in a standard procedure as known to those of skill in the art (described e.g. in EXAMPLE 6). The following tissues are represented: Lane 1-Liver, lane 2-Skeletal Muscle, lane 3-Hypothalamus, lane 4-Islets, lane 5-Adipose Sub., lane 6-Adipose Mes., lane 7-Genomic DNA, lane 8-No amplification control. Expression is shown in lanes 2–7.

FIG. 16 shows the relative expression of the novel adenylate cyclase in various tissues as determined by RT-PCR (Taqman). By far the highest level of expression was detected in fetal and adult brain and muscle (FIG. 16a). Detailed expression analysis reveals strong expression in aortha (FIG. 16b) and a variety of central and peripheral CNS tissues The CNS specific expression of the adenylate cyclase indicates the possibility to treat various disorders of the nervous system.

DETAILED DESCRIPTION OF THE INVENTION

The invention relates to an isolated polynucleotide encoding a adenylate cyclase polypeptide and being selected from the group consisting of:
a) a polynucleotide encoding a adenylate cyclase polypeptide comprising an amino acid sequence selected from the group consisting of:
amino acid sequences which are at least about 95% identical to the amino acid sequence shown in SEQ ID NO: 6; and
the amino acid sequence shown in SEQ ID NO: 6.
b) a polynucleotide comprising the sequence of SEQ ID NO: 4 or 5;
c) a polynucleotide which hybridizes under stringent conditions to a polynucleotide specified in (a) and (b);
d) a polynucleotide the sequence of which deviates from the polynucleotide sequences specified in (a) to (c) due to the degeneration of the genetic code; and
e) a polynucleotide which represents a fragment, derivative or allelic variation of a polynucleotide sequence specified in (a) to (d).

Furthermore, it has been discovered by the present applicant that a novel adenylate cyclase, particularly a human adenylate cyclase, is a discovery of the present invention. Human adenylate cyclase comprises the amino acid sequence shown in SEQ ID NO:6. Genomic sequences are located on chromosome 5. A coding sequence is shown in SEQ ID NO:4. The genomic sequence harbouring the CDS is shown in SEQ ID NO:5.

Related ESTs [embl|AI160340 (757 bp), embl|AI932389 (753 bp), genbank|AW967221 (679 bp), embl|AA740541 (663 bp), embl|AWO55133 (613 bp), embl|N45141 (614 bp), embl|AW383741 (612 bp), embl|AI095516 (513 bp), embl|AA627327 (579 bp), embl|AI095516 (475 bp), embl|AI953690 (469 bp), genbank|AW964324 (576 bp), embl|AW390690 (463 bp), embl|AA192182 (447 bp), embl|AWO89615 (392 bp), embl|AA194354 (472 bp), embl|AW196770 (387 bp), embl|AI003215 (416 bp), embl|R12094 (477 bp), embl|T08791 (369 bp), embl|T28852 (36lbp), embl|F22273 (430 bp), embl|R15999 (488 bp), embl|T80236 (452 bp), embl|AA224380 (393 bp), embl|T08790 (329 bp), genbank|AW901183 (348 bp), embl|H99998 (322 bp), embl|R35910 (466 bp), embl|AA913393 (304 bp), embl|R49430 (366 bp), embl|F01263 (291 bp), embl|AI703261 (278 bp), embl|AI694341 (287 bp), embl|AA913243 (256 bp), embl|AA913847 (248 bp), embl|AL120054 (384 bp)] are expressed in fetal heart; pooled fetal lung, testis and B cells; pooled kidney tumors; pooled glioblastoma; multiple sclerosis lesions; head and neck; pregnant uterus; breast; pooled germ cell tumors; stomach; skeletal muscle; pooled brain tumors; schizophrenic brain S-11 frontal lobe; infant brain; neuroepithelial cells; melanocyte; lung carcinoid; amygdala.

Human adenylate cyclase is 95% identical over 1090 amino acids to the rat protein identified with SwissProt Accession No. P26769 and annotated as "ADENYLATE CYCLASE, TYPE II (EC 4.6.1.1)" (FIG. 45).

Human adenylate cyclase of the invention is expected to be useful for the same purposes as previously identified adenylate cyclase enzymes. Human adenylate cyclase is believed to be useful in therapeutic methods to treat disorders such as peripheral and central nervous system disorders, disorders of the genito-urinary system including but not limited to benign prostatic hyperplasia and urinary incontinence, obesity, COPD and diabetes. Human adenylate cyclase also can be used to screen for human adenylate cyclase activators and inhibitors.

Polypeptides

Human adenylate cyclase polypeptides according to the invention comprise at least 6, 10, 15, 20, 25, 50, 75, 100, 125, 150, 175, 200, 250, 300, 350, 400, 450, 500, 550, 600, 650, 700, 750, 800, 850, 900, 950, 1000, 1050, or 1086 contiguous amino acids selected from SEQ ID NO:6 or a biologically active variant thereof, as defined below. A adenylate cyclase polypeptide of the invention therefore can be a portion of a adenylate cyclase protein, a full-length adenylate cyclase protein, or a fusion protein comprising all or a portion of a adenylate cyclase protein.

Biologically Active Variants

Human adenylate cyclase polypeptide variants which are biologically active, e.g., retain an adenylate cyclase activity, also are adenylate cyclase polypeptides. Preferably, naturally or non-naturally occurring adenylate cyclase polypeptide variants have amino acid sequences which are at least about 95, 96, 96, or 98% identical to the amino acid sequence shown in SEQ ID NO:6 or a fragment thereof. Percent identity between a putative adenylate cyclase polypeptide variant and an amino acid sequence of SEQ ID NO:6 is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant. The FASTA algorithm is described by Pearson and Lipman, Proc. Nat'l Acad. Sci. USA 85:2444(1988), and by Pearson, Meth. Enzymol. 183:63 (1990). Briefly, FASTA first characterizes sequence similarity by identifying regions shared by the query sequence (e.g. SEQ ID NO: 6) and a test sequence that have either the highest density of identities (if the ktup variable is 1) or pairs of identities (if ktup=2), without considering conservative amino acidsubstitutions, insertions, or deletions. The ten regions with the highest density of identities are then rescored by comparing the similarity of all paired amino acids using anamino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup=1, gapopening-penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990). FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a adenylate cyclase polypeptide can be found using computer programs well known in the art, such as DNASTAR software. Whether an amino acid change results in a biologically active adenylate cyclase polypeptide can readily be determined by assaying for adenylate cyclase activity, as described for example, in U.S. Pat. No. 5,795,756.

Fusion Proteins

Fusion proteins are useful for generating antibodies against adenylate cyclase polypeptide amino acid sequences and for use in various assay systems. For example, fusion proteins can be used to identify proteins which interact with portions of a adenylate cyclase polypeptide. Protein affinity chromatography or library-based assays for protein-protein interactions, such as the yeast two-hybrid or phage display systems, can be used for this purpose. Such methods are well known in the art and also can be used as drug screens.

A adenylate cyclase polypeptide fusion protein comprises two polypeptide segments fused together by means of a peptide bond. The first polypeptide segment comprises at least 6, 10, 15, 20, 25, 50, 75, 100, 125, 150, 175, 200, 250, 300, 350, 400, 450, 500, 550, 600, 650, 700, 750, 800, 850, or 887 contiguous amino acids selected from SEQ ID NO:3 or at least 6, 10, 15, 20, 25, 50, 75, 100, 125, 150, 175, 200, 250, 300, 350; 400, 450, 500, 550, 600, 650, 700, 750, 800, 850, 900, 950, 1000, 1050, or 1086 contiguous amino acids selected from SEQ ID NO:6 or of a biologically active variant, such as those described above. The first polypeptide segment also can comprise full-length adenylate cyclase protein.

The second polypeptide segment can be a full-length protein or a protein fragment. Proteins commonly used in fusion protein construction include β-galactosidase, β-glucuronidase, green fluorescent protein (GFP), auto fluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the adenylate cyclase polypeptide-encoding sequence and the heterologous protein sequence, so that the adenylate cyclase polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from the complement of SEQ ID NO:4, or 5 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human adenylate cyclase polypeptide can be obtained using adenylate cyclase polypeptide polynucleotides (described below) to make suitable probes or primers for screening cDNA expression libraries from other species, such as mice, monkeys, or yeast, identifying cDNAs which encode homologs of adenylate cyclase polypeptide, and expressing the cDNAs as is known in the art.

Polynucleotides

A adenylate cyclase polynucleotide can be single- or double-stranded and comprises a coding sequence or the complement of a coding sequence for a adenylate cyclase polypeptide. Coding sequences for human adenylate cyclase are shown in SEQ ID NOS: 4 and 5.

Degenerate nucleotide sequences encoding human adenylate cyclase polypeptides, as well as homologous nucleotide sequences which are at least about 50, 55, 60, 65, 70, preferably about 75, 90, 96, or 98% identical to the nucleotide sequence shown in SEQ ID NOS:4 and 5 or their complements also are adenylate cyclase polynucleotides.

Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of adenylate cyclase polynucleotides which encode biologically active adenylate cyclase polypeptides also are adenylate cyclase polynucleotides. Polynucleotide fragments comprising 8, 10, 12, 15, 18, 20, 25, 50, 75, 100, 200, 300, 400, or 500 contiguous nucleotides selected from SEQ ID NO:4 or 5 or their complements also are adenylate cyclase polynucleotides.

Identification of Polynucleotide Variants and Homologs

Variants and homologs of the adenylate cyclase polynucleotides described above also are adenylate cyclase polynucleotides. Typically, homologous adenylate cyclase polynucleotide sequences can be identified by hybridization of candidate polynucleotides to known adenylate cyclase polynucleotides under stringent conditions, as is known in the art. For example, using the following wash conditions—2× SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the adenylate cyclase polynucleotides disclosed herein also can be identified by making suitable probes or primers and screening cDNA expression libraries from other species, such as mice, monkeys, or yeast. Human variants of adenylate cyclase polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human adenylate cyclase polynucleotides or adenylate cyclase polynucleotides of other species can therefore be identified by hybridizing a putative homologous adenylate cyclase polynucleotide with a polynucleotide having a nucleotide sequence of SEQ ID NO: 4 or 5 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to adenylate cyclase polynucleotides or their complements following stringent hybridization and/or wash conditions also are adenylate cyclase polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a adenylate cyclase polynucleotide having a nucleotide sequence shown in SEQ ID NO:4 or 5 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci U.S.A.* 48, 1390 (1962):

$$T_m = 81.5°\text{ C.} - 16.6(\log_{10}[\text{Na}^+]) + 0.41(\%G+C) - 0.63(\% \text{ formamide}) - 600/l), \text{ where } l = \text{the length of the hybrid in basepairs.}$$

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A adenylate cyclase polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated adenylate cyclase polynucleotides. For example, restriction enzymes and probes can be used to isolate polynucleotide fragments which comprises adenylate cyclase nucleotide sequences. Isolated polynucleotides are in preparations which are free or at least 70, 80, or 90% free of other molecules.

Human adenylate cyclase cDNA molecules can be made with standard molecular biology techniques, using adenylate cyclase mRNA as a template. Human adenylate cyclase cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesizes adenylate cyclase polynucleotides. The degeneracy of the genetic code allows alternate nucleotide sequences to be synthesized which will en code a adenylate cyclase polypeptide having, for example, an amino acid sequence shown in SEQ ID NO: 6 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Human adenylate cyclase polypeptides can be obtained, for example, by purification from human cells, by expression of adenylate cyclase polynucleotides, or by direct chemical synthesis.

Protein Purification

Human adenylate cyclase polypeptides can be purified from any cell which expresses the enzyme, including host cells which have been transfected with adenylate cyclase expression constructs. A purified adenylate cyclase polypeptide is separated from other compounds which normally associate with the adenylate cyclase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified adenylate cyclase polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a adenylate cyclase polynucleotide, the polynucleotide can be inserted into an expression vector which contains the necessary elements for the transcription and translation of the inserted coding sequence. Methods which are well known to those skilled in the art can be used to construct expression vectors containing sequences encoding adenylate cyclase polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a adenylate cyclase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a adenylate cyclase polypeptide, vectors based on SV40 or EBV can be used with an appropriate selectable marker.

Bacterial and Yeast Expression Systems

In bacterial systems, a number of expression vectors can be selected depending upon the use intended for the adenylate cyclase polypeptide. For example, when a large quantity of a adenylate cyclase polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the adenylate cyclase polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding adenylate cyclase polypeptides can be driven by any of a number of promoters. For example, viral promoters such as the $^{35}$S and 19S promoters of CaMV can be used alone or in combination, with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, McGraw Hill, New York, N.Y., pp. 191–196, 1992).

An insect system also can be used to express a adenylate cyclase polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding adenylate cyclase polypeptides can be cloned into a non-essential region of the virus, such as the polyhedrin gene, and placed under control of the polyhedrin promoter. Successful insertion of adenylate cyclase polypeptides will render the polyhedrin gene inactive and produce recombinant virus lacking coat protein. The recombinant viruses can then be used to infect *S. frugiperda* cells or *Trichoplusia* larvae in which adenylate cyclase polypeptides can be expressed (Engelhard et al., *Proc. Nat. Acad. Sci.* 91, 3224–3227, 1994).

Mammalian Expression Systems

A number of viral-based expression systems can be used to express adenylate cyclase polypeptides in mammalian host cells. For example, if an adenovirus is used as an expression vector, sequences encoding adenylate cyclase polypeptides can be ligated into an adenovirus transcription/translation complex comprising the late promoter and tripartite leader sequence. Insertion in a non-essential E1 or E3 region of the viral genome can be used to obtain a viable virus which is capable of expressing a adenylate cyclase polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding adenylate cyclase polypeptides. Such signals include the ATG initiation codon and adjacent sequences. In cases where sequences encoding a adenylate cyclase polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed adenylate cyclase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express adenylate cyclase polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced adenylate cyclase sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk or aprf cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G-418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the adenylate cyclase polynucleotide is also present, its presence and expression may need to be conformed. For example, if a sequence encoding a adenylate cyclase polypeptide is inserted within a marker gene sequence, transformed cells containing sequences which encode a adenylate cyclase polypeptide can be identified by the absence of marker gene function. Alternatively, a marker gene can be placed in tandem with a sequence encoding a adenylate cyclase polypeptide under the control of a single promoter. Expression of the marker gene in response to induction or selection usually indicates expression of the adenylate cyclase polynucleotide.

Alternatively, host cells which contain a adenylate cyclase polynucleotide and which express a adenylate cyclase polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding a adenylate cyclase polypeptide can be detected by DNA-DNA or DNA-RNA hybridization or amplification using probes or fragments or fragments of polynucleotides encoding a adenylate cyclase polypeptide. Nucleic acid amplification-based assays involve the use of oligonucleotides selected from sequences encoding a adenylate cyclase polypeptide to detect transformants which contain a adenylate cyclase polynucleotide.

A variety of protocols for detecting and measuring the expression of a adenylate cyclase polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a adenylate cyclase polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding adenylate cyclase polypeptides include oligolabeling, nick translation, end-labeling, or PCR amplification using a labeled nucleotide. Alternatively, sequences encoding a adenylate cyclase polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a adenylate cyclase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode adenylate cyclase polypeptides can be designed to contain signal sequences which direct secretion of soluble adenylate cyclase polypeptides through a prokaryotic or eukaryotic cell membrane or which direct the membrane insertion of membrane-bound adenylate cyclase polypeptide.

As discussed above, other constructions can be used to join a sequence encoding a adenylate cyclase polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the adenylate cyclase polypeptide also can be used to facilitate purification. One such expression vector provides for expression of a fusion protein containing a adenylate cyclase polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the adenylate cyclase polypeptide from the fusion protein. Vectors which contain fusion proteins are disclosed in Kroll et al., *DNA Cell Biol.* 12, 441–453, 1993.

Chemical Synthesis

Sequences encoding a adenylate cyclase polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a adenylate cyclase polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of adenylate cyclase polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic adenylate cyclase polypeptide can be confirmed by amino acid analysis or sequencing (e.g., the Edman degradation procedure; see Creighton, supra). Additionally, any portion of the amino acid sequence of the adenylate cyclase polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce adenylate cyclase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter adenylate cyclase polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a adenylate cyclase polypeptide. "Antibody" as used herein includes intact immunoglobulin molecules, as well as fragments thereof, such as Fab, F(ab')$_2$, and Fv, which are capable of binding an epitope of a adenylate cyclase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a adenylate cyclase polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a adenylate cyclase polypeptide provides a detection signal at least 5-, 10-, or 20-fold higher than a detection signal provided with other proteins when used in an immunochemical assay. Preferably, antibodies which specifically bind to adenylate cyclase polypeptides do not detect other proteins in immunochemical assays and can immunoprecipitate a adenylate cyclase polypeptide from solution.

Human adenylate cyclase polypeptides can be used to immunize a mammal, such as a mouse, rat, rabbit, guinea pig, monkey, or human, to produce polyclonal antibodies. If desired, a adenylate cyclase polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to a adenylate cyclase polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to a adenylate cyclase polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to adenylate cyclase polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to adenylate cyclase polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a adenylate cyclase polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of adenylate cyclase gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of adenylate cyclase gene expression can be obtained by designing antisense oligonucleotides which will form duplexes to the control, 5', or regulatory regions of the adenylate cyclase gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a adenylate cyclase polynucleotide. Antisense oligonucleotides which comprise, for example, 2, 3, 4, or 5 or more stretches of contiguous nucleotides which are precisely complementary to a adenylate cyclase polynucleotide, each separated by a stretch of contiguous nucleotides which are not complementary to adjacent adenylate cyclase nucleotides, can provide sufficient targeting specificity for adenylate cyclase mRNA. Preferably, each stretch of complementary contiguous nucleotides is at least 4, 5, 6, 7, or 8 or more nucleotides in length. Non-coplementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular adenylate cyclase polynucleotide sequence.

Antisense oligonucleotides can be modified without affecting their ability to hybridize to a adenylate cyclase polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a adenylate cyclase polynucleotide can be used to generate ribozymes which will specifically bind to mRNA transcribed from the adenylate cyclase polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a adenylate cyclase RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate adenylate cyclase RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease adenylate cyclase expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human adenylate cyclase. Such genes may represent genes which are differentially expressed in disorders including, but not limited to, peripheral and central nervous system disorders, disorders of the genito-urinary system including but not limited to benign prostatic hyperplasia and urinary incontinence, obesity, COPD and diabetes. Further, such genes may represent genes which are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human adenylate cyclase gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique which does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples which represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., *Nature* 308, 149–53; Lee et al., *Proc. Natl. Acad. Sci. U.S.A.* 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human adenylate cyclase. For example, treatment may include a modulation of expression of the differentially expressed genes and/or the gene encoding the human adenylate cyclase. The differential expression information may indicate whether the expression or activity of the differentially expressed gene or gene product or the human adenylate cyclase gene or gene product are up-regulated or down-regulated.

Screening Methods

The invention provides assays for screening test compounds which bind to or modulate the activity of a adenylate cyclase polypeptide or a adenylate cyclase polynucleotide. A test compound preferably binds to a adenylate cyclase polypeptide or polynucleotide. More preferably, a test compound decreases or increases adenylate cyclase activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to adenylate cyclase polypeptides or polynucleotides or to affect adenylate cyclase activity or adenylate cyclase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies, for example, the active site of the adenylate cyclase polypeptide, such that normal biological activity is prevented. Examples of such small molecules include, but are not limited to, small peptides or peptide-like molecules.

In binding assays, either the test compound or the adenylate cyclase polypeptide can comprise a detectable label, such as a fluorescent, radioisotopic, chemiluminescent, or enzymatic label, such as horseradish peroxidase, alkaline phosphatase, or luciferase. Detection of a test compound which is bound to the adenylate cyclase polypeptide can then be accomplished, for example, by direct counting of radioemmission, by scintillation counting, or by determining conversion of an appropriate substrate to a detectable product.

Alternatively, binding of a test compound to a adenylate cyclase polypeptide can be determined without labeling either of the interactants. For example, a microphysiometer can be used to detect binding of a test compound with a adenylate cyclase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a adenylate cyclase polypeptide (McConnell et al., *Science* 257, 1906–1912, 1992).

Determining the ability of a test compound to bind to a adenylate cyclase polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying bio-specific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a adenylate cyclase polypeptide can be used as a "bait protein" in a two-hybrid assay or three-hybrid assay (see, e.g., U.S. Pat. No. 5,283, 317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the adenylate cyclase polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a adenylate cyclase polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the adenylate cyclase polypeptide.

It may be desirable to immobilize either the adenylate cyclase polypeptide (or polynucleotide) or the test compound to facilitate separation of bound from unbound forms of one or both of the interactants, as well as to accommodate automation of the assay. Thus, either the adenylate cyclase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a adenylate cyclase polypeptide (or polynucleotide) can be accomplished in any vessel suitable for containing the reactants. Examples of such vessels include microtiter plates, test tubes, and microcentrifuge tubes.

In one embodiment, the adenylate cyclase polypeptide is a fusion protein comprising a domain that allows the adenylate cyclase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed adenylate cyclase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a adenylate cyclase polypeptide (or polynucleotide) or a test compound can be immobilized utilizing conjugation of biotin and streptavidin. Biotinylated adenylate cyclase polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a adenylate cyclase polypeptide, polynucleotide, or a test compound, but which do not interfere with a desired binding site, such as the active site of the adenylate cyclase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the adenylate cyclase polypeptide or test compound, enzyme-linked assays which rely on detecting an activity of the adenylate cyclase polypeptide, and SDS gel electrophoresis under non-reducing conditions.

Screening for test compounds which bind to a adenylate cyclase polypeptide or polynucleotide also can be carried out in an intact cell. Any cell which comprises a adenylate cyclase polypeptide or polynucleotide can be used in a cell-based assay system. A adenylate cyclase polynucleotide can be naturally occurring in the cell or can be introduced using techniques such as those described above. Binding of the test compound to a adenylate cyclase polypeptide or polynucleotide is determined as described above.

Enzyme Assays

Test compounds can be tested for the ability to increase or decrease the adenylate cyclase activity of a human adenylate cyclase polypeptide. Adenylate cyclase activity can be measured, for example, as described in U.S. Pat. No. 5,795,756.

Enzyme assays can be carried out after contacting either a purified adenylate cyclase polypeptide, a cell membrane preparation, or an intact cell with a test compound. A test compound which decreases enzyme activity of a adenylate cyclase polypeptide by at least about 10, preferably about 50, more preferably about 75, 90, or 100% is identified as a potential therapeutic agent for decreasing adenylate cyclase activity. A test compound which increases enzyme activity of a human adenylate cyclase polypeptide by at least about 10, preferably about 50, more preferably about 75, 90, or 100% is identified as a potential therapeutic agent for increasing human adenylate cyclase activity.

Gene Expression

In another embodiment, test compounds which increase or decrease adenylate cyclase gene expression are identified. A adenylate cyclase polynucleotide is contacted with a test compound, and the expression of an RNA or polypeptide product of the adenylate cyclase polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of adenylate cyclase mRNA or polypeptide expression in the cells can be determined by methods well known in the art for detecting mRNA or polypeptide. Either qualitative or quantitative methods can be used. The presence of polypeptide products of a adenylate cyclase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a adenylate cyclase polypeptide.

Such screening can be carried out either in a cell-free assay system or in an intact cell. Any cell which expresses a adenylate cyclase polynucleotide can be used in a cell-based assay system. The adenylate cyclase polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions which can be administered to a patient to achieve a therapeutic effect. Pharmaceutical compositions of the invention can comprise, for example, a adenylate cyclase polypeptide, adenylate cyclase polynucleotide, ribozymes or antisense oligonucleotides, antibodies which specifically bind to a adenylate cyclase polypeptide, or mimetics, activators, or inhibitors of a adenylate cyclase polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, ie., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition Such labeling would include amount, frequency, and method of administration.

Therapeutic Indications and Methods

The human adenylate cyclase of the invention can be regulated to treat peripheral and central nervous system disorders, disorders of the genito-urinary system including but not limited to benign prostatic hyperplasia and urinary incontinence, obesity, COPD and diabetes.

Peripheral and Central Nervous System Disorders.

Peripheral and central nervous system disorders which may be treated include brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis also can be treated. Similarly, it may be possible to treat cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities, by regulating the activity of human adenyl cyclase.

Pain that is associated with peripheral and central nervous system disorders also can be treated by regulating the activity of human adenyl cyclase. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradiculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania Obesity.

Obesity and overweight are defined as an excess of body fat relative to lean body mass. An increase in caloric intake or a decrease in energy expenditure or both can bring about this imbalance leading to surplus energy being stored as fat. Obesity is associated with important medical morbidities and an increase in mortality. The causes of obesity are poorly understood and may be due to genetic factors, environmental factors or a combination of the two to cause a positive energy balance. In contrast, anorexia and cachexia are characterized by an imbalance in energy intake versus energy expenditure leading to a negative energy balance and weight loss. Agents that either increase energy expenditure and/or decrease energy intake, absorption or storage would be usefull for treating obesity, overweight, and associated comorbidities. Agents that either increase energy intake and/or decrease energy expenditure or increase the amount of lean tissue would be useful for treating cachexia, anorexia and wasting disorders.

This gene, translated proteins and agents which modulate this gene or portions of the gene or its products are useful for treating obesity, overweight, anorexia, cachexia, wasting disorders, appetite suppression, appetite enhancement, increases or decreases in satiety, modulation of body weight, and/or other eating disorders such as bulimia. Also this gene, translated proteins and agents which modulate this gene or portions of the gene or its products are useful for treating obesity/overweight-associated comorbidities including hypertension, type 2 diabetes, coronary artery disease, hyperlipidemia, stroke, gallbladder disease, gout, osteoarthritis, sleep apnea and respiratory problems, some types of cancer including endometrial, breast, prostate, and colon cancer, thrombolic disease, polycystic ovarian syndrome, reduced fertility, complications of pregnancy, menstrual irregularities, hirsutism, stress incontinence, and depression.

Urinary Incontinence

Urinary incontinence (UI) is the involuntary loss of urine. Urge urinary incontinence (UUI) is one of the most common types of UI together with stress urinary incontinence (SUI) which is usually caused by a defect in the urethral closure mechanism. UUI is often associated with neurological disorders or diseases causing neuronal damages such as dementia, Parkinson's disease, multiple sclerosis, stroke and diabetes, although it also occurs in individuals with no such disorders. One of the usual causes of UUI is overactive bladder (OAB) which is a medical condition referring to the symptoms of frequency and urgency derived from abnormal contractions and instability of the detrusor muscle.

There are several medications for urinary incontinence on the market today mainly to help treating UUI. Therapy for OAB is focused on drugs that affect peripheral neural control mechanisms or those that act directly on bladder detrusor smooth muscle contraction, with a major emphasis on development of anticholinergic agents. These agents can inhibit the parasympathetic nerves which control bladder voiding or can exert a direct spasmolytic effect on the detrusor muscle of the bladder. This results in a decrease in intravesicular pressure, an increase in capacity and a reduction in the frequency of bladder contraction. Orally active anticholinergic drugs such as propantheline (ProBanthine), tolterodine tartrate (Detrol) and oxybutynin (Ditropan) are the most commonly prescribed drugs. However, their most serious drawbacks are unacceptable side effects such as dry mouth, abnormal visions, constipation, and central nervous system disturbances. These side effects lead to poor compliance. Dry mouth symptoms alone are responsible for a 70% non-compliance rate with oxybutynin. The inadequacies of present therapies highlight the need for novel, efficacious, safe, orally available drugs that have fewer side effects.

Benign Prostatic Hyperplacia

Benign prostatic hyperplacia (BPH) is the benign nodular hyperplasia of the periuretlral prostate gland commonly seen in men over the age of 50. The overgrowth occurs in the central area of the prostate called the transition zone, which wraps around the urethra BPH causes variable degrees of bladder outlet obstruction resulting in progressive lower urinary tract syndromes (LUTS) characterized by urinary frequency, urgency, and nocturia due to incomplete emptying and rapid refilling of the bladder. The actual cause of BPH is unknown but may involve age-related alterations in balance of steroidal sex hormones.

The selective ??1-adrenoceptor antagonists, such as prazosin, indoramin and tamsulosin are used as an adjunct in the symptomatic treatment of urinary obstruction caused by BPH, although they do not affect on the underlying cause of BPH. In BPH, increased sympathetic tone exacerbates the degree of obstruction of the urethra through contraction of prostatic and urethral smooth muscle. These compounds inhibit sympathetic activity, thereby relaxing the smooth muscle of the urinary tract. Uroselective ??1-antagonists and ??1-antagonists with high tissue selectivity for lower urinary tract smooth muscle that do not provoke hypotensive side-effects should be developed for the treatment.

Drugs blocking dihydrotestosterone have been used to reduce the size of the prostate. 5??-reductase inhibitors such as finasteride are prescribed for BPH. These agents selectively inhibit 5??-reductase which mediates conversion of testosterone to dihydrotestosterone, thereby reducing plasma dihydrotestosterone levels and thus prostate growth.

The 5??-reductase inhibitors do not bind to androgen receptors and do not affect testosterone levels nor do they possess feminizing side-effects.

Androgen receptor antagonists are used for the treatment of prostatic hyperplasia due to excessive action or production of testosterone. Various antiandrogens are under investigation for BPH including chlormadione derivatives with no estrogenic activity, orally-active aromatase inhibitors, luteinizing hormone-releasing hormone (LHRH) analogues.

COPD

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders*, 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Diabetes

Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes (juvenile onset), which results from a loss of cells which make and secrete insulin, and type 2 diabetes (adult onset), which is caused by a defect in insulin secretion and a defect in insulin action.

Type 1 diabetes is initiated by an autoimuune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Likewise, agents that reduces new blood vessel growth can be used to treat the eye complications that develop in both diseases.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a adenylate cyclase polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects adenylate cyclase activity can be administered to a human cell, either in vitro or in vivo, to reduce adenylate cyclase activity. The reagent preferably binds to an expression product of a human adenylate cyclase gene. If the expression product is a protein, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 mmole of liposome delivered to about $10^6$ cells, more preferably about 1.0 μg of DNA per 16 nmole of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about. 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is Well within the capability of those skilled in the art. A therapeutically effective dose refers to that amount of active ingredient which increases or decreases adenylate cyclase activity relative to the adenylate cyclase activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a adenylate cyclase gene or the activity of a adenylate cyclase polypeptide by at least about 10, preferably about 50, more preferably about 75, 90, or 100% relative to the absence of the reagent. The effectiveness of the mechanism chosen to decrease the level of expression of a adenylate cyclase gene or the activity of a adenylate cyclase polypeptide can be assessed using methods well known in the art, such as hybridization of nucleotide probes to adenylate cyclase-specific mRNA, quantitative RT-PCR, immunologic detection of a adenylate cyclase polypeptide, or measurement of adenylate cyclase activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human adenylate cyclase also can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding adenylate cyclase in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a adenylate cyclase also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Adenylate Cyclase Activity

The polynucleotide of SEQ ID NO: 4 is inserted into the expression vector pCEV4 and the expression vector pCEV4-adenylate cyclase polypeptide obtained is transfected into human embryonic kidney 293 cells. From these cells extracts are obtained and the adenylate cyclase activity is meassured in the following assay: A volume of 1.0 microliter of either $H_2O$, NaF, guanylyl-5'-imidodiphosphate (Gpp-NHp), isoproterenol, or isoproterenol+GppNHp are added to each of five reaction tubes and maintained at 0° C. Next, 25 microliter of reaction mixture A (Tris Acetate 100 mM, pH 7.4; KCl 20 mM; $MgCl_2$ 10.0 mM; phosphoenolpyruvate 20 mM; ATP 2.0 mM; GTP 0.02 mM; dithiothreitol 2.0 mM; bovine serum albumin 0.04%; cAMP 0.66 mM; pyruvate kinase 1.0 mg/ml and alpha 32 P-ATP, 3000 Ci/mmole) are added to each reaction tube. Finally 25 microliter of the cell extract are added to each tube and the reaction is initiated by placing the tubes in a water bath at 37° C. After 30 minutes, the reaction is terminated by the addition of 300 mircroliter of a stopping solution. The assay tubes are heated at 95° C. for 5 minutes. 32 p-cAMP is isolated using Dowex-alumina chromatography. It is shown that the polypeptide of SEQ ID NO: 6 has a adenylate cyclase activity.

EXAMPLE 2

Expression of Recombinant Human Adeynylate Cyclase

The *Pichia pastoris* expression vector pPICZB (Invitrogen, San Diego, Calif.) is used to produce large quantities of recombinant human adenylate cyclase polypeptides in yeast. The adenylate cyclase-encoding DNA sequence is derived from SEQ ID NO:4 or 5. Before insertion into vector pPICZB, the DNA sequence is modified by well known methods in such a way that it contains at its 5'-end an initiation codon and at its 3'-end an enterokinase cleavage site, a His6 reporter tag and a termination codon.

Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human adenylate cyclase polypeptide is obtained.

EXAMPLE 3

Identification of Test Compounds that Bind to Adenylate Cyclase Polypeptides

Purified adenylate cyclase polypeptides comprising a glutathione-S-transferase protein and absorbed onto glutathione-derivatized wells of 96-well microtiter plates are contacted with test compounds from a small molecule library at pH 7.0 in a physiological buffer solution. Human adenylate cyclase polypeptides comprise the amino acid sequence shown in SEQ ID NO:6. The test compounds comprise a fluorescent tag. The samples are incubated for 5 minutes to one hour. Control samples are incubated in the absence of a test compound.

The buffer solution containing the test compounds is washed from the wells. Binding of a test compound to a adenylate cyclase polypeptide is detected by fluorescence measurements of the contents of the wells. A test compound which increases the fluorescence in a well by at least 15% relative to fluorescence of a well in which a test compound is not incubated is identified as a compound which binds to a adenylate cyclase polypeptide.

EXAMPLE 4

Identification of a Test Compound which Decreases Adenylate Cyclase Gene Expression A test compound is administered to a culture of human cells transfected with a adenylate cyclase expression construct and incubated at 37° C. for 10 to 45 minutes. A culture of the same type of cells which have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled adenylate cyclase-specific probe at 65° C. in Express-hyb (CLONTECH). The probe comprises at least 11 contiguous nucleotides selected from the complement of SEQ D NO:4 or 5. A test compound which decreases the adenylate cyclase-specific signal relative to the signal obtained in the absence of the test compound is identified as an inhibitor of adenylate cyclase gene expression.

EXAMPLE 5

Identification of a Test Compound which Decreases Adenylate Cyclase Activity

A test compound is administered to a culture of human cells transfected with a adenylate cyclase expression construct and incubated at 37° C. for 10 to 45 minutes. A culture of the same type of cells which have not been transfected is incubated for the same time without the test compound to provide a negative control. Adenylate cyclase activity is measured using the method of U.S. Pat. No. 5,795,756.

A test compound which decreases the enzyme activity of the adenylate cyclase relative to the enzyme activity in the absence of the test compound is identified as an inhibitor of adenylate cyclase activity.

EXAMPLE 6

Tissue-Specific Expression of Adenylate Cyclase

The qualitative expression pattern of adenylate cyclase in various tissues is determined by Reverse Transcription-Polymerase Chain Reaction (RT-PCR).

To demonstrate that adenylate cyclase is involved in the disease process of diabetes, the following whole body panel is screened to show predominant or relatively high expression: subcutaneous and mesenteric adipose tissue, adrenal gland, bone marrow, brain, colon, fetal brain, heart, hypothalamus, kidney, liver, lung, mammary gland, pancreas, placenta, prostate, salivary gland, skeletal muscle, small intestine, spleen, stomach, testis, thymus, thyroid, trachea, and uterus. Human islet cells and an islet cell library also are tested. As a final step, the expression of adenylate cyclase in cells derived from normal individuals with the expression of cells derived from diabetic individuals is compared.

To demonstrate that adenylate cyclase is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus. Quantitative expression profiling. Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol. Fifty μg of each RNA were treated with DNase I for 1 hour at 37° C. in the following reaction mix: 0.2 U/μl RNase-free DNase I (Roche Diagnostics, Germany); 0.4 U/μl RNase inhibitor (PE Applied Biosystems, Calif.); 10 mM Tris-HCl pH 7.9; 10 mM $MgCl_2$; 50 mM NaCl; and 1 mM DTT.

After incubation, RNA is extracted once with 1 volume of phenol:chloroform:isoamyl alcohol (24:24:1) and once with chloroform, and precipitated with ⅒ volume of 3 M NaAcetate, pH 5.2, and 2 volumes of ethanol.

Fifty μg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/μL. Reverse transcription is carried out with 2.5 μM of random hexamer primers.

TaqMan quantitative analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1×final TaqMan Universal PCR Master Mix (from 2× stock) (PE Applied Biosystems, CA); 1×PDAR control—18S RNA (from 20× stock); 300 nM forward primer; 900 nM reverse primer, 200 nM probe; 10 ng cDNA; and water to 25 µl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

Expression of human adenylate cyclase in liver, skeletal muscle, hypothalamus, islet cells, and adipose tissue is shown in FIG. 51.

EXAMPLE 7

Diabetes: In vivo Testing of Compounds/Target Validation

1. Glucose Production:

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

2. Insulin Sensitivity:

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

3. Insulin Secretion:

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

Compounds that enhance insulin secretion from the pancreas will increase plasma insulin levels and improve the disappearance of plasma glucose following the administration of a glucose load. When measuring insulin levels, test compounds which regulate adenylate cyclase are administered by different routes (p.o., i.p., s.c., or i.v.) to overnight fasted normal rats or mice. At the appropriate time an intravenous glucose load (0.4 g/kg) is given, blood is collected one minute later. Plasma insulin levels are determined. Test compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60, and 90 minutes and plasma glucose levels determined. Test compounds that increase insulin levels will decrease glucose levels and the area-under-the glucose curve when compared to the vehicle-treated group given only glucose.

4. Glucose Production:

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

5. Insulin Sensitivity:

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

6. Insulin Secretion:

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

EXAMPLE 8

In Vivo Testing of Compounds/Target Validation

1. Pain:

Acute Pain

Acute pain is measured on a hot plate mainly in rats. Two variants of hot plate testing are used: In the classical variant animals are put on a hot surface (52 to 56 µC) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10 C where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhythms in activity (Surjo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's Disease

6-Hydroxydopamine (6-OH-DA) Lesion

Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mrn anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP Treatment

The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 µm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxi-dase activity is quenched for 10 min in 0.3% $H_2O_2$±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immuno-reactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,.3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Administration of the putative cognition enhancer prior to the first trial predo-minantly allows assessment of the effects on acquisition, and eventually on consolidation processes. Administration of the testing compound after the first trial allows to assess the effects on consolidation processes, whereas administration before the second trial allows to measure effects on retrieval processes.

The Passive Avoidance Task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*$kg^{-1}$ scopolamine. Scopolamine impairs the memory performance during the retention session 24 hours later. If the test compound increases the enter latency compared with the scopolamine-treated controls, is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-Maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

The invention claimed is:

1. An isolated and purified protein comprising a first polypeptide segment comprising the amino acid sequence shown in SEQ ID NO:6.

2. The protein of claim 1 further comprising a second polypeptide segment comprising an amino acid sequence which is not the amino acid sequence of SEQ ID NO:6, wherein the second polypeptide segment is joined to the first polypeptide segment by means of a peptide bond.

3. A pharmaceutical composition comprising:
a protein comprising the amino acid sequence shown in SEQ ID NO:6; and
a pharmaceutically acceptable carrier.

* * * * *